(12) United States Patent
Wadas et al.

(10) Patent No.: US 10,758,634 B2
(45) Date of Patent: Sep. 1, 2020

(54) COMPOUNDS, COMPOSITIONS AND ASSOCIATED METHODS USING ZIRCONIUM-89 IN IMMUNO-POSITRON EMISSION TOMOGRAPHY

(71) Applicant: Wake Forest University, Winston-Salem, NC (US)

(72) Inventors: Thaddeus J. Wadas, Winston-Salem, NC (US); Darpan N. Pandya, Winston-Salem, NC (US); Nikunj B. Bhatt, Winston-Salem, NC (US)

(73) Assignee: Wake Forest University, Winston-Salem, NC (US)

(*) Notice: Subject to any disclaimer, the term of this patent is extended or adjusted under 35 U.S.C. 154(b) by 0 days.

(21) Appl. No.: 16/085,821

(22) PCT Filed: Mar. 18, 2017

(86) PCT No.: PCT/US2017/023101
§ 371 (c)(1),
(2) Date: Sep. 17, 2018

(87) PCT Pub. No.: WO2017/161356
PCT Pub. Date: Sep. 21, 2017

(65) Prior Publication Data
US 2019/0038785 A1  Feb. 7, 2019

Related U.S. Application Data

(60) Provisional application No. 62/310,460, filed on Mar. 18, 2016, provisional application No. 62/378,822, filed on Aug. 24, 2016, provisional application No. 62/464,063, filed on Feb. 27, 2017.

(51) Int. Cl.
*A61K 51/04* (2006.01)
*A61K 51/10* (2006.01)
*C07D 257/02* (2006.01)
*C07F 7/00* (2006.01)

(52) U.S. Cl.
CPC ...... *A61K 51/0482* (2013.01); *A61K 51/0478* (2013.01); *A61K 51/1093* (2013.01); *C07D 257/02* (2013.01); A61K 2123/00 (2013.01); C07F 7/003 (2013.01)

(58) Field of Classification Search
CPC .......... A61K 51/00; A61K 51/04; A61K 51/10
See application file for complete search history.

(56) References Cited

U.S. PATENT DOCUMENTS

| 7,259,249 B2 | 8/2007 | Griffiths et al. |
| 2005/0002945 A1 | 1/2005 | McBride et al. |
| 2010/0111856 A1 | 5/2010 | Gill et al. |
| 2012/0065365 A1 | 3/2012 | Chen et al. |
| 2014/0147381 A1* | 5/2014 | Espenan ............... A61K 51/083 424/1.45 |
| 2015/0246146 A1 | 9/2015 | Agnew et al. |

FOREIGN PATENT DOCUMENTS

| WO | 2015/051188 A1 | 4/2015 |
| WO | 2015/153772 A2 | 10/2015 |
| WO | 2017/161356 A1 | 9/2017 |

OTHER PUBLICATIONS

Tinianow et al. 'Evaluation of a 3-hydroxypyridin-2-one (2,3-HOPO) Based Macrocyclic Chelator for 89Zr4+ and Its Use for ImmunoPET Imaging of HER2 Positive Model of Ovarian Carcinoma in Mice', Theranostics 2016, vol. 6, Issue 4, pp. 511-521, Feb. 13, 2016, abstract; p. 513, col. 1, para 3; p. 515, col. 2, para2.
International Search Report and Written Opinion dated Jun. 3, 2019 issued in International Application No. PCT/US19/15109.

* cited by examiner

*Primary Examiner* — Michael G. Hartley
*Assistant Examiner* — Jagadishwar R Samala
(74) *Attorney, Agent, or Firm* — Fox Rothschild LLP

(57) ABSTRACT

Disclosed are novel compounds, complexes, compositions and methods using Zirconium-89 combined with azamacrocyclic chelators in connection with PET. The compositions and methods should provide better diagnostic, prognostic and therapeutic oncology treatments relative to the presently available chelator compositions due to a variety of superior properties of the disclosed compositions. The present invention also relates to a superior method of making these compounds, complexes, compositions that allows one to make compounds/complexes (and thus, compositions) that were previously unattainable.

12 Claims, 17 Drawing Sheets

COMPOUNDS, COMPOSITIONS AND ASSOCIATED METHODS USING ZIRCONIUM-89 IN IMMUNO-POSITRON EMISSION TOMOGRAPHY

The present invention claims priority under 35 USC 119(e) to U.S. Provisional Application 62/310,460 filed Mar. 18, 2016 and to U.S. Provisional Application No. 62/378,822 filed Aug. 24, 2016, and to U.S. Provisional Application No. 62/464,063 filed Feb. 27, 2017, the contents of all of which are incorporated by reference in their entireties.

FIELD OF THE INVENTION

The present invention relates to novel compounds, complexes, compositions and methods using Zirconium-89 combined with chelators in connection with PET. The compositions and methods of the present invention should provide better diagnostic, prognostic and therapeutic oncology treatments relative to the presently available chelator compositions due to a variety of superior properties of the disclosed compositions. The present invention also relates to a superior method of making these compounds, complexes, compositions that allows one to make compounds/complexes (and thus, compositions) that were previously unattainable.

BACKGROUND OF THE INVENTION

Immuno-positron emission tomography (PET) is an imaging tool useful in diagnostic, prognostic and therapeutic oncology. Monoclonal antibodies (mAbs) uniquely bind specific antigens produced by tumors, allowing researchers to establish the presence, location, and number of neoplastic foci. MAbs can be produced in nearly unlimited quantities with absolute specificity using the hybridoma method. Treatment using mAbs can have different forms: the mAbs can be administered alone or can be combined with a radioactive molecule, which then provides radiation directly to the tumor cells. The labeling of antibodies with PET isotopes provides not just better sensitivity but also superior resolution. In immuno-PET, mAbs are labeled with various PET radionuclides and used in cancer patients who produce tumor-associated antigens.

Various radionuclides have been used for PET but most of them have limitations that make them unattractive for PET. Direct labeling methodologies using $^{76}$Br ($t_{1/2}$=17 hours) and $^{124}$I ($t_{1/2}$=4 days) encounter the difficulties like loss of immunoreactivity, random radiolabel incorporation and dehalogenation. Indirect labeling using metal such as $^{64}$Cu ($t_{1/2}$ of 12.7 hours) are superior to the direct labeling methodologies but also have their shortcomings such as demetallation and a 36 hour maximal image time.

Zirconium-89 ($^{89}$Zr; $t_{1/2}$, =78.4 h, $\beta^+$: 22.8%) is widely used in immuno-PET applications because its half-life pairs well with the biological half-life of a circulating monoclonal antibody (mAb), and because it can be routinely produced in high specific activity, high radiochemical purity and can be shipped around the world. It is produced by a $^{89}$Y(p,n) $^{89}$Zr reaction and its decay produces two 511 KeV photons that are used in PET meaning that there is no interfering γ-rays for PET detection.

In clinical immuno-PET applications the acyclic iron chelator desferrioxamine B (DFO) is used exclusively to attach $^{89}$Zr to a mAb. FIG. 15 shows $^{89}$Zr to a mAb via the chelator DFO.

Despite the exclusive use of this chelator, it is not optimal for $^{89}$Zr-immuno-PET since the $^{89}$Zr$^{4+}$ prefers ligands that form eight coordinate complexes while DFO can only form a 6 coordinate complex leaving 2 coordination sites vacant (shown by the Xs in the above structure), making it vulnerable to transchelation by endogenous proteins once injected in vivo. The $^{89}$Zr DFO chelation product is in many instances unstable.

Moreover, $^{89}$Zr-transchelation is observed as elevated levels of radioactivity in the liver and kidney that eventually localize to the bones of animals receiving the radiotracer. This non-specific uptake complicates the biodistribution and clearance profile of new mAbs and retards the critical processes that identify the most promising mAbs to be carried forward into clinical trials. The need for $^{89}$Zr chelators with improved stability remains an important and active area of research.

The current strategy to prepare clinical $^{89}$Zr-radiopharmaceuticals relies on the reaction of $^{89}$Zr-oxalate ($^{89}$Zr—OX) with the bifunctional chelator (BFC), desferrioxamine B (DFO), and its analogues, which are derivatives of the siderophore desferral, a growth promoting agent secreted by *Streptomyces pilosus*. Additionally, several second generation $^{89}$Zr chelators rely on the use of $^{89}$Zr—OX as a radiochemistry precursor. However, the use of an $^{89}$Zr—OX as a zirconium source has always been viewed as problematic with the current strategy producing $^{89}$Zr-mAbs with radiochemical yields, purities and specific activities that are not optimal. Recently, others have described efforts to optimize the production of $^{89}$Zr-mAbs, and although they were able to reduce the amount of mAb used in each radiochemical reaction while maintaining excellent radiochemical purity and specific activities that are comparable to that achieved using alternative strategies, the methodology still relied on the use of $^{89}$Zr—OX, which has many of the problems disclosed below.

Drawbacks to the present technologies used for $^{89}$Zr is that oxalate (or oxalic acid) is used in the purification of $^{89}$Zr, and the zirconium source currently for $^{89}$Zr-radiopharmaceutical preparation is $^{89}$Zr-oxalate. The barriers to using oxalate is that it is highly toxic, it decalcifies the blood, Ca-oxalate obstructs kidney tubules causing kidney stones, and it must be removed by purification before formulating the $^{89}$Zr-radiopharmaceutical for injection. This processing increases the time and handling exposure. Moreover, the reaction success using oxalate is dependent on the volume of the reaction. Thus, it is desired to not rely on oxalate for purification of $^{89}$Zr. Others have proposed metathetical conversion to the chloride ion from oxalate. However, older traditional methods of this metathetical conversion are cumbersome and require very harsh conditions like elevated temperatures, the use of concentrated acids and peroxide, specialized techniques like vacuum sublimation, difficulties in automating the process and finally, enhanced exposure to radiation. More recently some improvements have been made but the methods are still not optimal. The newer methods still require elevated temperatures for reagent drying, relatively long reaction/purification times, difficulties in automating the process and still enhanced radiation exposure.

Significant effort has been expended on $^{89}$Zr chelator development, and several new ligand classes have been reported. However, none of these new ligands produce $^{89}$Zr-complexes that are superior to $^{89}$Zr-DFO in vivo. Moreover, others have described a tris(hydroxypyridinone) ligand that was conjugated to Trastuzumab (TmAb) and radiolabeled with $^{89}$Zr. However, studies in vivo revealed significant instability when compared with $^{89}$Zr-DFO-trastuzumab and demonstrated three fold more radioactivity localized in the bones of mice receiving the hydroxypyridinone-based radiotracer. Accordingly, little progress has been made in identifying ligands that bind $^{89}$Zr to produce radiometal complexes that are superior to $^{89}$Zr-DFO, which currently is considered to be the "gold standard" in $^{89}$Zr-PET radiopharmaceutical applications.

Replacing $^{89}$Zr—OX with a different $^{89}$Zr precursor has never been evaluated in the preparation of $^{89}$Zr-immuno-PET agents.

It is with these problems and needs in mind that the present invention was developed.

BRIEF SUMMARY OF THE INVENTION

In an embodiment of the present invention, new AMCs (Azamacrocycles) have been developed that will be successfully used in radiopharmaceutical development. AMCs should prove to be more popular to use relative to their corresponding acyclic ligands due to their enhanced stability, which is imparted by the macrocyclic effect. Additionally, the chemistry of AMC ligands can be tuned by the addition of a variety of functional groups into the macrocycle, through variations in pendant arm composition, or through reactive functional groups that allow for their facile conjugation to a variety of peptides, proteins, antibodies and nanoparticles. Although some AMCs are known (such as 1,4,7,10-tetraazacyclododecane-1,4,7,10-tetraacetic acid (DOTA)) and other AMCs are either used in clinically approved radiopharmaceuticals or are used in combination with radiopharmaceutical undergoing clinical trials, to the inventors' knowledge, there is no disclosure or description of using AMCs as $^{89}$Zr chelators. Exploiting the advantages of AMCs as $^{89}$Zr chelators will likely allow for improved $^{89}$Zr radiopharmaceutical production and enhance immuno-PET applications.

In one embodiment, the present invention relates to a new paradigm for generating AMCs including the use of $^{89}$Zr (halide)$_4$ such as $^{89}$ZrCl$_4$ in the radiosynthesis thereby eliminating the need for the use of oxalate in the synthesis of $^{89}$Zr chelators. The use of $^{89}$ZrCl$_4$ (or alternatively, $^{89}$ZrBr$_4$, $^{89}$ZrF$_4$ or $^{89}$ZrI$_4$) facilitates the synthesis of $^{89}$Zr-AMCs, which have a superior biodistribution profile when compared to $^{89}$Zr-DFO. In an embodiment, the present invention relates to $^{89}$Zr-azamacrocycles that have superior in vivo stability relative to other chelators (that are used in conjunction with mAbs as radiotracers) that are presently available, including $^{89}$Zr-DFO. In a variation, it is expected that the new $^{89}$Zr-azamacrocycle compositions of the present invention will be useful for not only mAb based radiotracers, but can be used in conjunction with other circulating peptides or nanoparticles that may be effective peptide or nanoparticle based radiotracers. It is expected that upon evaluation of these new $^{89}$Zr-complexes in clinically relevant peptides and mAbs, they will demonstrate that their superior stability is retained upon bioconjugation with the peptides, nanoparticles and mAbs. It is expected that this invention will lead to a new paradigm for $^{89}$Zr radiopharmaceutical development and hasten the implementation of improved immuno-PET applications that can enhance diagnosis, treatment and quality of care. $^{89}$ZrCl$_4$ exists as an additional $^{89}$Zr precursor, anecdotal reports suggested that the use of chloride would be detrimental to antibody function. In one embodiment of the invention, AMCs are used as $^{89}$Zr chelators. In a variation, $^{89}$ZrCl$_4$ provides a pathway to $^{89}$Zr-AMC synthesis. In one embodiment, the present invention relates to a new and improved metathetical conversion of oxalate to chloride, which greatly reduces the problems alluded to above in the section Background of the Invention. In an embodiment, the new method relates to using 1.0M HCl with the addition of HEPES buffer (4-(2-hydroxyethyl)-1-piperazineethanesulfonic acid buffer), which provides $^{89}$ZrCl$_4$ at pH 7 meaning the process time is less than 15 minutes and meaning that the process can also be automated. Because the process can be automated, it is conducive to being used as part of a kit. Thus, in one embodiment, the present invention relates to a kit that converts oxalate to chloride using HEPES buffer and 1.0 M HCl leading to the production of $^{89}$ZrCl$_4$.

In an embodiment, the present invention relates to preparation of $^{89}$Zr-DFO and also the preparation of $^{89}$Zr-azamacrocycles using $^{89}$ZrCl$_4$. These reactions do not have the drawbacks present when using $^{89}$Zr-oxalate. Reaction with $^{89}$ZrCl$_4$ takes less time, generally does not require the higher temperatures and can be done at a more convenient pH (e.g., 7). Moreover, the radiochemical purity is 100%. Further, if a kit is used, the conversion process using the kit does not affect radiochemistry and mAbs, proteins, peptides, and nanoparticles can be used.

In one embodiment, the present invention relates to the synthesis and use of $^{89}$Zr-DOTA-TOC and $^{89}$Zr-DOTA-Trastuzumab (TmAb), which will be evaluated in somatostatin receptor subtype 2 positive (SSTR2+) and Her2/neu+ relevant animal models, respectively. It is expected that these compositions/compounds will demonstrate superior in vivo stability while part of a radiopharmaceutical.

In one embodiment, the present invention relates to synthesis and use of $^{89}$Zr-AMCs that exhibit superior in vivo stability when compared to $^{89}$Zr-DFO, which is expected to be retained when conjugated to a clinically relevant antibody, peptide or nanoparticle.

With this expected showing, the present invention in embodiments of the invention will find the optimal $^{89}$Zr-chelate stability, 2) it will create a new paradigm for $^{89}$Zr-chelate development by replacing DFO as the "gold standard" 3) it will reduce the time needed for $^{89}$Zr-radiopharmaceutical evaluation in preclinical and clinical studies, and 4) it will allow clinically relevant radiopharmaceuticals to be utilized at clinical sites such as rural hospitals that don't have the resources to maintain and operate radiochemistry infrastructure such as a $^{68}$Ge/$^{68}$Ga generator (one of the PET radionuclides which is most commonly used).

DETAILED DESCRIPTION OF THE INVENTION

Figure 1:
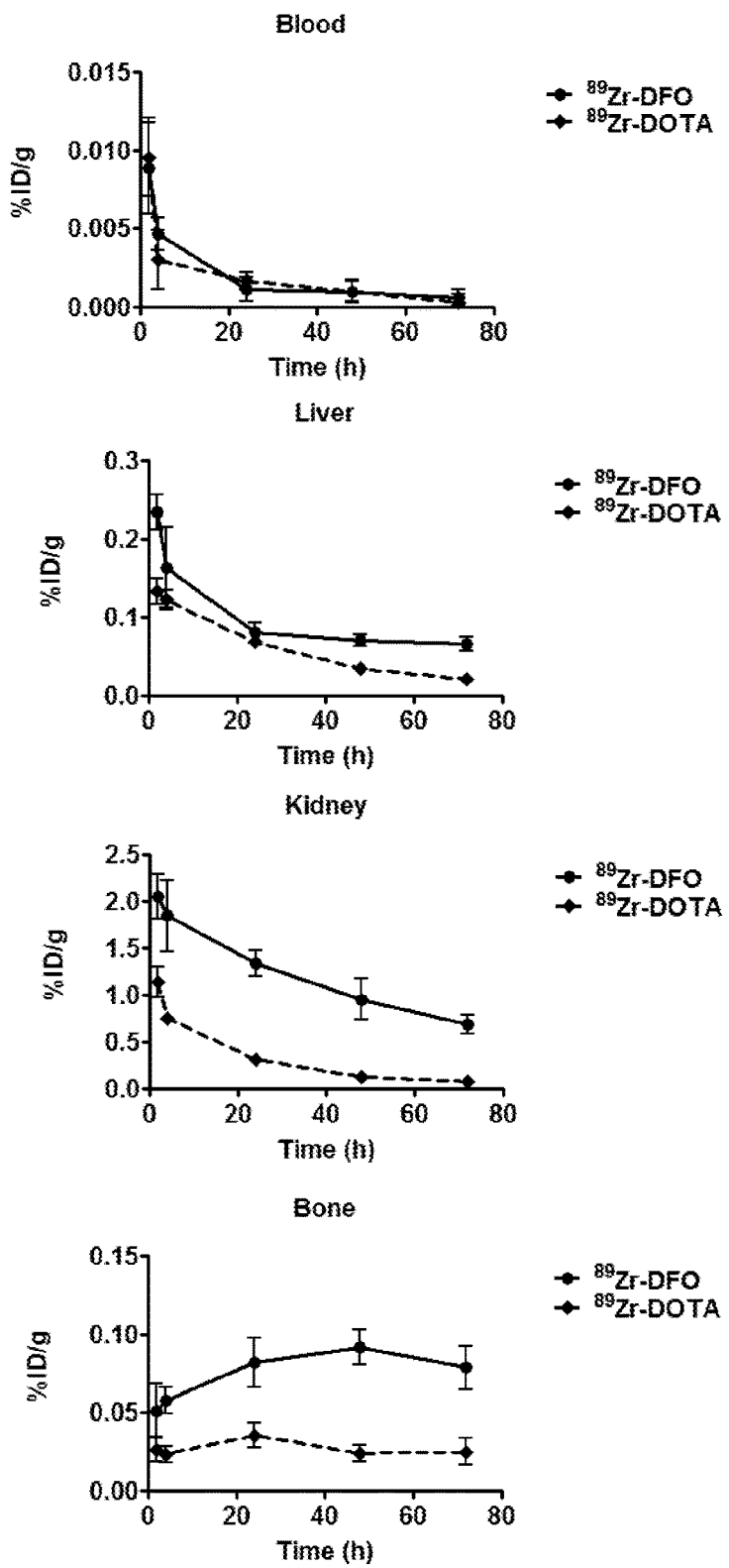
FIG. 1 shows in vivo biodistribution data for $^{89}$Zr-DOTA and $^{89}$Zr-DFO in selected tissues (n=6/group). Both $^{89}$Zr-complexes experience rapid blood clearance. Mice injected with $^{89}$Zr-DOTA retained less radioactivity in the liver, kidney and bone, suggesting it is more stable in vivo than $^{89}$Zr-DFO. This in vivo data corroborates the in vitro data (Table 1).

The present invention relates to compounds, compositions and methods using Zirconium-89 combined with chelators in connection with PET. The compositions and methods of the present invention will provide better diagnostic, prognostic and therapeutic oncology treatments relative to the presently available chelator compositions due to a variety of superior properties of the disclosed compounds/compositions.

As used herein, the term "heteroaryl" refers to a three- to fifteen-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heterocyclic", "heterocycle", or the term "heterocyclyl" refers to a three to fifteen membered heterocyclic ring optionally having one or more degrees of unsaturation containing one or more heteroatomic substitutions selected from S, SO, SO$_2$, O, or N. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "aryl" refers to an aromatic carbocycle containing from 3 to 15 carbon atoms wherein the rings may optionally contain fused ring systems. Examples of aryl include, but are not limited to, phenyl, 2-naphthyl, 1-naphthyl, 1-anthracenyl, and the like.

In an embodiment, the present invention relates to compounds, compositions and methods using the compounds of formula I:

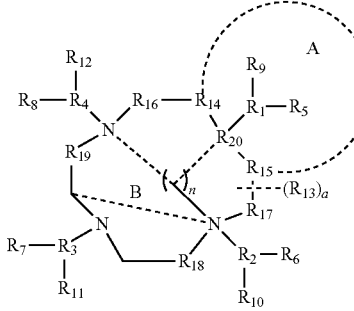

Formula I wherein
$R_1$, $R_2$, $R_3$, and $R_4$ are independently H or CH;
and wherein when $R_1$ is H, $R_5$ and $R_9$ are not present;
when $R_2$ is H, $R_6$ and $R_{10}$ are not present;
when $R_3$ is H, $R_7$ and $R_{11}$ are not present;
and when $R_4$ is H, $R_8$ and $R_{12}$ are not present;
$R_5$, $R_6$, $R_7$, and $R_8$ are independently H or CH$_3$;
$R_9$, $R_{10}$, $R_{11}$, and $R_{12}$ are independently

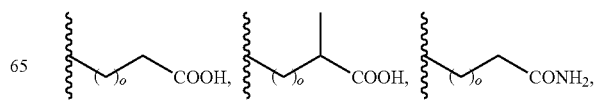

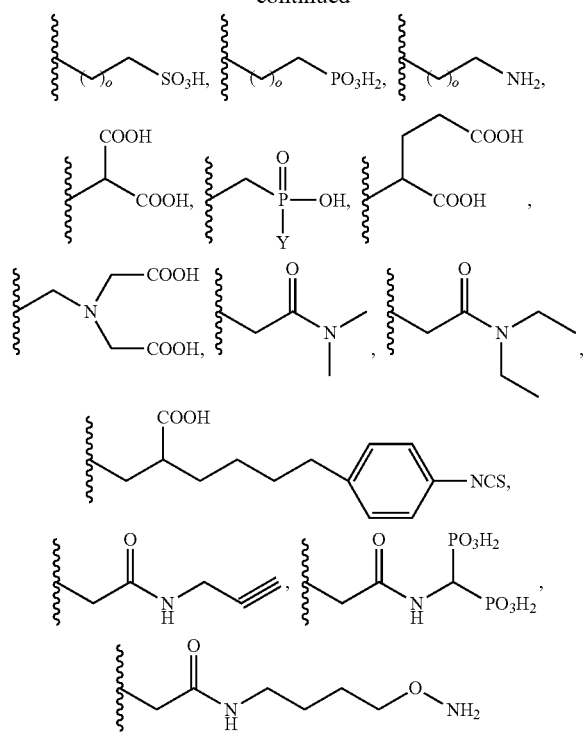

or alternatively, the combination of any one or more of a) $R_1$, $R_5$ and $R_9$, or b) $R_2$, $R_6$, and $R_{10}$, or c) $R_3$, $R_7$, and $R_{11}$, or d) $R_4$, $R_8$ and $R_{12}$ are all independently

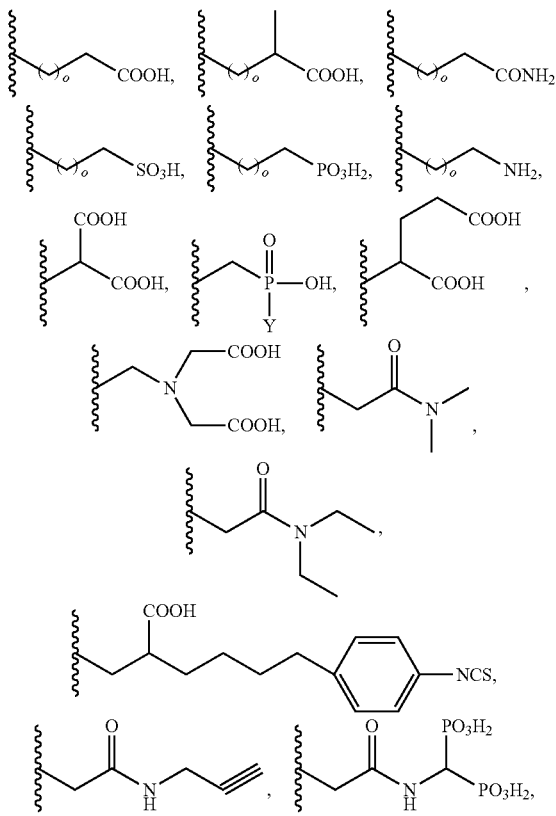

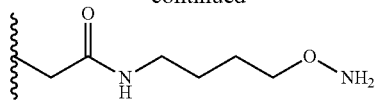

wherein Y is Ph, Bn, Me, Et or n-Bu; and each o is independently an integer 0 or 1.

$R_{13}$ is

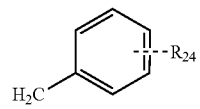

wherein $R_{24}$ is independently H, —OH, —NH$_2$, —C(O)NH$_2$, —NO$_2$, —(CH$_2$)$_{1-3}$O(CH$_2$)$_{1-3}$CH$_3$, —C(O)O(CH$_2$)$_{1-3}$CH$_3$, —OC(O)(CH$_2$)$_{0-3}$CH$_3$, halogen, —(CH$_2$)$_{1-3}$C(O)(CH$_2$)$_{0-3}$CH$_3$, cyano, C$_{2-5}$carboxyl, thiol, —C(O)(CH$_2$)$_{0-3}$CH$_3$, substituted or unsubstituted C$_{1-15}$alkyl, substituted or unsubstituted C$_{1-15}$alkenyl, substituted or unsubstituted C$_{1-15}$alkynyl, substituted or unsubstituted C$_{4-15}$alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)(CH$_2$)$_{0-3}$CH$_3$, C$_{2-5}$carboxyl, —(CH$_2$)$_{1-3}$C(O)(CH$_2$)$_{0-3}$CH$_3$, nitro, amino, thiol, succinimide, maleimide, aminooxyl, acetylene, N$_3$, acetamino, azide, —C(O)O(CH$_2$)$_{1-3}$CH$_3$, —OC(O)(CH$_2$)$_{0-3}$CH$_3$, halogen, C$_{1-5}$alkynyl, and NCS;

a is 0-3;

$R_{14}$ and $R_{15}$ are independently CH or CH$_2$ functionalities; wherein $R_{14}$ and $R_{15}$ are independently CH if and when at least one $R_{13}$ is present;

$R_{16}$, $R_{17}$, $R_{18}$, and $R_{19}$ are —(CH$_2$)$_x$— wherein x is 1, 2, or 3;

$R_{18}$ may optionally be substituted with at least one substituent wherein said substituent is a benzyl amino functionality; that is, one of the hydrogens on one of the methylene groups in $R_{18}$ would be replaced by a benzyl amino functionality (for example, a para substituted benzyl amino functionality);

$R_{20}$ is N or O; wherein $R_{20}$ is N if $R_1$, $R_5$ and $R_9$ are present;

and wherein the dotted circle A that comprises the atoms/variables $R_{14}$ and $R_{15}$ and $R_{20}$ to which they are attached may optionally comprise a pyridine group; and when the dotted circle A that contains the atoms/variables $R_{14}$ and $R_{15}$ and the nitrogen to which they are attached comprise a pyridine group, $R_1$, $R_5$, and $R_9$ are not present;

and wherein the chelator optionally has a direct bond represented by the dotted line B;

wherein when the chelator has a direct bond represented by the dotted line B, the intervening linker represented by the group —N(R$_3$(R$_7$)(R$_{11}$))—CH$_2$—CH$_2$— is not present;

wherein n is 0-4; and when n is 1-4, the chelator comprises either a cis C$_{1-4}$alkylene group linkage from the nitrogen directly attached to variable R$_2$ to the nitrogen directly attached to R$_1$ or alternatively, a trans linkage from the nitrogen directly attached to variable $R_2$ to the nitrogen directly attached to $R_4$; and which also comprises $^{89}Zr$.

In one variation, the compounds described above (and below) can be part of a composition that comprises salts that can be made with oxalic acid, $^{89}ZrCl_4$, or other known salts.

In an embodiment, the present invention relates to compounds, compositions and methods comprising using the compound of formula II:

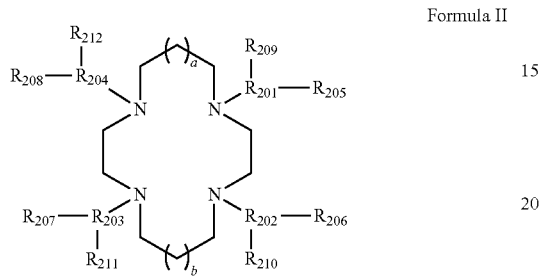

Formula II wherein $R_{201}$, $R_{202}$, $R_{203}$, $R_{204}$ are independently —CH— or —(CH$_2$)$_x$—CH— wherein x is 1-4; $R_{205}$, $R_{206}$, $R_{207}$, $R_{208}$, $R_{209}$, $R_{210}$, $R_{211}$, and $R_{212}$ are independently a hydrogen, hydroxyl, hydroxamate, phosphate, isopthalamide, tereptha-lamide, hydroxypyridinone, or a phenol wherein the phenol group is optionally substituted with one or more substituents selected from the group consisting of methyl, ethyl, at least another hydroxyl, cyano, nitro, carboxyl, amino, or phosphate, sulfate, sulfite, —CONH$_2$; a is 0, 1 or 2 and b is 0, 1 or 2.

In an embodiment, both $R_{205}$ and $R_{209}$, or both $R_{206}$ and $R_{210}$, or both $R_{207}$ and $R_{211}$, or both $R_{208}$ and $R_{212}$ are not hydrogen. That is, in these four pairs of substituents, at least one substituent in these four pair is a moiety that is not hydrogen.

In an embodiment, the compounds of the present invention include DOTAM, DOTP and DOTA as shown below (with and without Zr).

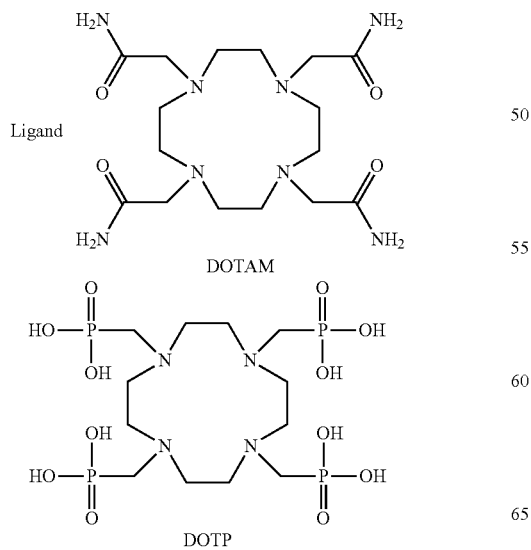

Ligand

DOTAM

DOTP

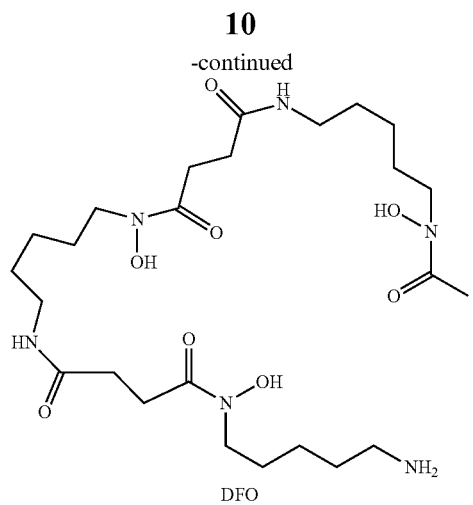

DFO

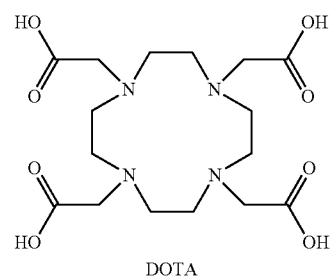

DOTA

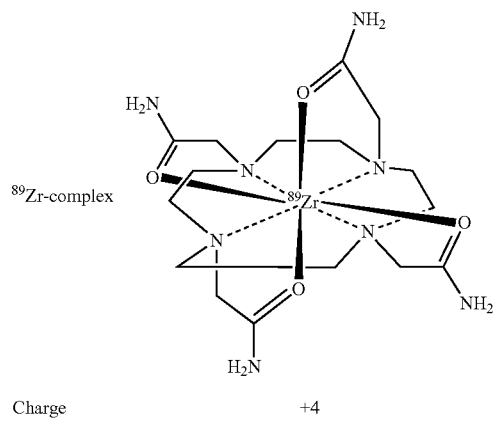

$^{89}$Zr-complex

Charge +4

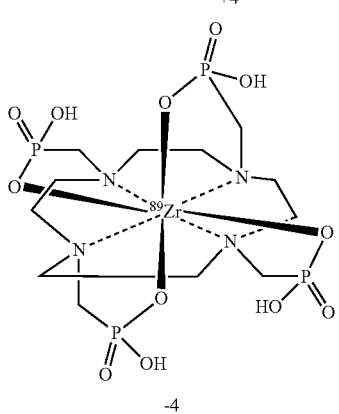

-4

-continued

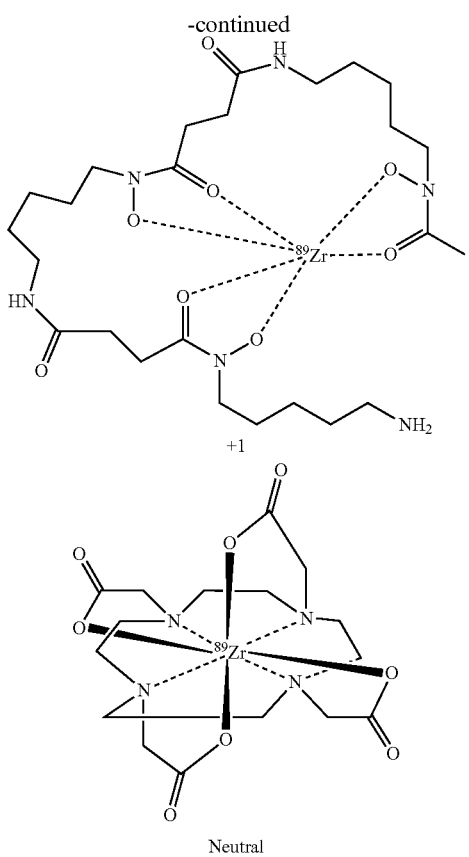

+1

In an embodiment, Zr-1,4,7-triazacyclononane-1,4,7-triacetic acid (Zr-NOTA) and 1,4,7,10-tetraazacyclododecane-1,4,7,10-tetraacetic acid (Zr-DOTA) have been synthesized and characterized by mass spectrometry. See structure Zr-NOTA below.

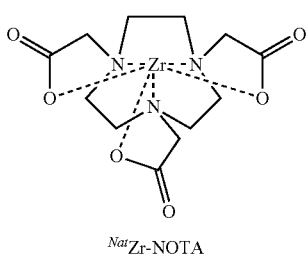

$^{Nat}$Zr-NOTA

Theoretical: 413.0 [(M + Na)$^+$]
Found: 413.4 [(M + Na)$^+$]

Theoretical: 391.0 [(M + H)$^+$]
Found: 391.4 [(M + H)$^+$]

$^{89}$ZrCl$_4$ exists as an additional $^{89}$Zr precursor, anecdotal reports suggested that the use of chloride would be detrimental to antibody function. Accordingly, in one aspect of the present invention, the use of $^{89}$ZrCl$_4$ was compared with $^{89}$Zr—OX as a precursor for $^{89}$Zr-radiopharmaceutical preparation to determine if $^{89}$ZrCl$_4$ provided any significant advantages over the latter starting material in $^{89}$Zr-immuno-PET development.

In an embodiment, the present invention relates to methods and processes using $^{89}$ZrCl$_4$ to generate new complexes and compositions. In one embodiment, $^{89}$ZrCl$_4$ can be used instead of oxalate. In an embodiment, the use of $^{89}$ZrCl$_4$ can be used with both acyclic as well as cyclic chelators. In one embodiment, the use of $^{89}$ZrCl$_4$ improves reaction outcomes and uses less harsh conditions than the corresponding reaction with oxalates. In one embodiment, the present invention relates to the reaction of DOTA with $^{89}$ZrCl$_4$ to give a product. Note that scheme 1 shows the DOTA reacts with $^{89}$ZrCl$_4$ but not with the Zr-oxalate.

Scheme 1

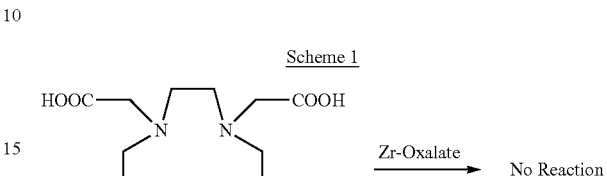

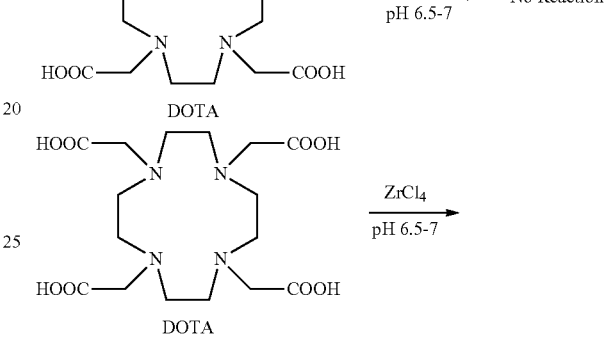

In an embodiment, the present invention relates to compounds that have been made using $^{Nat}$ZrCl$_4$ such as the compounds shown below.

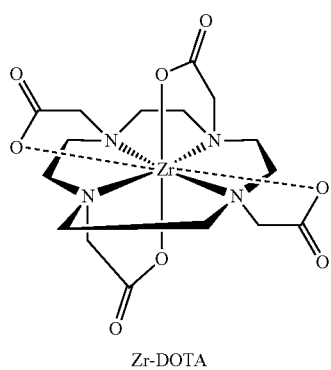

Zr-DOTA

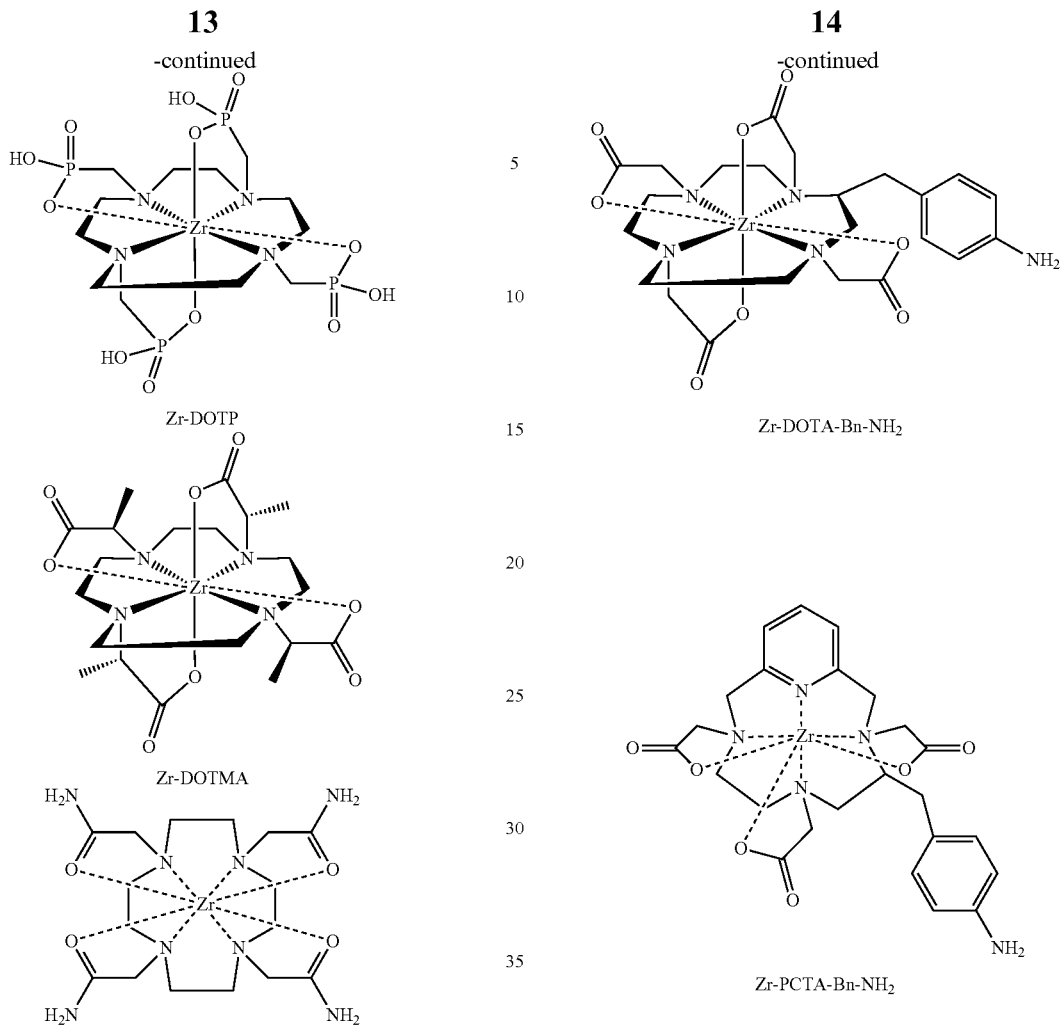
Moreover, the following compounds on the right have also been made as shown below from the chelator indicated:
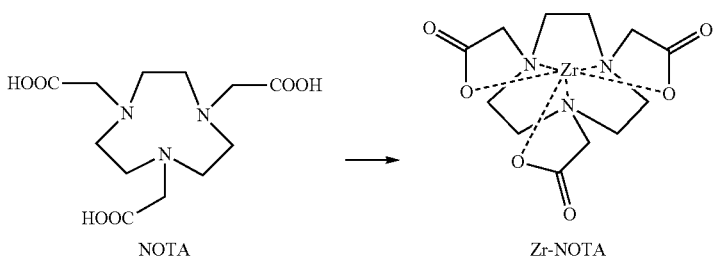
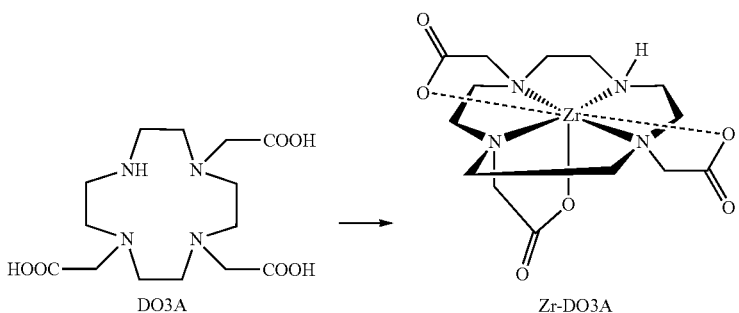

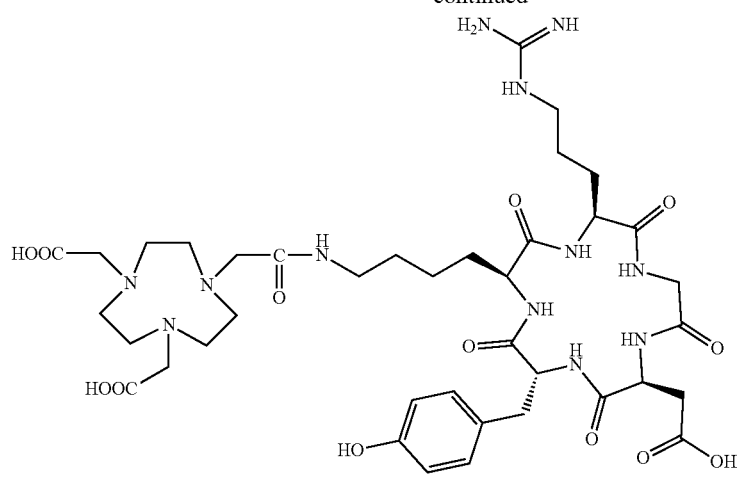
NOTA-c(RGDyK)
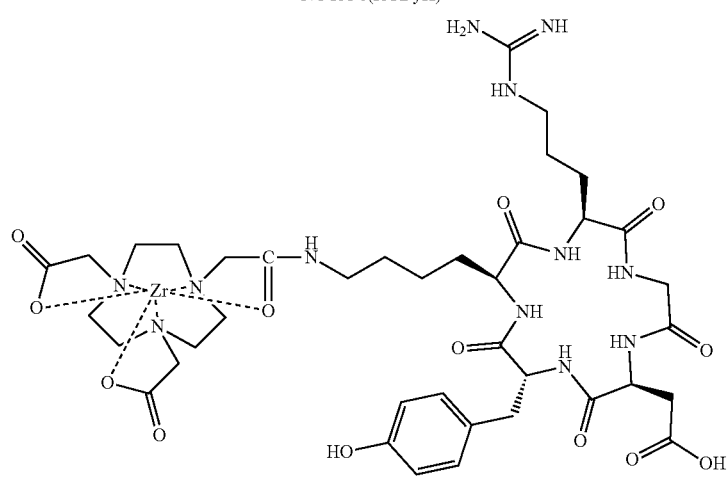
Zr-NOTA-c(RGDyK)
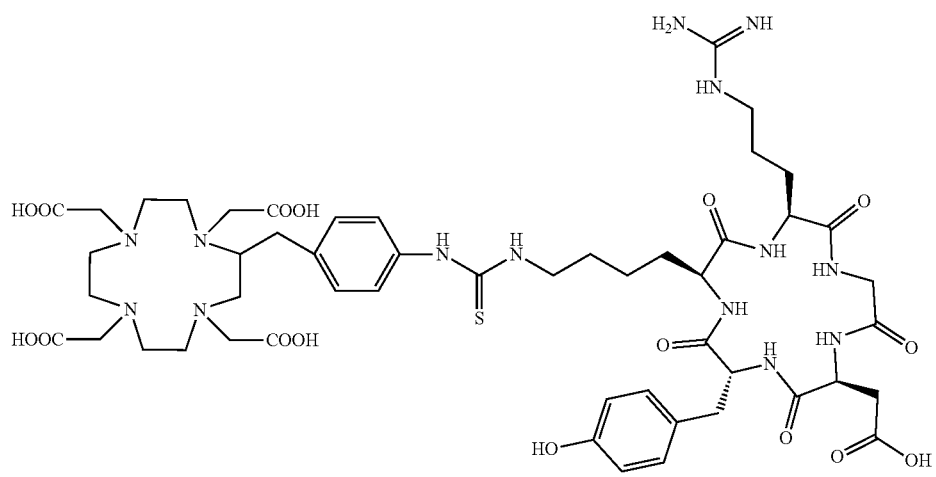
DOTA-c(RGDyK)

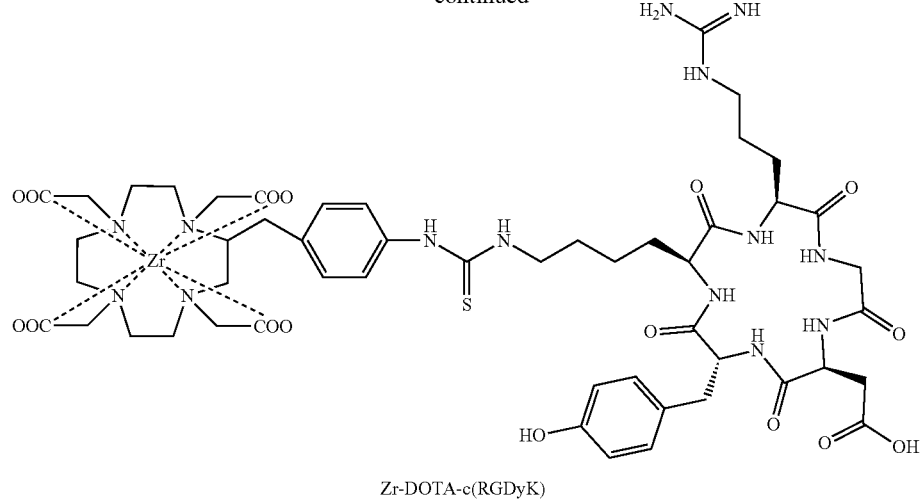
Zr-DOTA-c(RGDyK)
In an embodiment, the present invention relates to compounds, chelators, complexes, compositions, and methods using the compounds/chelators of Formulas III-XI:
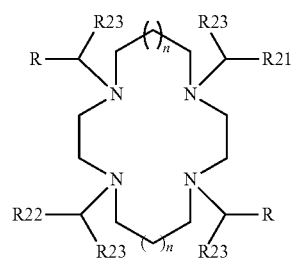
Formula III
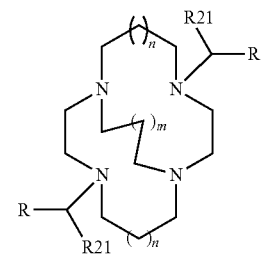
Formula IV
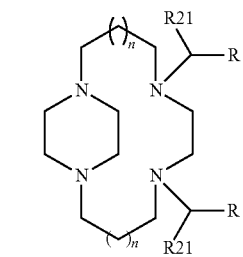
Formula V
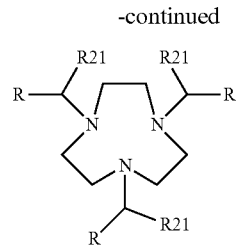
Formula VI
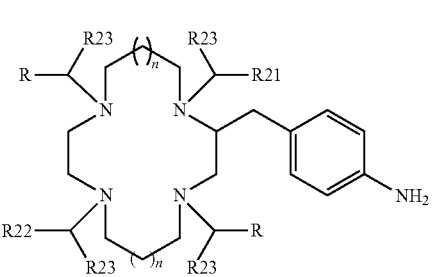
Formula VII
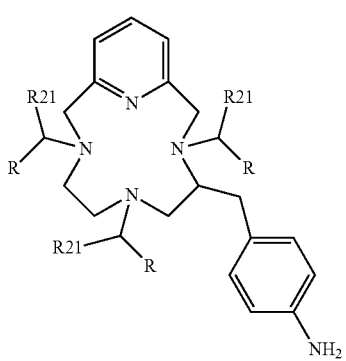
Formula VIII -continued Formula IX

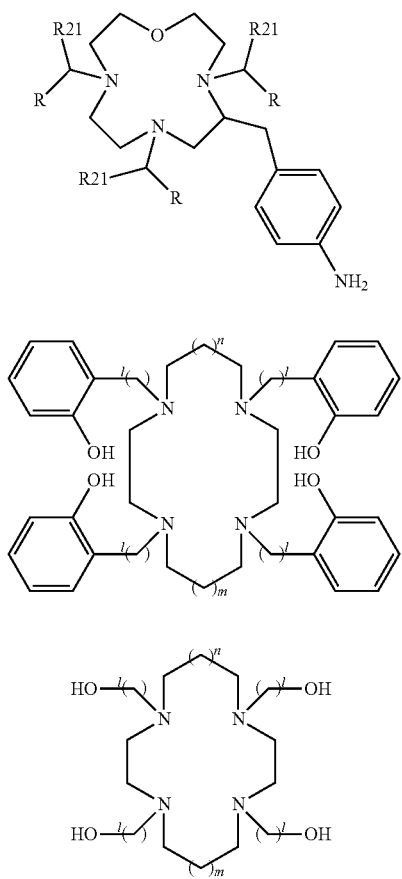

Formula X

Formula XI wherein in the compounds/chelators represented by Formulae III-XI, l ("el") is 0, 1 or 2; n is 0, 1 or 2; m is 0, 1, or 2; R, $R_{21}$, $R_{22}$ and $R_{23}$ are independently selected from the group consisting of H, COOH, $C_{1-4}$alkyl, $PO_3H_2$, and $CONH_2$.

In an embodiment, R, $R_{21}$, $R_{22}$ and $R_{23}$ are independently selected from the group consisting of

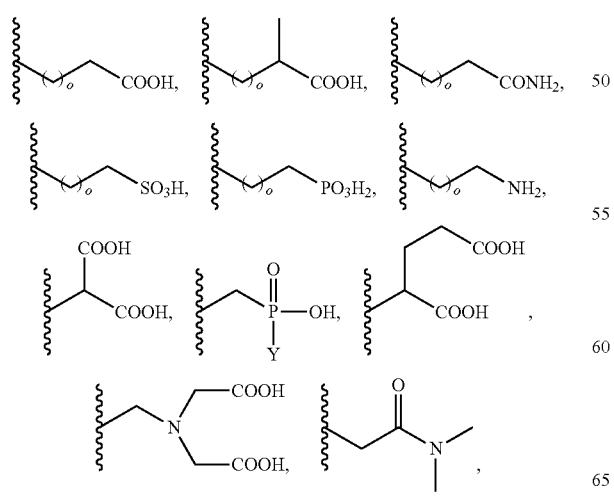

-continued

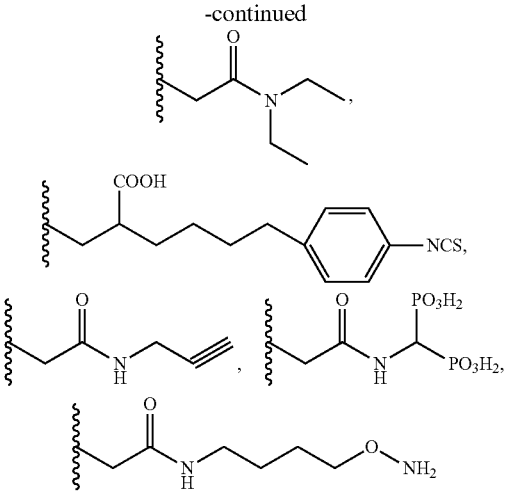

or alternatively, the combination of R, $R_{21}$, $R_{22}$ and $R_{23}$ and the methine group to which they are attached are each independently selected from the group consisting of

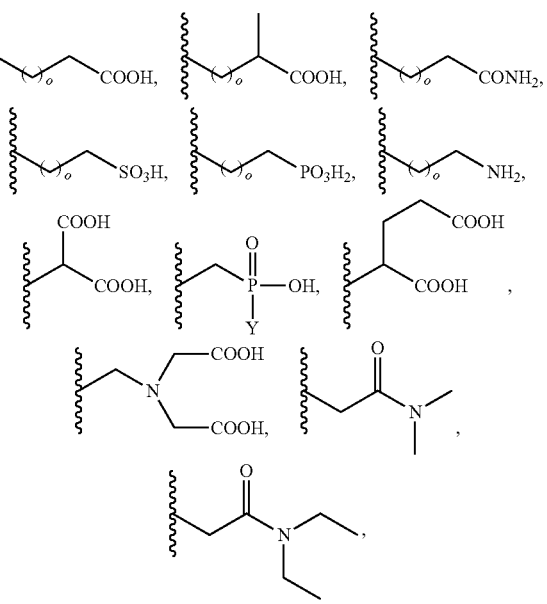

wherein Y is Ph, Bn, Me, Et or n-Bu; and each o is independently an integer 0 or 1. In one variation, the complexes contain $^{89}Zr$. In an embodiment, the complexes can be made with $^{89}ZrCl_4$. In one variation, the complexes may further be linked to one or more of monoclonal antibodies, peptides, proteins, and nanoparticles. In one embodiment, the complexes are linked to one or more monoclonal antibodies.

In an embodiment, the present invention relates to an ability to make stable $^{89}$Zr-azamacrocycles (complexes). Previously, others perceived $^{89}$Zr-Azamacrocycles (AMCs) to be unstable. While azamacrocycles such as 1,4,7,10-tetraazacyclododecane-1,4,7,10-tetraacetic acid (DOTA) have been used extensively to synthesize PET radiotracers, they have not found utility in $^{89}$Zr-radiopharmaceutical development due to the perceived instability of the $^{89}$Zr-AMC complex, which has been reported in the prior art. Because the $^{89}$Zr$^{4+}$ ion is thought to be oxophilic, the prior art reports suggest that the lack of stability arises from the coordination of the $^{89}$Zr$^{4+}$ ion by nitrogen atoms within the AMC. Moreover, additional literature reports suggest that only oxygen-rich ligands would be ideal chelators for the $^{89}$Zr$^{4+}$ ion, provide superior in vivo stability and limit the retention of $^{89}$Zr and radiation dose to non-target organs such as the liver, kidney and bone. Based upon these criteria, others have believed that AMCs are excluded as efficient $^{89}$Zr chelators. However, the data included in this application directly refutes these literature assertions that $^{89}$Zr-AMC complexes are unstable in vitro and in vivo. The in vitro stability data demonstrates that $^{89}$Zr-DOTA is completely inert to EDTA, DTPA and serum challenge, and the in vivo data demonstrates that liver, kidney and bone retention of this radio-complex is less than that of the "gold standard" $^{89}$Zr-DFO.

In one variation, the above molecules represented by Formulas I-XI can be used to generate new chelator-click pairs that enhance the coupling efficiency, specific activity and clearance of the resulting radiopharmaceutical. In one example, the below reaction scheme shows an exemplary embodiment of the present invention. It should be understood that the below DOTA-PEG-BCN molecule contemplates the insertion of $^{89}$Zr into it.

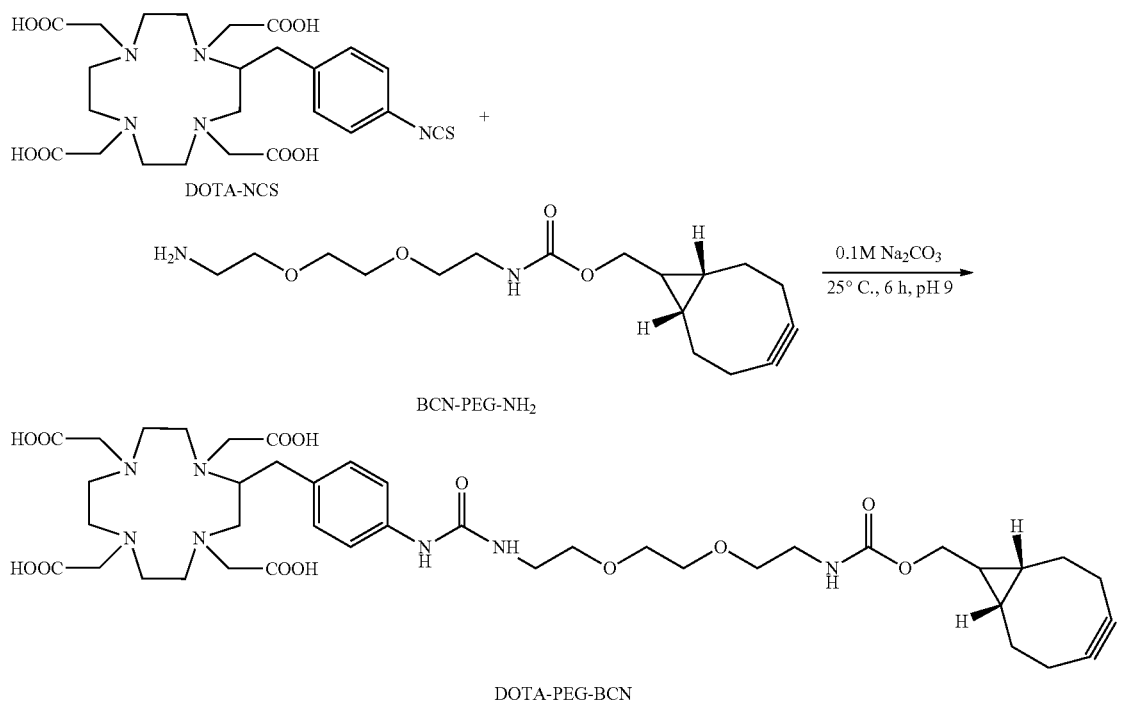

Electrospray Mass spectroscopy results verified the presence of the above DOTA-PEG-BCN molecules in the presence of $^{Nat}$Zr (m/e's of 962.29 H$^+$ salt, 984.27 Na$^+$ salt) and in the absence of $^{Nat}$Zr (m/e's of 876.42 H$^+$ salt, 898.40 Na$^+$ salt).

In one variation, the various click moieties that can be used are represented by the below molecules

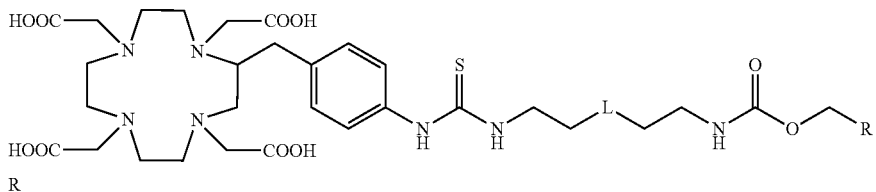

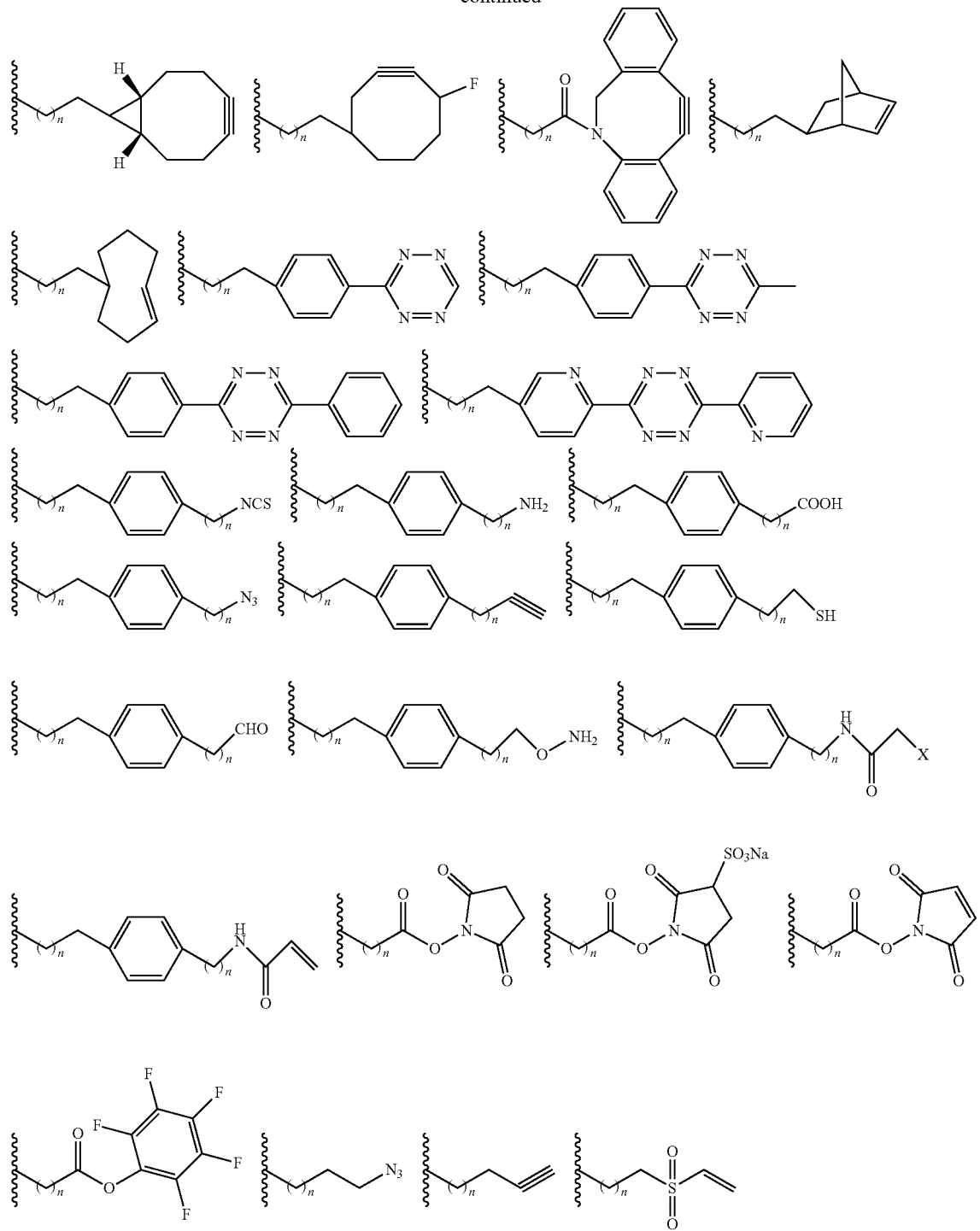

Wherein each X is independently Cl or Br; and each n is independently an integer from 0 to 5.

In a variation of the chelator click molecules, the linker functionality can be cationic moieties, anionic moieties, neutral moieties, enzyme substrates or decomposable moieties such as those shown below. In an embodiment, the linker functionality can be an enzyme cleavable linkage. Thus, the linker can be ideally suited to the chemical environment in which it is to be used.

L

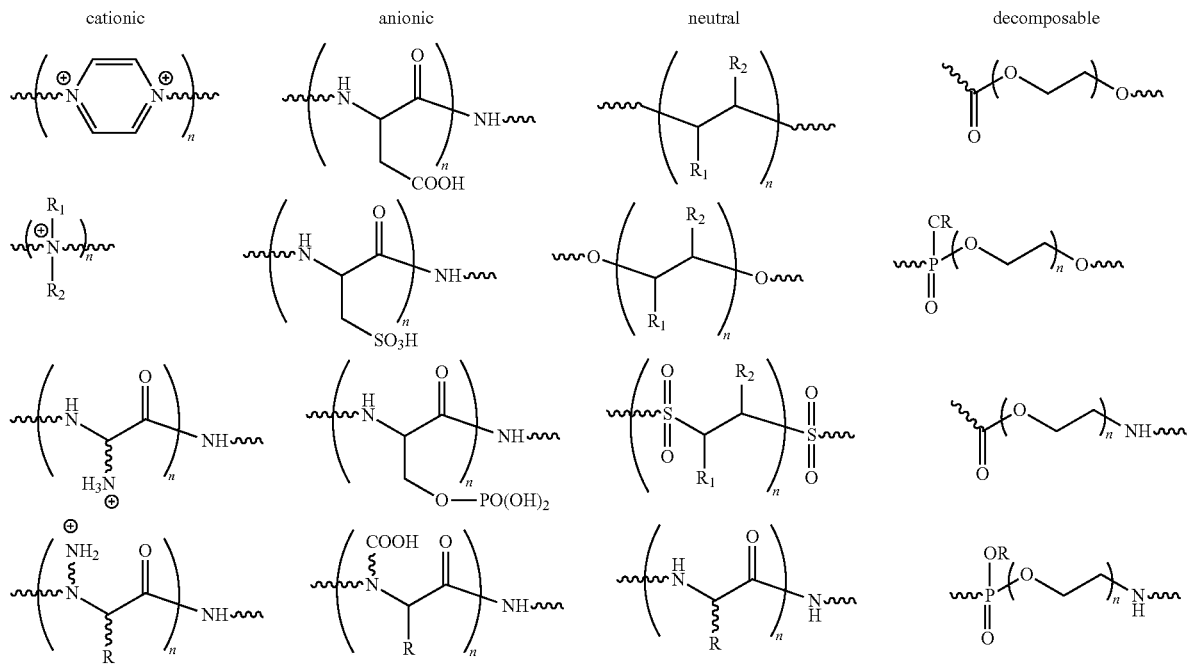

Wherein each of R, $R_1$ and $R_2$ is independently $C_{1~10}$ alkyl, $C_{1~10}$ alkenyl, $C_{1~10}$ alkynyl, $C_{1~10}$ aryl, $C_{1~10}$ arylalkyl or $C_{1~10}$ heteroaryl; and each n is independently an integer from 1 to 20.

In one variation, the linker functionality as shown above is ideally made to achieve a certain length that will make it ideally suited to the purpose that it is to be used.

In one variation, the complexes can be used as part of a pharmaceutical composition. In one embodiment, the complexes that are optionally linked to one or more of antibodies, peptides, proteins, and nanoparticles can be used in various methods. For example, in one embodiment, the complexes that are optionally linked to one or more of antibodies, peptides, proteins, and nanoparticles may be used in PET imaging spectroscopy. In an embodiment, the complexes that are optionally linked to one or more of antibodies, peptides, proteins, and nanoparticles may be used in dosimetry, therapy and intraoperative surgical guidance. In an embodiment, the complexes that are optionally linked to one or more of antibodies, peptides, proteins, and nanoparticles may be linked to the biomolecule through a pendant arm, pendant arm modification, or functional group incorporated into the carbon backbone of the macrocycle. In one embodiment, two or more chelators may be used in combination with $^{89}$Zr or other radionuclei (such as $^{90}$Y, $^{177}$Lu or $^{225}$Ac), wherein the two chelators may perform different functions. For example, one of the chelators may contain $^{89}$Zr and be used for imaging and the other may be used for therapeutic use. In one embodiment, the chelators that may contain $^{89}$Zr may be DFO and another chelator that contains either $^{90}$Y, $^{177}$Lu or $^{225}$Ac may be DOTA.

In one embodiment, the invention relates to kits allowing one to use the technology of the present invention. For example, one kit may allow the conversion of $^{89}$Zr—OX (wherein OX is oxalate) to $^{89}$ZrCl$_4$. One kit may allow the formation of a complex that contains one of the above identified chelators with $^{89}$Zr to form a complex. One kit may allow a complex containing a chelator and $^{89}$Zr to be linked to one or more of monoclonal antibodies, peptides, proteins, or nanoparticles. In one embodiment, the kit may allow any or all of the above transformations to occur. For example, one kit may allow conversion of $^{89}$Zr(ox)$_2$ to $^{89}$ZrCl$_4$, which may in turn be used to form a complex with one of the above-identified chelators, which may optionally also contain the ability for the complex to be linked to one or more of monoclonal antibodies, peptides, proteins, or nanoparticles. Alternatively, the kit may allow the preparation of DFO-mAbs (containing $^{89}$Zr) by using $^{89}$ZrCl$_4$. The kit may also contain the requisite materials necessary for the kit to be used in PET imaging, dosimetry or intraoperative surgical guidance. The kit may contain one or more of buffer (such as HEPES buffer), syringes, chelators, $^{89}$Zr(ox)$_2$, $^{89}$ZrCl$_4$, HCl (such as 1.0 M HCl), monoclonal antibodies, peptides, proteins, nanoparticles, vials to perform requisite reactions/transitions (such as linking antibodies, peptides, proteins, nanoparticles to complexes containing the chelator and $^{89}$Zr), and products that allow automation of transitions.

Thus, the present invention offers many advantages over that of the prior art including the facility of generating radiotracer for $^{89}$Zr-immuno-PET imaging using one ligand and one process, improved reactions using $^{89}$ZrCl$_4$ relative to those using $^{89}$Zr(ox)$_2$ including the ability to make compounds/complexes that previously were unable to be made, the ability to use kits that do not require harsh conditions (relative to corresponding prior art transitions) and are automation and cGMP friendly. Other advantages include making complexes (e.g. complexes containing macrocycles) that show superior in vitro and in vivo behavior relative to the complexes that are currently available including the ability to make these complexes using kit technology. Moreover, the present invention also relates to new chelators that previously were unknown.

The present invention further provides a conjugates comprising: the tetrazamacrocyclic compound represented by the various chemical formulas disclosed herein, $^{89}$Zr, and a bioactive substance or a chemically active substance bound to the tetrazamacrocyclic compound or the coordination compound. Specifically, the conjugate of the present disclosure comprises one or more bioactive substance(s) or chemically active substance(s) directing the conjugate to a targeted tissue, organ, receptor or other biologically expressed composition. In an embodiment, the bioactive substance or the chemically active substance is selective or specific for the targeted organ or tissue.

Broadly, the bioactive substance or the chemically active substance may be an antibody, an amino acid, a nucleoside, a nucleotide, an aptamer, a protein, an antigen, a peptide, a nucleic acid, an enzyme, a lipid, an albumin, a cell, a carbohydrate, a vitamin, a hormone, a nanoparticle, an inorganic support, a polymer, a single molecule or a drug. Specific examples of the bioactive substance or the chemically active substance include: steroid hormones for the treatment of breast and prostate lesions; somatostatin, bombesin, CCK, and neurotensin receptor binding molecules for the treatment of neuroendocrine tumors; CCK receptor binding molecules for the treatment of lung cancer; ST receptor and carcinoembryonic antigen (CEA) binding molecules for the treatment of colorectal cancer; dihyroxyindolecarboxylic acid and other melanin producing biosynthetic intermediates for the treatment of melanoma; integrin receptor; fibroblast activation protein alpha (FAP) and atherosclerotic plaque binding molecules for the treatment of vascular diseases; and amyloid plaque binding molecules for the treatment of brain lesions. Examples of the bioactive substance or the chemically active substance also include synthetic polymers such as polyaminoacids, polyols, polyamines, polyacids, oligonucleotides, aborols, dendrimers, and aptamers.

In an embodiment, the present invention relates to the incorporation of a bioactive substance or chemically active substance that may be selected from among nanoparticles, antibodies (e.g., NeutroSpect®, Zevalin® and Herceptin®), proteins (e.g., TCII, HSA, annexin and Hb), peptides (e.g., octreotide, bombesin, neurotensin and angiotensin), nitrogen-containing simple or complex carbohydrates (e.g., glucosamine and glucose), nitrogen-containing vitamins (e.g., vitamin A, $B_1$, $B_2$, $B_{12}$, C, $D_2$, $D_3$, E, H and K), nitrogen-containing hormones (e.g., estradiol, progesterone and testosterone), nitrogen-containing active pharmaceuticals (e.g., celecoxib or other nitrogen-containing NSAIDs, AMD3100, CXCR4 and CCR5 antagonists) and nitrogen-containing steroids.

Some embodiments of the present invention may include conjugates having multiple bioactive substances or chemically active substances. For example, to increase specificity for a particular target tissue, organ receptor or other biologically expressed composition, multiple bioactive substances or chemically active substances may be utilized. In such instances, the bioactive substances or chemically active substances may be the same or different. For example, a single conjugate may possess multiple antibodies or antibody fragments, which are directed against a desired antigen or hapten. Typically, the antibodies used in the conjugate are monoclonal antibodies or antibody fragments that are directed against a desired antigen or hapten. Thus, for example, the conjugate may include two or more monoclonal antibodies having specificity for a desired epitope and thereby increasing concentration of the conjugate at the desired site. Similarly, and independently, a conjugate may include two or more different bioactive substances or chemically active substances each of which is targeted to a different site on the same target tissue or organ. By utilizing multiple bioactive substances or chemically active substances in this manner, the conjugate is advantageously concentrated at several areas of the target tissue or organ, potentially increasing the effectiveness of therapeutic treatment. In an embodiment, the bioactive substances may comprise peptides, proteins, peptide or protein dimers, trimers and multimers. Further, the conjugate may have a ratio of bioactive substances or chemically active substances, designed to concentrate the conjugate at a target tissue or organ and optimally achieve the desired therapeutic and/or diagnostic results while minimizing non-target deposition. Alternatively and/or additionally, the present invention relates to a two-step, pre-targeting strategy.

In an embodiment, the present invention further provides a method for preparing a conjugate, including: 1) preparing the tetrazamacrocyclic compound according to the present disclosure; 2) binding a bioactive substance or a chemically active substance to the tetrazamacrocyclic compound; and 3) coordinating a metal element with the tetrazamacrocyclic compound to form a complex. The order of the steps 2) and 3) is interchangeable. As described herein, the bioactive substance or the chemically active substance may be utilized variously as a therapeutic agent, a diagnostic agent or a prognostic agent.

The present disclosure further provides a pharmaceutical composition comprising the conjugate of the present disclosure and a pharmaceutically acceptable carrier excipient, vehicle, auxiliary, adjuvant, or diluent. Specifically, the pharmaceutical composition of the present disclosure comprises a conjugate, which forms a complex with a metal, dispersed in a pharmaceutically acceptable carrier. The pharmaceutically acceptable carrier, excipient, vehicle, auxiliary, adjuvant, or diluent is typically a substance which is pharmaceutically inert, confers a suitable consistency or form to the composition, and does not diminish the therapeutic or diagnostic efficacy of the conjugate. The carrier is generally considered to be "pharmaceutically or pharmacologically acceptable" if it does not produce an unacceptably adverse, allergic or other untoward reaction when administered to a mammal, especially human.

Subjects that may be treated by the compounds and compositions of the present invention include, but are not limited to, horses, cows, sheep, pigs, mice, dogs, cats, primates such as chimpanzees, gorillas, rhesus monkeys, and, humans. In an embodiment, a subject is a human in need of treatment.

The selection of the pharmaceutically acceptable carrier tends, at least in part, to be a function of the desired route of administration. In general, metallopharmaceutical compositions of the present disclosure can be formulated for any route of administration so long as the target tissue is available via that route. For example, suitable routes of administration include, but are not limited to, oral, parenteral (e.g., intravenous, intraarterial, subcutaneous, rectal, intramuscular, intraorbital, intracapsular, intraspinal, intraperitoneal or intrasternal), topical (nasal, transdermal or intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal routes.

Examples of the pharmaceutically acceptable carrier for use in pharmaceutical compositions of the present disclosure are well known to those of ordinary skill in the art and may be selected by considering a number of factors. The pharmaceutical composition of the present disclosure is effective for treating tumors. Adequate bioactive substances or chemically active substances and radioactive metals may be used depending on the desired purposes.

In an embodiment, the compositions of the present invention may be used as injectables. The composition intended for injection may be prepared according to any known method, and such compositions may contain one or more agents selected from the group consisting of solvents, co-solvents, solubilizing agents, wetting agents, suspending agents, emulsifying agents, thickening agents, chelating agents, antioxidants, reducing agents, antimicrobial preservatives, buffers, pH adjusting agents, bulking agents, protectants, tonicity adjustors, and special additives. Moreover, other non-toxic pharmaceutically-acceptable excipients which are suitable for the manufacture of injectables may be used.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycethanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents.

Oily suspensions may be formulated by suspending the active ingredient in a vegetable oil, for example *arachis* oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or *arachis* oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, sterile water for injection (SWFI), Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

Dosage and regimens for the administration of the pharmaceutical compositions of the present disclosure can be readily determined by those with ordinary skill in diagnosing or treating diseases. It is understood that the dosage of the conjugates will be dependent upon the age, sex, health and body weight of the recipient, kind of concurrent treatment, if any, frequency of treatment, and the nature of the effect desired. For any mode of administration, the actual amount of the conjugate delivered, as well as the dosing schedule necessary to achieve the advantageous effects described herein, will also depend, in part, on such factors as the bioavailability of the conjugate, the disorder being treated or diagnosed, the desired therapeutic or diagnostic dose, and other factors that will be apparent to those of ordinary skill in the art. The dose administered to an animal, particularly human, in the context of the present disclosure should be sufficient to affect the desired therapeutic or diagnostic response in the animal over a reasonable period of time. Specifically, the dosage of the pharmaceutical composition may vary depending on the body weight, age, sex and health condition of the patient, diet, administration time, administration route, excretion ratio and severity of disease. In case of an adult patient, a dosage of 20-200 mg/day may be administered once or several times a day.

Radiolabeled scintigraphic and/or PET imaging agents having a suitable amount of radioactivity are also provided by the present disclosure. In forming diagnostic radioactive complexes, it is generally preferred to form radioactive complexes in solutions containing radioactivity at concentrations of about 0.01 millicurie (mCi) to 100 mCi per mL. Generally, the unit dose to be administered has a radioactivity of about 0.01 mCi to about 100 mCi, specifically about 1 mCi to about 30 mCi. The volume of the solution to be injected at unit dosage is from about 0.01 mL to about 10 mL. The amount of the radiolabeled conjugate appropriate for administration is dependent upon the distribution profile of the chosen conjugate in the sense that a rapidly cleared conjugate may need to be administered in higher doses than one that is cleared less rapidly. In vivo distribution and localization can be tracked by standard scintigraphic/PET techniques at an appropriate time subsequent to administration, typically between 30 minutes and 180 minutes depending upon the rate of accumulation at the target site with respect to the rate of clearance at the non-target tissue.

In a variation, the present invention relates to pharmaceutical compositions. The pharmaceutical composition may contain pharmaceutically acceptable salts, solvates, and prodrugs thereof, and may contain diluents, excipients, carriers, or other substances necessary to increase the bioavailability or extend the lifetime of the compounds of the present invention.

The pharmaceutical compositions containing a compound of the invention may be in a form suitable for injection either by itself or alternatively, using liposomes, micelles, and/or nanospheres.

Thus, in another embodiment, the present invention provides a pharmaceutical formulation solution comprising the conjugate(s) as described herein or a salt thereof.

A solution of the invention may be provided in a sealed container, especially one made of glass, either in a unit dosage form or in a multiple dosage form.

Any pharmaceutically acceptable salt of a compound of the conjugate(s) as described herein may be used for preparing a solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. In an embodiment, the conjugate(s) as described herein is a hydrochloric acid salt including a mono, di, or trihydrochloride.

Any solvent which is pharmaceutically acceptable and which is able to dissolve the conjugate(s) as described herein or a pharmaceutically acceptable salt thereof may be used. The solution of the invention may also contain one or more additional components such as a co-solubilizing agent (which may be the same as a solvent), a tonicity adjustment agent, a stabilizing agent, a preservative, or mixtures thereof. Examples of solvents, co-solubilizing agents, tonicity adjustment agents, stabilizing agents and preservatives which may be suitable for a solution formulation are described below.

Suitable solvents and co-solubilizing agents may include, but are not limited to, water; sterile water for injection (SWFI); physiological saline; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols; esters of polyoxyethylenated fatty acids; polysorbates, e.g., Tween™, polyoxyethylene derivatives of polypropyleneglycols, e.g., Pluronics™.

Suitable tonicity adjustment agents may include, but are not limited to, pharmaceutically acceptable inorganic chlorides, e.g. sodium chloride; dextrose; lactose; mannitol; sorbitol and the like.

Preservatives suitable for physiological administration may be, for instance, esters of parahydroxybenzoic acid (e.g., methyl, ethyl, propyl and butyl esters, or mixtures of them), chlorocresol and the like.

In an embodiment, radioprotectants can also be included in the formulation. These additives include but are not limited to gentisic acid and L-ascorbic acid or combinations thereof.

Suitable stabilizing agents include, but are not limited to, monosaccharides (e.g., galactose, fructose, and fucose), disaccharides (e.g., lactose), polysaccharides (e.g., dextran), cyclic oligosaccharides (e.g., alpha-, beta-, gamma-cyclodextrin), aliphatic polyols (e.g., mannitol, sorbitol, and thioglycerol), cyclic polyols (e.g. inositol) and organic solvents (e.g., ethyl alcohol and glycerol).

The above mentioned solvents and co-solubilizing agents, tonicity adjustment agents, stabilizing agents and preservatives can be used alone or as a mixture of two or more of them in a solution formulation.

In an embodiment, a pharmaceutical solution formulation may comprise the conjugate(s) as described herein or a pharmaceutically acceptable salt thereof, and an agent selected from the group consisting of sodium chloride solution (i.e., physiological saline), dextrose, mannitol, or sorbitol, wherein the agent is in an amount of less than or equal to 5%. The pH of such a formulation may also be adjusted to improve the storage stability using a pharmaceutically acceptable acid or base.

In the solutions of the invention the concentration of the conjugate(s) as described herein or a pharmaceutically acceptable salt thereof may be less than 100 mg/mL, or less than 50 mg/mL, or less than 10 mg/mL, or less than 5 mg/mL and greater than 0.01 mg/mL, or between 0.5 mg/mL and 5 mg/mL, or between 1 mg/mL and 3 mg/mL. In an embodiment, the concentration that is used is the ideal concentration to be sufficiently cytotoxic to the cancer cells yet limit the toxicity on other cells.

Suitable packaging for the pharmaceutical solution formulations may be all approved containers intended for parenteral use, such as plastic and glass containers, ready-to-use syringes and the like. In an embodiment, the container is a sealed glass container, e.g. a vial or an ampoule. A hermetically sealed glass vial is particularly preferred.

In an embodiment, the packaging may include cGMP/cGLP/cGCP/cGPvP as packaging.

According to an embodiment of the present invention, there is provided, in a sealed glass container, a sterile, injectable solution comprising one or more of the radiopharmaceutical(s), radiolabeled conjugate(s), $^{89}$Zr-radiolabeled protein, peptide, antibody and/or nanoparticle as described herein or a pharmaceutically acceptable salt thereof in a physiologically acceptable solvent, and which has a pH of from 2.5 to 3.5. For solution formulations, various compounds of the present invention may be more soluble or stable for longer periods in solutions at a pH lower than 6. In one embodiment, the pH of the radiolabeled biomolecule should be in the range of 6.5-7 so that it is suitable for injection into an individual (e.g., a human). Further, acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide. In another embodiment, the diluent solution is at pH of between 10 and 12. In another embodiment, the pH of the combined formulation administered is greater than 5.0. In another embodiment, the pH of the combined formulation administered is between pH 5.0 and 7.0.

The invention also provides a process for producing a sterile solution with a pH of from 2.5 to 3.5 which process comprises dissolving the conjugate(s) as described herein or a pharmaceutically acceptable salt thereof in a pharmaceutically acceptable solvent. Where a pharmaceutically acceptable acid salt of the conjugate(s) as described herein is used the pH of the solution may be adjusted using a pharmaceutically acceptable base or basic solution adding a physiologically acceptable acid or buffer to adjust the pH within a desired range. The method may further comprise passing the resulting solution through a sterilizing filter.

In an embodiment, there may be the release of conjugates based upon pH-sensitivity. In an embodiment, one or more additional components such as co-solubilizing agents, tonicity adjustment agents, stabilizing agents and preservatives, for instance of the kind previously specified, may be added to the solution prior to passing the solution through the sterilizing filter.

In a variation, the present compounds/complexes can be used with other compounds/compositions/complexes that are used as immunotherapies or immune modulating therapies.

In a further variation, the present invention contemplates combination therapies in which the compounds of the present invention can be used in conjunction with cisplatin compounds. The efficacy of this combination therapy is likely to be enhanced because of the different mechanisms and modes of action that cisplatin compounds exhibit relative to the compounds of the present invention. It is also contemplated and therefore within the scope of the invention that other anti-neoplastic agents/compounds can be used in conjunction with the compounds/complexes of the present invention. The anti-neoplastic agents/compounds that can be used with the compounds of the present invention include cytotoxic compounds as well as non-cytotoxic compounds.

Examples include anti-tumor agents such as HERCEPTIN™ (trastuzumab), RITUXAN™ (rituximab), ZEVALIN™ (ibritumomab tiuxetan), LYMPHOCIDE™ (epratuzumab), GLEEVAC™ and BEXXAR™ (iodine 131 tositumomab), Neulasta, provenge, nivolumab, blinatumomab.

Other anti-neoplastic agents/compounds that can be used in conjunction with the compounds of the present invention include anti-angiogenic compounds such as ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto).

Other anti-angiogenic compounds/agents that can be used in conjunction with the compounds of the present invention include Campath, IL-8, B-FGF, Tek antagonists, anti-TWEAK agents (e.g., specifically binding antibodies or antigen binding regions, or soluble TWEAK receptor antagonists, ADAM distintegrin domain to antagonize the binding of integrin to its ligands, specifically binding anti-eph receptor and/or anti-ephrin antibodies or antigen binding regions, and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Other anti-angiogenic/anti-tumor agents that can be used in conjunction with the compounds of the present invention include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA); ilomastat, (Arriva, USA,); emaxanib, (Pfizer, USA,); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland); the ARGENT technology of Ariad, USA; YIGSR-Stealth, (Johnson & Johnson, USA); fibrinogen-E fragment, (BioActa, UK); the angiogenesis inhibitors of Trigen, UK; TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WVAX, USA); Benefin, (Lane Labs, USA); Tz-93, (Tsumura, Japan); TAN-1120, (Takeda, Japan); FR-111142, (Fujisawa, Japan); platelet factor 4, (RepliGen, USA); vascular endothelial growth factor antagonist, (Borean, Denmark); bevacizumab (pINN), (Genentech, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Children's Hospital, USA); ATN 161, (Attenuon, USA); ANGIOSTATIN, (Boston Children's Hospital, USA); 2-methoxyestradiol, (Boston Children's Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1 alpha inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Children's Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrugs, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pIN), (Genaera, USA); RPI 4610, (Sima, USA); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); anti-FAP agents such as 28H1 (Roche Pharmaceuticals, Switzerland) and, thrombospondin 1 inhibitor, (Allegheny Health, Education and Research Foundation, USA).

It is contemplated and therefore within the scope of the invention that the compounds, complexes and compositions of the present invention can be modified to target specific receptors or cancer cells or can be modified so that they can survive various in vivo environments. In a variation, the conjugates, compositions, and methods of the present invention can be used against solid tumors, cell lines, and cell line tissue that demonstrate upregulated nucleotide excision repair and other upregulated resistance mechanisms.

EXPERIMENTAL

An attempt to prepare $^{89}$Zr-DOTA using $^{89}$Zr-oxalate, ended unfavorably as there was no reaction. However, replacing $^{89}$Zr-oxalate with $^{89}$ZrCl$_4$ led to the synthesis of $^{89}$Zr-DOTA in quantitative yield, and with excellent radiochemical purity. More excitingly, $^{89}$Zr-DOTA was observed to be more stable to EDTA, DTPA and serum challenge than $^{89}$Zr-DFO (see Table 1), and $^{89}$Zr-DOTA exhibited a biodistribution that was superior to that of $^{89}$Zr-DFO in normal mice (FIG. 1). These data demonstrate that $^{89}$Zr-AMCs derived from $^{89}$ZrCl$_4$ yield $^{89}$Zr-complexes that can be superior to the "gold standard" $^{89}$Zr-DFO and dictate a systematic study of the coordination chemistry of AMCs with $^{89}$Zr.

TABLE 1

In vitro Stability comparison between $^{89}$Zr-DFO and $^{89}$Zr-DOTA. Data was compiled is after 1 h and 7 days using Radio-TLC. In all cases, the stability of $^{89}$Zr-DOTA is superior to $^{89}$Zr-DFO. FIG. 1 shows in vivo biodistribution of $^{89}$Zr-DOTA and $^{89}$Zr-DFO in selected tissues harvested from normal mice (n = 6/group). Both $^{89}$Zr-complexes experience rapid blood clearance. Less radioactivity was found to be in the liver, kidney and bone of animals injected with $^{89}$Zr-DOTA suggesting it is more stable in vivo than $^{89}$Zr-DFO.

| | $^{89}$Zr-DFO (n = 3) | | | | $^{89}$Zr-DOTA (n = 3) | | | |
|---|---|---|---|---|---|---|---|---|
| Time | 50 mM EDTA, pH 5.5 | 50 mM DTPA, pH 5.5 | 50 mM DTPA, pH 7.0 | Serum | 50 mM EDTA, pH 5.5 | 50 mM DTPA, pH 5.5 | 50 mM DTPA, pH 7.0 | Serum |
| 1 h | 6.3 ± 0.8% | 7.3 ± 0.8% | 90.3 ± 0.5% | 100% | 100% | 100% | 100% | 100% |
| 7 d | 0% | 0% | 40.6 ± 0.5% | 99.3 ± 0.1% | 100% | 100% | 100% | 100% |

The preliminary data show that AMCs can chelate Zr, and that $^{89}$Zr-DOTA is more stable than $^{89}$Zr-DFO in vitro and in vivo. It is believed that this stability is likely to occur across the structural spectrum of AMCs. The various AMCs will be systematically studied to confirm that these ligands possess these superior properties.

From Table 1, if $^{89}$Zr-DOTA was unstable as claimed by the prior art, transchelation to EDTA, DTPA or human serum should be observed. While this transchelation is observed with $^{89}$Zr-DFO, it is not observed with $^{89}$Zr-DOTA, not only contradicting claims made in in the prior art that this compound cannot be made, but also indicating greater stability of $^{89}$Zr-DOTA.

Figure 2:
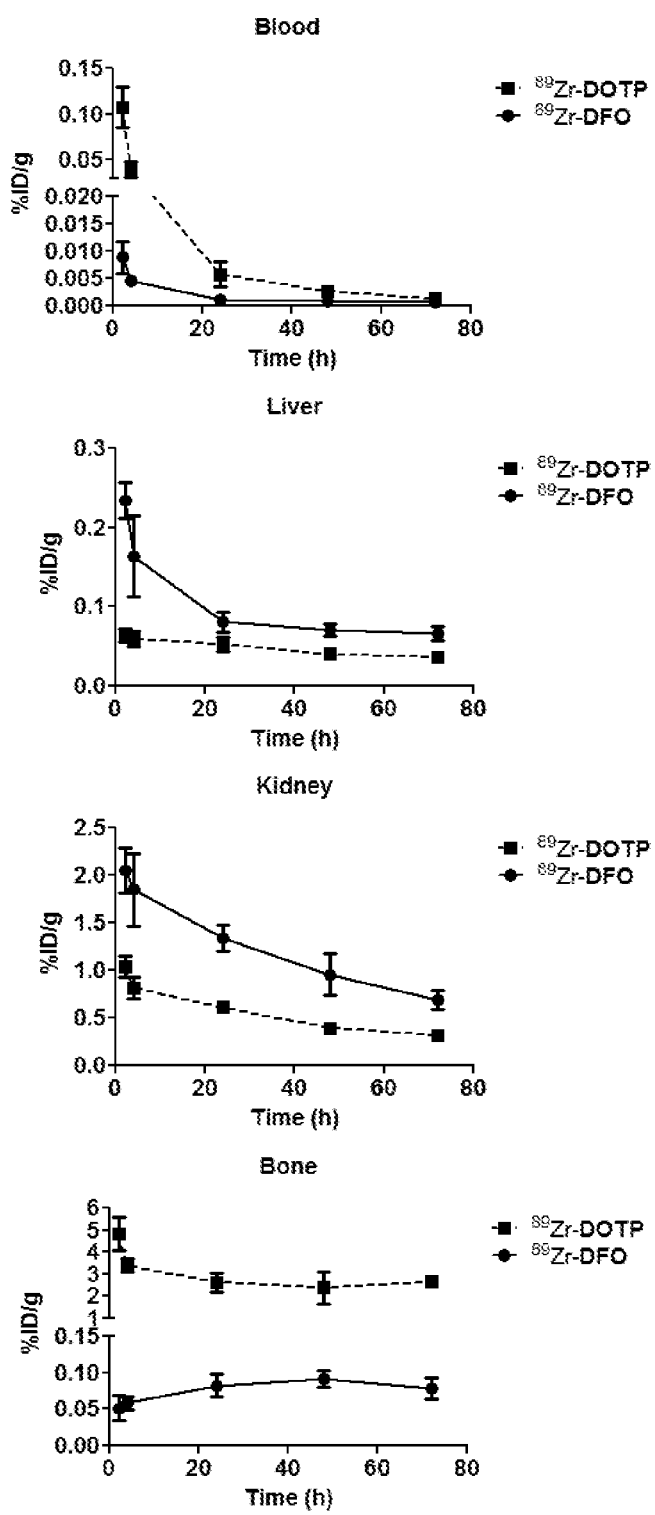
FIG. 2 shows in vivo biodistribution for $^{89}$Zr-DOTP and $^{89}$Zr-DFO in selected tissues (n=6/group). Both $^{89}$Zr-complexes are cleared from the blood by 72 h post-injection. Mice injected with $^{89}$Zr-DOTP retained less radioactivity in the liver and kidney. These are the major routes of excretion for $^{89}$Zr-complexes, and lower levels of radioactivity in these tissues suggest improved stability over $^{89}$Zr-DFO. Bone retention is higher for $^{89}$Zr-DOTP because of the phosphate groups on the DOTP ligand. This elevated bone retention is observed with all phosphate containing radiometal complexes, and does not indicate instability.
Figure 3:
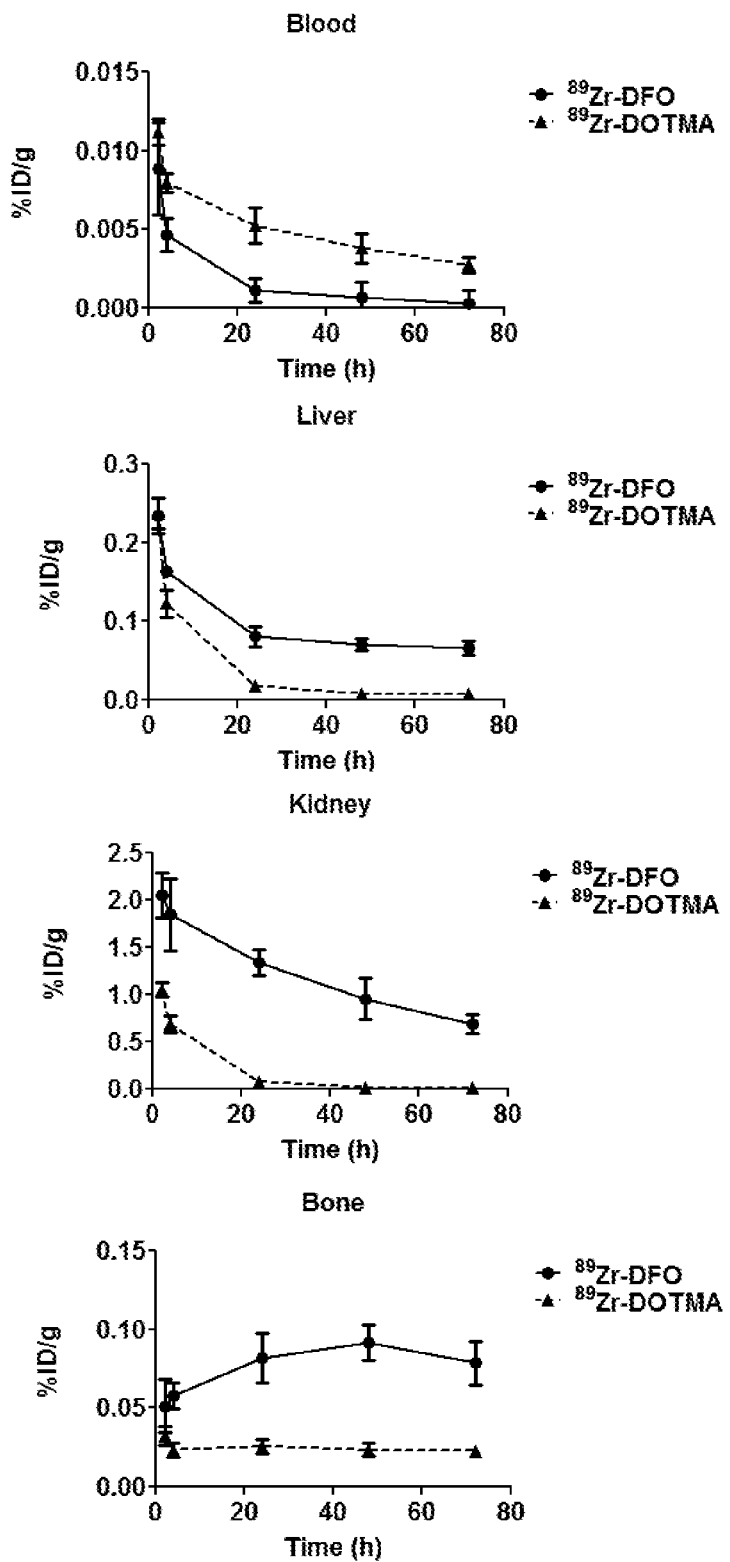
FIG. 3 shows in vivo biodistribution for $^{89}$Zr-DOTMA and $^{89}$Zr-DFO in selected tissues (n=6/group). Mice injected with $^{89}$Zr-DOTMA retained less radioactivity in the liver, kidney and bone, which are tissues where transchelated $^{89}$Zr would be retained if the $^{89}$Zr-complex was unstable in vivo. Lower levels of radioactivity in these tissues suggest improved stability over $^{89}$Zr-DFO.

Similarly, FIGS. 2 and 3 show $^{89}$Zr-DOTP and $^{89}$Zr-DOTMA show superior properties relative to $^{89}$Zr-DFO in selected tissues (n=6/group).

Table 2 shows various AMCs that can or are believed to be able to chelate Zr. These ligands and complexes will be characterized using FTIR, $^1$HNMR, $^{13}$CNMR, high resolution ESI-MS, and single crystal x-ray diffraction.

TABLE 2

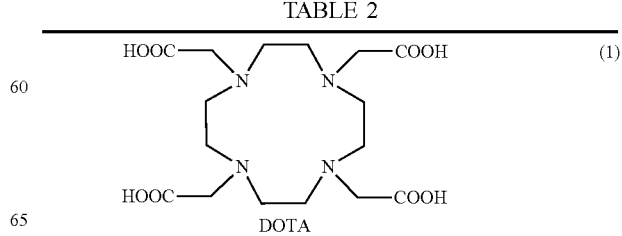

DOTA (1)

TABLE 2-continued

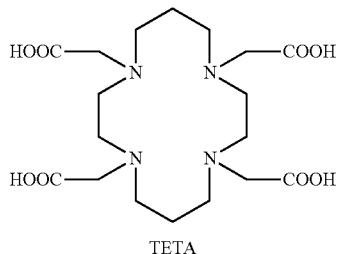 [SMILES: O=C(O)CN1CCCN(CC(=O)O)CCN(CC(=O)O)CCCN(CC(=O)O)CC1]
(2) TETA

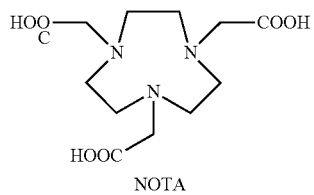
(3) NOTA

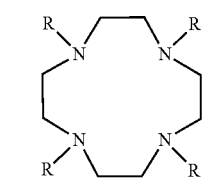
(4) R = H
(5) R = CH$_3$
(6) R = CH$_2$—CH$_3$
(7) R = CH$_2$—CH$_2$—CH$_3$

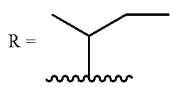
(8) R =

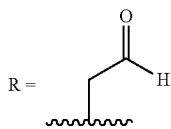
(9) R =

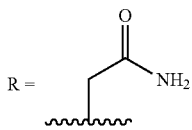
(10) R =

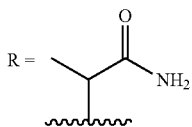 [SMILES: *C(C)C(N)=O]
(11) R =

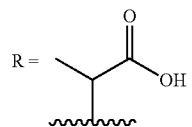 [SMILES: *C(C)C(=O)O]
(12) R =

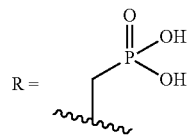 [SMILES: *CP(=O)(O)O]
(13) R =

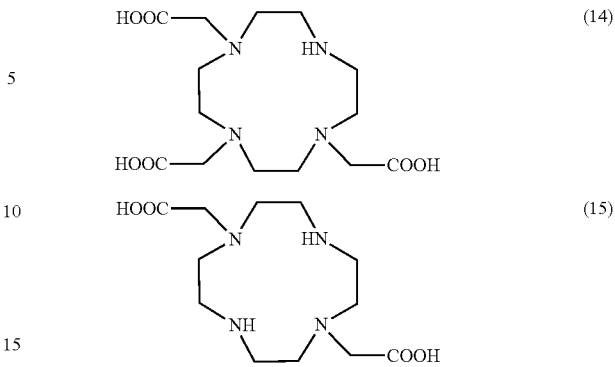
(14)

(15)

In Table 2, ligands 1-3 will provide insight into the relationship between the Zr-complex stability and macrocycle size, while ligands 4-15 will allow a determination of how $^{89}$Zr-complex stability is related to pendant arm number and composition.

Density Functional Theoretical (DFT) Calculations will be performed on a supercomputer. These calculations will be performed using Gaussian 09 suite of computer programs. All calculations will use the CEP121G basis set, B3LYP functional and the CPCM polarizable conductor-like solvent continuum model with Bondi. Previously, these settings have been used successfully by others to produce the most accurate results with respect to the modeling of Zr-DFO. Complex geometries will be completely optimized in all internal degrees of freedom while considering several different conformations of the ligands and complexes. All final structures will be reported as energy minimized solutions.

Potentiometry and Acid Decomplexation:

Potentiometric titrations (in triplicate) will be performed using a Metrohm 702S Mtitrion titration system running Metrohm Tinet software using known procedures. Briefly, complex titrations will be run by the addition of approximately 0.25 equivalents of Zr(IV) relative to free ligand. 200 equilibrium points will be collected in the pH range 2.00-12.00. The potentiometric data will be refined with Hyperquad software. The overall equilibrium (formation) constants $\beta_i^H$ and $\beta_{MmHhLl}$ will be defined as $\beta_{MmHhLl}=[M_mH_hL_l]/[M]_m[H]_h[L]_l$ and $\beta_{MH-1L}=\beta_{ML(OH)} \times K_w$ ($K_w=[H+][OH-]=10^{-13.778}$), while stepwise equilibrium constants are given by $K_{MmHhLl}=[M_mH_hL_l]/[M_mH_{h-1}L_l][H]$ and correspond to the difference in log units between overall constants of sequentially protonated (or hydroxide) species.

Acid-decomplexation studies (in triplicate) will be performed under pseudo first-order conditions using $^{Nat}$Zr-AMCs (2.2 mmol) in 5 M or 12 M HCl at 50° C. and 90° C. Changes in the absorption maxima will be monitored using a Shimadzu UV-Vis spectrophotometer (UV-1650PC) in thermostated cells. The decreasing absorbance at the $\lambda_{max}$ of each $^{Nat}$Zr-AMCs will be used to monitor decomplexation, and average half-live values will be calculated from the slopes of linear ln(absorbance) vs. time plots.

Radiochemistry, Lipophilicity, In Vitro Stability:

Each $^{89}$Zr-complex will be prepared in high radiochemical purity and a specific activity ($A_s$) of 1 GBq/µmol with $^{89}$ZrCl$_4$ using a modification of known methods. This value represents the average $A_s$ for $^{89}$Zr-DOTA and $^{89}$Zr-DFO, and this value is comparable to the $A_s$ reported for other $^{89}$Zr-complexes. $^{89}$Zr ($t_{1/2}$=78.4 h, $\beta^+$: 22.8%, $E_{\beta+max}$=901 keV; EC: 77%, E$\gamma$=909 keV) will be purchased from Washington University School of Medicine. Radiochemical purity will be monitored using a Waters HPLC system equipped with a Waters 2998 photodiode array detector, and a 105/s radioactivity detector (Carroll Ramsey, Inc., Berkeley, Calif.).

Lipophilicity (Log P) will be determined using the water:octanol method. Briefly, the water:octanol (1:1) solution containing the $^{89}$Zr-complex (0.19 MBq) will be vortexed (5 min) and then centrifuged (5 minutes at 17,000 rpm). After separation, aliquots from each layer will be counted separately in the gamma counter, and Log P will be calculated as the ratio of counts in the octanol fraction to counts in the aqueous fraction. In vitro stability will be determined by incubating each $^{89}$Zr complex at 37° C. in the presence 500 μL of DTPA (50 mM, pH 7 or pH 5), 500 μL of EDTA (50 mM, pH 7 or pH 5), or 500 μL of human serum (at 37° C.). The different pH environments will be meant to reflect the pH environments in normal blood (pH 7) or the lysosome (pH 5). Samples will be analyzed over the course of 7 days using radio-TLC and radio-HPLC.

In Vivo Biodistribution and Small Animal PET/CT Imaging:

NIH Swiss mice (n=6/time point) will be injected with the $^{89}$Zr-AMC (0.56 MBq (15 μCi)), and then sacrificed at 1, 4, 24, 48 and 72 h post-injection (p.i.). Organs of interest will be removed, weighed and counted on a gamma counter. Percent injected dose per gram (% ID/g) and percent injected dose per organ (% ID/organ) will be counted and compared to a weighed, counted standard for all groups.

Small animal PET/CT imaging will be conducted on the $^{89}$Zr-AMCs identified from studies described above and in vivo biodistribution studies. NIH Swiss mice (n=6/cohort) will be injected with either $^{89}$ZrCl$_4$, $^{89}$Zr-DFO (11 MBq (300 μCi)) or $^{89}$Zr-AMC and imaged using 1 h dynamic scanning followed by static imaging at 4, 24, 48 h and 72 h p.i. PET images will be reconstructed using the maximum a posteriori (MAP) algorithm, since it provides significantly improved resolution when compared to standard OSEM reconstruction and improves the recovery coefficient; radioactivity quantification in a particular region of interest to more closely reflect its true amount of radioactivity. All PET images will be co-registered with CT, to (a) allow more accurate selection of regions of interest to correspond with anatomy described by CT, and (b) reduce inaccuracies that result from partial volume effects, which can result in falsely low standard uptake values (SUVs) during data analysis. SUVs and the corresponding % ID/g will be determined from the co-registered PET/CT images using the formula SUV=[nCi/cc×animal weight/injected dose], and correlated to the biodistribution data.

Metabolism Assays:

The $^{89}$Zr-AMCs (5 mCi/mouse; 0.1 mmol/kg) will be injected into NIH Swiss mice and the metabolism of the $^{89}$Zr-AMC will be determined at 1, 4, 24, 48 and 72 h post-injection. Animals will be kept in metabolism cages so that urine and feces can be collected at each time point and the associated radioactivity will be measured by gamma counting to ensure mass balance. Samples from selected tissues and blood will be placed in a suitable extraction buffer such as 20% HEPES in ethanol. Tissues will then undergo mechanical homogenization and cellular disruption using an OmniTH® (Kennesaw, Ga.) tissue homogenizer and an Omni® (Kennesaw, Ga.) sonic-ruptor ultrasonic cell disruptor, respectively. All samples will be centrifuged (23,000 g) to remove large particulates. The $^{89}$Zr content of the pellet and supernatant will be determined using a gamma counter. The activity in the supernatant will be subdivided into low and high molecular weight metabolites using a Centricon® (YM-3) filter (Sigma Aldrich St. Louis Mo.), which has a molecular weight cutoff of 3 kDa. Liquid samples will be concentrated and further analyzed by size exclusion chromatography, or HPLC to determine the amount of high and low molecular weight species. A control experiment that involves the direct addition of the $^{89}$Zr-chelate to the excised tissue prior to homogenization, will be performed for every experiment to establish the extraction efficiency (extraction=cpm$_{sup}$/cpm$_{pellet+sup}$; cpm$_{sup}$ is the counts per minute in the supernatant and cpm$_{pellet+sup}$ is the counts per minute in the pellet and supernatant.).

The low molecular weight fraction will be analyzed using a Bioscan AR2000 radio-TLC scanner and radio-HPLC using a Waters 600E chromatography system (Milford, Mass.) equipped with a Waters 2487 dual wavelength detector and an Ortec Model 661 radioactivity detector (EG&G Instruments, Oak Ridge, Tenn.). Migration distance and elution times will be compared to the injected $^{89}$Zr-AMC, to determine if any of the species are actually the intact radiotracers. The amount of free $^{89}$Zr in various samples will be assessed by adding excess free chelate to the samples and measuring the formation of $^{89}$Zr-chelates. Additionally, HPLC in combination with mass spectrometry analysis of decayed samples will enable the determination of MW of metabolites as previously demonstrated.

Two possibilities for high molecular weight $^{89}$Zr components will be studied. The first is that the $^{89}$Zr will be protein bound. The number of proteins that bind $^{89}$Zr will be tested by gel filtration using size-exclusion chromatography with a Water's chromatography system that was described above, and configured with Superose 12 and Superose 6 size exclusion chromatography columns (GE Life Sciences). This will provide an approximate molecular weight of each species and allow comparison to the known molecular weights of $^{89}$Zr-chelates binding protein standards (Sigma-Aldrich), which will be incubated with the $^{89}$Zr-chelate and analyzed using size-exclusion chromatography. Retention times of the standards and unknown samples will be compared, and the percentage of each component will be determined from the integrated area under each curve. The percentage of authentic intact compound (% AI=% P×% I×[1+% pellet/% super)×% E) will be determined. Here, % P is the purity of the injectate determined from the HPLC; % I=intact $^{89}$Zr-chelate determined by integration of the HPLC chromatogram; % pellet/% super is the ratio of the radioactivity in the pellet and supernatant of the organ blank and % E is the extraction efficiency of the harvested organ after the injection of the $^{89}$Zr-chelate. The strength and stability of the $^{89}$Zr-protein bond will be assessed by challenging with excess free chelate. Briefly, buffered solutions (100 μl) of the chelate will be prepared over a concentration range that will increase 50 fold. Each solution will be added to a separate aliquot of the fraction containing the $^{89}$Zr bound protein. After incubation, size exclusion chromatography will be conducted as previously described to determine the extent of transchelation. If this analysis identifies particular proteins, we will assess what fraction of the $^{89}$Zr activity can be precipitated or otherwise removed using specific antibodies for those proteins if they are available. The second possibility for the high molecular weight $^{89}$Zr component is that it represents an insoluble precipitate. An insoluble precipitate will not be susceptible to digestion with proteases or other hydrolytic enzymes.

Comparison of Antibody Linking Using the Oxalate and Chloride Derivatives of $^{89}$Zr $^{89}$Zr-DFO-trastuzumab (TmAb) was prepared using $^{89}$Zr—OX as previously described or using $^{89}$ZrCl$_4$ in a newly developed synthetic method. Trastuzumab was chosen because it and its binding to the HER2/neu receptor have been characterized extensively in the literature. Furthermore, $^{89}$Zr-trastuzumab is currently being evaluated in more than 30 clinical trials, which makes it an appropriate model for evaluating the radiosynthesis strategy. Experimental parameters including time, temperature, buffer and amount of mAb used per radiolabeling reaction were evaluated in order to determine if $^{89}$ZrCl$_4$ had any effect on the synthesis of clinically relevant doses of $^{89}$Zr-DFO-TmAb. The results of these studies are summarized in Table 3.

TABLE 3

$^{89}$Zr-DFO-Trastuzumab preparation comparison using either $^{89}$Zr-OX or $^{89}$ZrCl$_4$

| | $^{89}$Zr-DFO-Trastuzumab (n = 5) | |
|---|---|---|
| Radiolabeling Condition | $^{89}$Zr(Ox)$_2$ | $^{89}$ZrCl$_4$ |
| Temperature | 21° C. | 21° C. |
| Time | 1 h 45 min | 15 min |
| Radio incorporation Yield | >85% | >99% |
| Purification | PD-10 Column | Not required |
| Radio labeling Yield | >80% | >98% |
| Radiochemical purity | >95% | >99.5% |
| Specific activity | 49 ± 5 MBq/mg | 235 ± 20 MBq/mg |

The advantages of the present invention show that $^{89}$Zr-DFO-Trastuzumab was synthesized with exceptional increases in purity, yield and specific activity (A$_s$) when prepared with $^{89}$ZrCl$_4$. Furthermore, reaction time is decreased by 86%, and purification via PD-10 column is eliminated, which simplifies radiopharmaceutical production.

The Cl— ion was tested to see if it acted in a detrimental way during synthesis of $^{89}$Zr-mAbs using $^{89}$ZrCl$_4$. An initial test was done to test this in vitro using Lindmo analysis, which examines immunoreactive fraction (IR), and antibody affinity (K$_a$), and the HER2+ human lung cancer cell line 2170. During the course of the investigations, no evidence of these detrimental effects was found. No appreciable difference in immunoreactivity or affinity was observed, and suggests that $^{89}$Zr-DFO-trastuzumab performed as expected regardless of the preparative route (see Table 4).

TABLE 4

Lindmo analysis conducted in HER2+ 2170 human lung cancer cells comparing the in vitro performance of $^{89}$Zr-DFO-Trastuzumab, which was prepared by $^{89}$Zr-oxalate or $^{89}$Zr-chloride.

| | $^{89}$Zr(Ox)$_2$ | $^{89}$ZrCl$_4$ |
|---|---|---|
| Immunoreactivity | 1.02 | 0.91 |
| K$_a$ | 2.15 × 10$^8$M$^{-1}$ | 2.43 × 10$^8$M$^{-1}$ |
| B$_{max}$ | 1.29 × 10$^8$ | 1.34 × 10$^8$ |
| K$_d$ | 4.6 × 10$^{-9}$ (4.6 nM) | 4.11 × 10$^{-9}$ (4.11 nM) |
| | | Reported K$_d$ is 5 nM |

Figure 10:
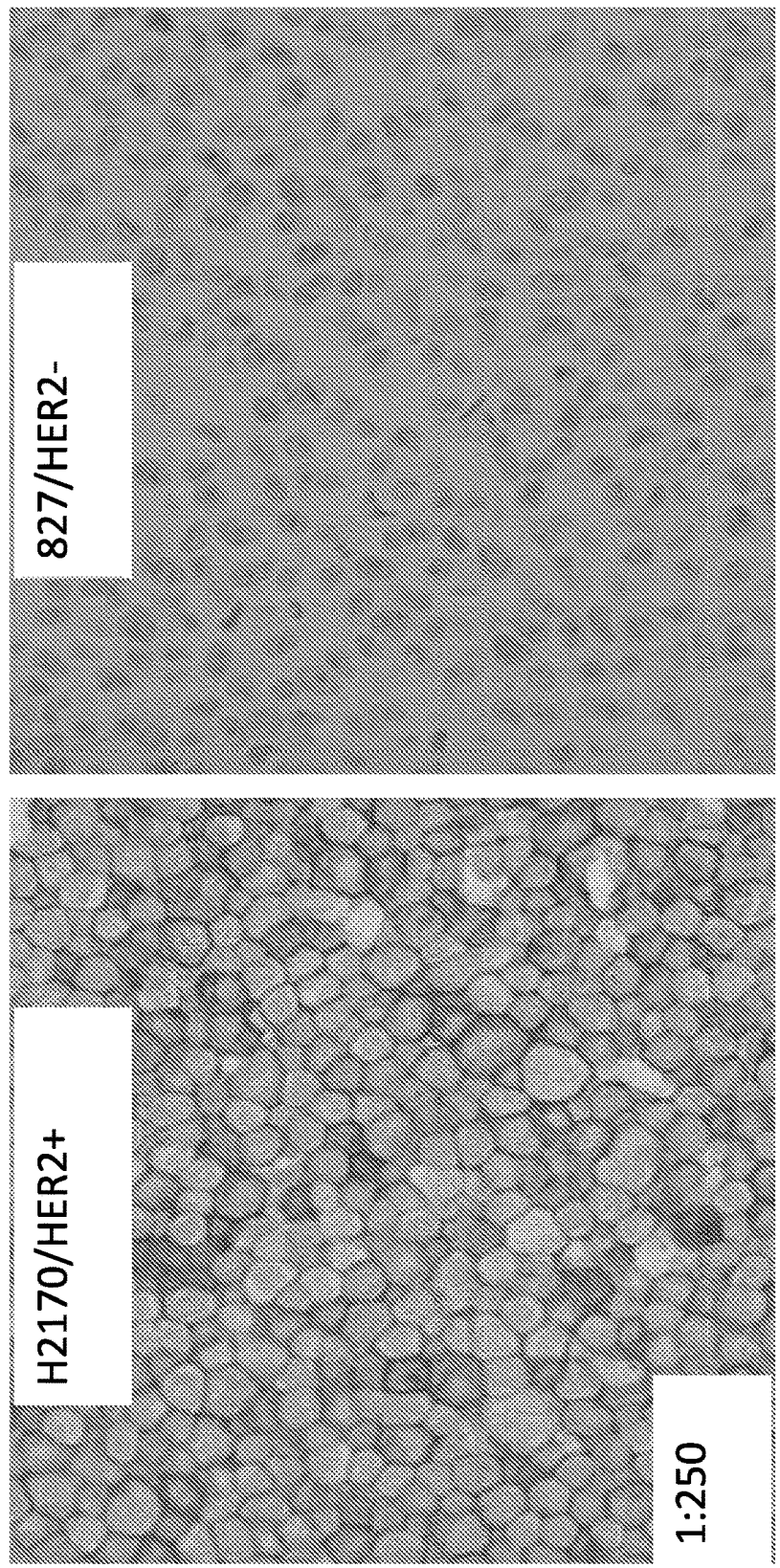
FIG. 10 shows histological staining of 2170 and 827 human lung cancer cells. Staining with anti-HER2 antibody confirms that the 2170 cells are HER2$^+$ and the 8278 cells are HER2$^-$.
Figure 11:
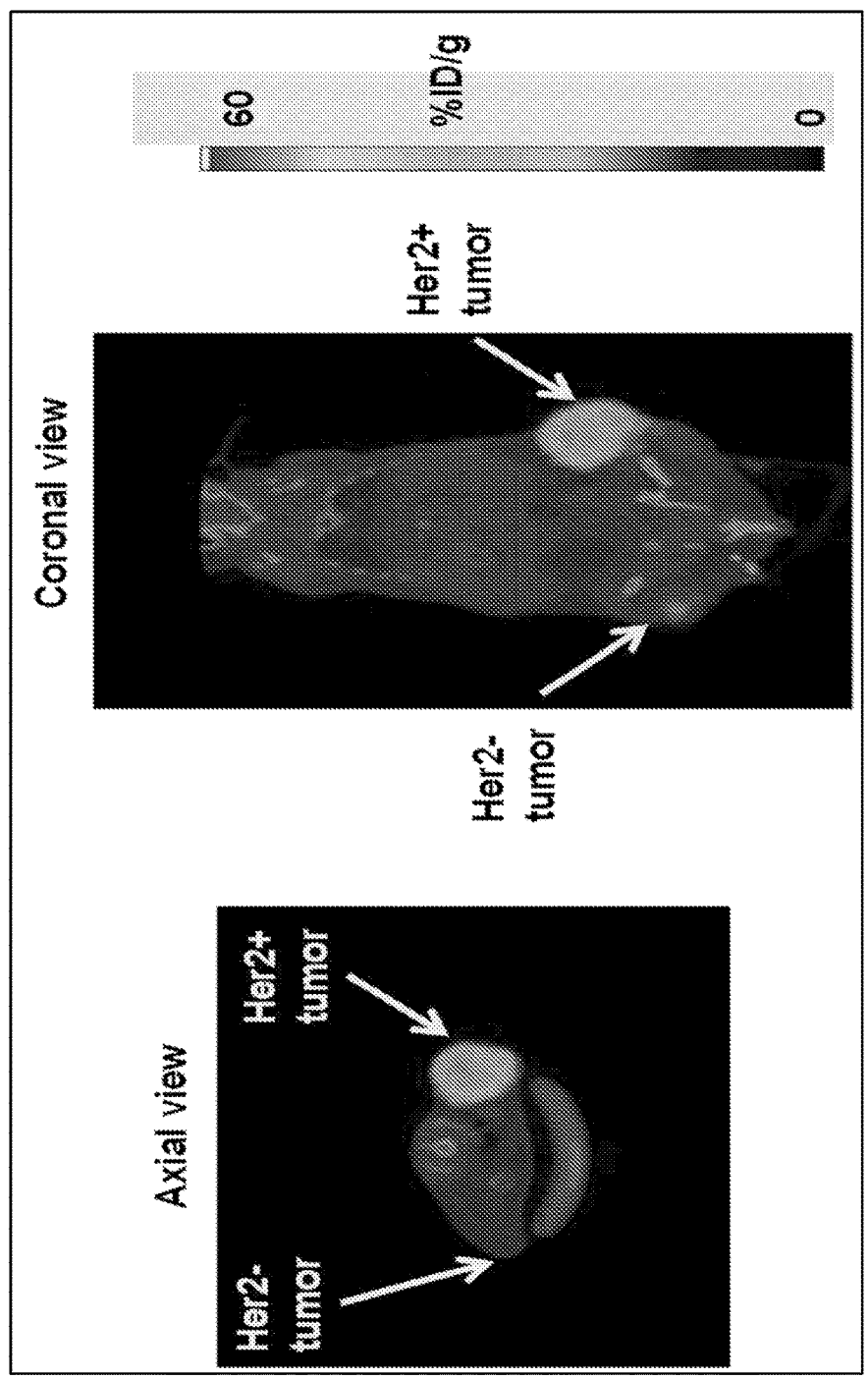
FIG. 11 shows PET imaging of HER2$^{+/-}$ tumors using $^{89}$Zr-DFO-Trastuzumab prepared with $^{89}$ZrCl$_4$. The use of $^{89}$ZrCl$_4$ does not hinder antibody function in vivo. Images taken at 144 h post-injection.

To further prove that $^{89}$Zr-immuno-PET agents prepared with $^{89}$ZrCl$_4$ are still functional radiopharmaceuticals, small animal PET/CT studies were undertaken in nude mice bearing human lung cancer tumors in contralateral flanks. Tumors were derived from the HER2$^+$ 2170 cell line and the 827 human lung cancer tumor cell line, which is devoid of the HER2 receptor (see FIG. 10). Animals were imaged from 24-144 hours. After the 144 h time point, animals were euthanized; tumor and tissues were removed to evaluate radioactivity retention through post-PET imaging biodistribution analysis. A representative image is found in FIG. 11.

Figure 12:
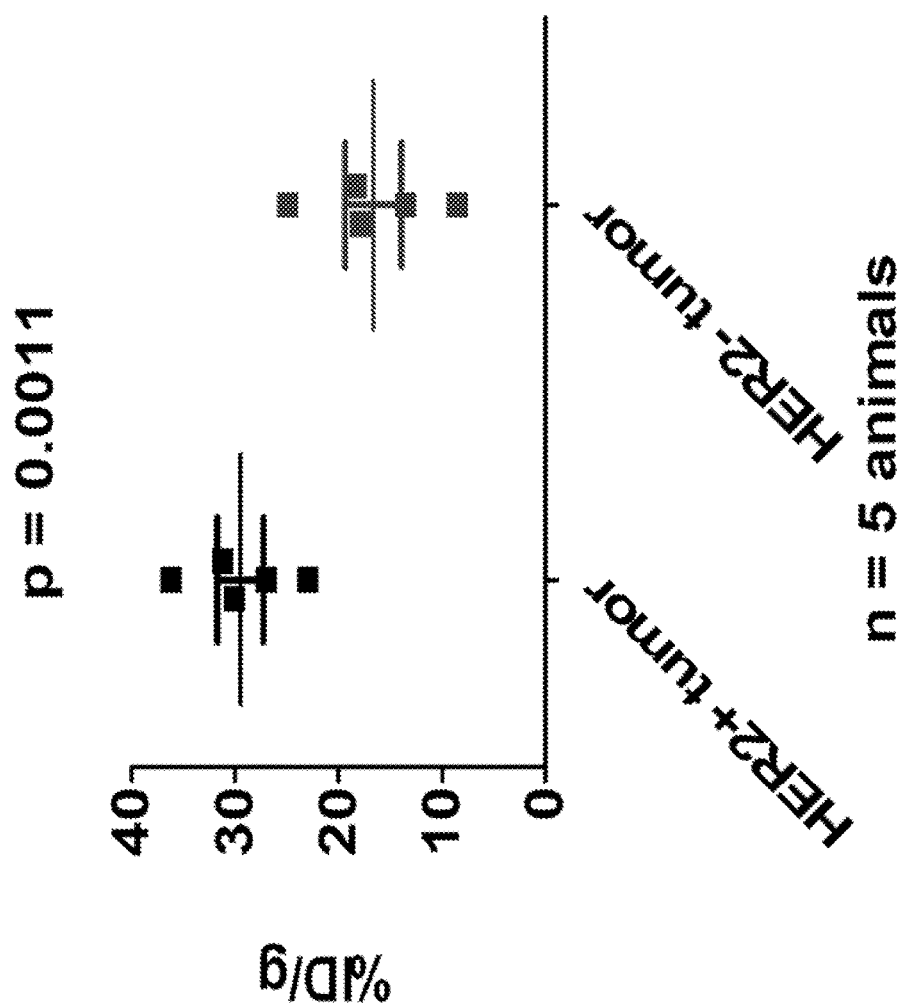
FIG. 12 shows tumor retention of radioactivity at 144 hours. Analysis based upon post-PET biodistribution. Effective targeting of the HER2+ tumor is observed.

The quantified radioactivity in tumors can be found in FIG. 12, while a complete biodistribution of all tissues at 144 h post-injection can be found in Table 5.

TABLE 5

Complete post-PET biodistribution studies in animals receiving $^{89}$Zr-DFO-Trastuzumab that was prepared with $^{89}$ZrCl$_4$.

| | $^{89}$Zr-Df-Bz-Trastuzumab, 144 h | |
|---|---|---|
| Tissue/Organ | % ID/g | % ID/organ |
| Blood | 6.50 ± 1.31 | 10.52 ± 2.41 |
| Heart | 1.48 ± 0.22 | 0.13 ± 0.03 |
| Lung | 4.34 ± 0.52 | 0.46 ± 0.09 |
| Liver | 4.20 ± 0.28 | 3.99 ± 0.31 |
| SMI + contents | 0.80 ± 0.11 | 0.96 ± 0.18 |
| LGI + contents | 1.15 ± 0.09 | 0.76 ± 0.07 |
| Kidney | 4.56 ± 0.27 | 1.30 ± 0.16 |
| Spleen | 8.31 ± 0.83 | 0.26 ± 0.02 |
| Pancreas | 0.78 ± 0.09 | 0.07 ± 0.01 |
| Stomach | 0.55 ± 0.27 | 0.23 ± 0.05 |
| Muscle | 0.46 ± 0.10 | 0.78 ± 1.64 |
| Fat | 0.66 ± 0.18 | 5.17 ± 3.12 |
| Bone | 8.31 ± 0.52 | 0.27 ± 0.02 |
| Tumor (+) | 29.50 ± 4.93 | 10.08 ± 2.22 |
| Tumor (−) | 16.67 ± 6.07 | 3.00 ± 1.14 |
| Tail | 1.65 ± 0.17 | 0.89 ± 0.10 |
| Std | 1.00 ± 0.02 | 1.01 ± 0.01 |

As expected, the HER2$^+$ tumors retained significantly more radioactivity than did the HER2$^-$ tumors and the amount of radioactivity observed in the HER2$^+$ tumors is similar to that reported in the literature. Furthermore, bone retention was observed to be 8.31±0.52%, which is also reasonable when compared to the bone retention of radioactivity in mice injected with $^{89}$Zr-DFO-trastuzumab or other $^{89}$Zr-labeled mAbs reported in the literature. This data further suggests that contrary to scientific consensus, the use of $^{89}$ZrCl$_4$ or Cl$^-$ ion containing buffer does not damage the $^{89}$Zr-labeled antibody to an extent that would hinder its function in vitro or in vivo.

The optimized radiochemistry conditions for preparing $^{89}$Zr complexes with $^{89}$ZrCl$_4$ are given in table 6

TABLE 6

Summary of optimized radiochemistry conditions to prepare $^{89}$Zr-complexes with $^{89}$ZrCl$_4$

| Radiochemistry conditions | Ligand (n = 50) | | | |
|---|---|---|---|---|
| | DOTA | DOTP | DOTAM | DFO |
| Quantity (µg) | 10 | 10 | 10 | 10 |
| Temperature (° C.) | 90 | 90 | 90 | 24 |
| Reaction time (min) | 45 | 45 | 45 | 15 |
| Reaction buffer | 0.5M HEPES | — | 1M HEPES | — |
| Reaction pH | 6.9-7.2 | 7.0-7.5 | 6.9-7.2 | 7.0-7.5 |
| Radiochemical yield (%) | 100 | 100 | 100 | 100 |
| Specific activity (A$_s$; MBq µmol$^{-1}$) | 1010 ± 8 | 1008 ± 10 | 989 ± 10 | 1005 ± 10 |

Statistical Analysis

Although not a new imaging technique, there is limited consensus when estimating statistical significance for small animal PET studies. For this well-controlled model, the outcome is radioactivity accumulation in the blood, liver, kidney and bone after 72 hours. Pilot data suggests that cohorts receiving $^{89}$Zr-DOTA will experience at least a 10% reduction in radioactivity accumulation at 72 hours in the liver, kidney, and bone and an equivalent accumulation in the blood. For this well-controlled model, there will be 3 cohorts (n=6 mice/cohort); 2 control cohorts ($^{89}$ZrCl$_4$ and $^{89}$Zr-DFO) will be used to compare against the cohort receiving $^{89}$Zr-DOTA or the best $^{89}$Zr-AMC identified from the in vitro studies as described above. Using a two sided t-test, type 1 error rate of 0.05, and 90% power, a difference will be able to be detected of approximately two standard deviations. For accumulation in the liver, kidney, and bone this would translate to a difference of at least 0.005% ID/g; assuming a standard deviation of 0.0022. Blood accumulation is expected to be similar in all cohorts, but with an assumed standard deviation of 0.0005, a difference of at least 0.001% ID/g should be detectable. Monitoring the radioactivity at every time point, exploratory analysis will be conducted using a repeated measure generalized linear model to evaluate differences throughout the full 72 hours.

Structure of Zr-DOTA

Figure 14:
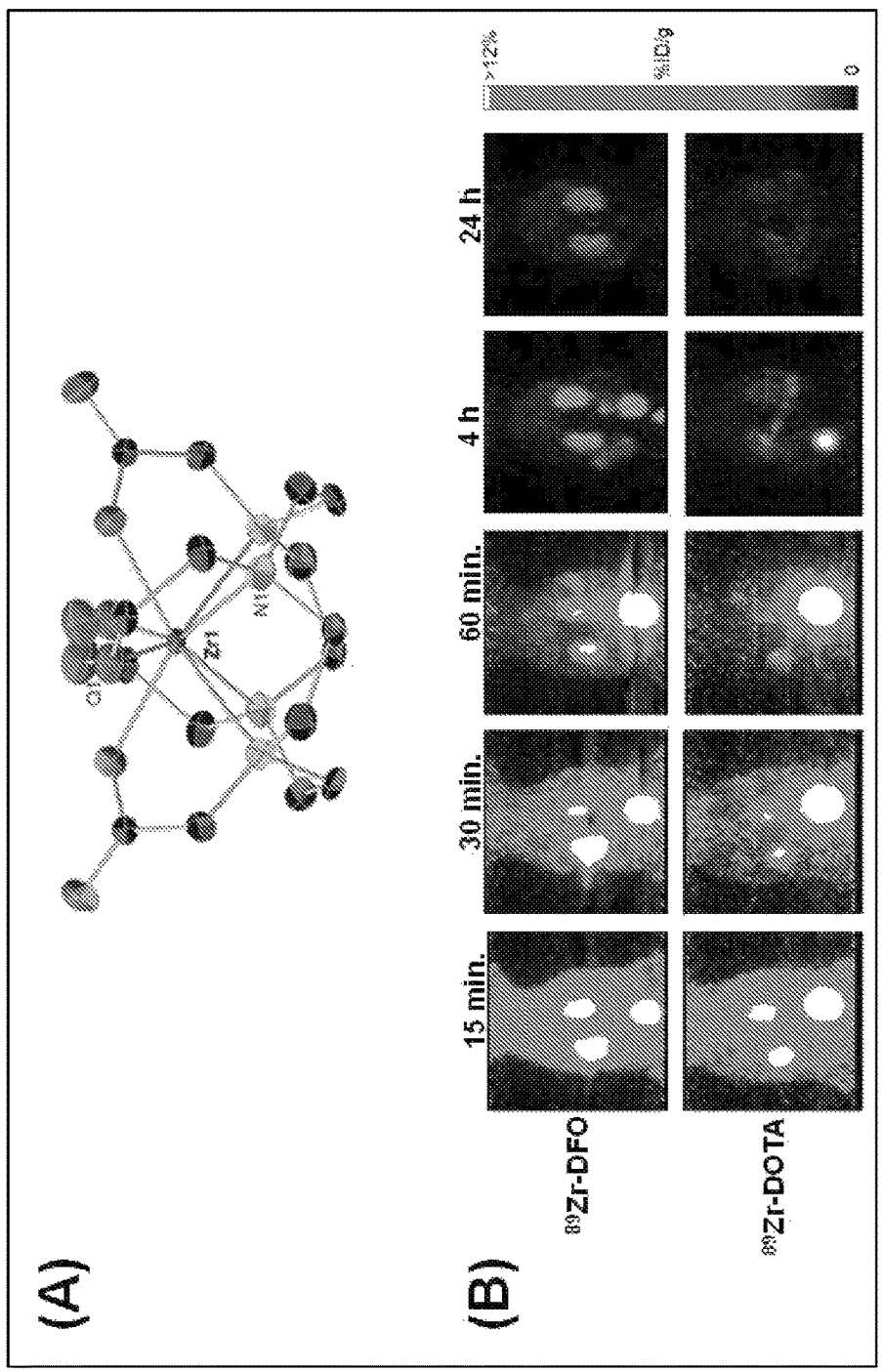
FIG. 14 shows a crystal molecular structure of Zr-DOTA in FIG. 14 (A) and maximum intensity projection images comparing the clearance of $^{89}$Zr-DFO and $^{89}$Zr-DOTA in normal mice in FIG. 14(B).
Figure 15:
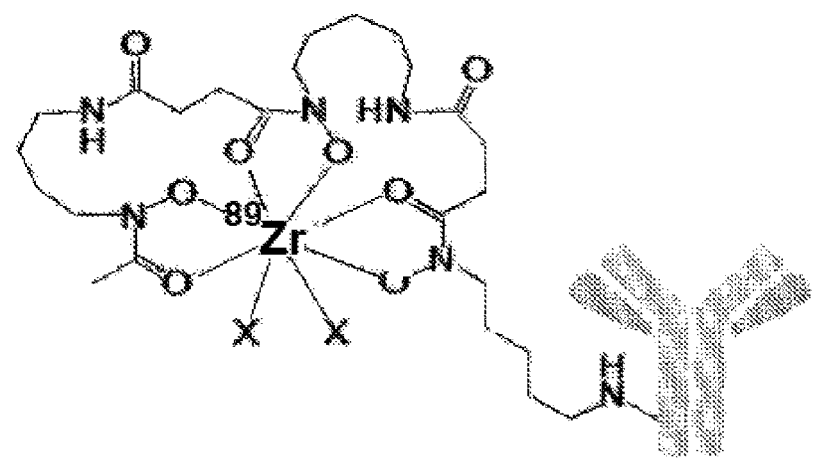

Single crystal analysis of $^{Nat}$Zr-DOTA revealed an octa-coordinate complex demonstrates C4 symmetry with square anti-prism geometry and a tetragonal (P4cc) space group. The Zr$^{4+}$ ion sits above the macrocyclic cavity. Radiochemistry studies revealed $^{89}$Zr-DOTA to be extraordinarily inert to exogenous ligand and metal challenge. Furthermore, biodistribution and small animal PET imaging revealed rapid systemic clearance and low tissue retention, which suggests this radiometal complex is highly stable in vivo. The crystal molecular structure of Zr-DOTA is shown in FIG. 14 (A) and the maximum intensity projection images comparing the clearance of $^{89}$Zr-DFO and $^{89}$Zr-DOTA in normal mice is shown in FIG. 14(B). It was shown that that $^{89}$Zr-DOTA is superior to $^{89}$Zr-DFO, the only chelating ligand to be used clinically in $^{89}$Zr radiopharmaceutical applications.

It was believed that tetraazamacrocycles would be good $^{89}$Zr chelators and could be used in $^{89}$Zr-radiopharmaceutical development because 1) they demonstrate enhanced stability over acyclic ligands due to the macrocyclic effect; 2) various functional groups can be introduced into the macrocycle's backbone or pendant arms to modulate the ligand's stereo- and coordination chemistry; 3) bifunctional chelators derived from these ligands allow them to be conjugated to various peptides, proteins, and antibodies; and 4) they have been used successfully in a number of radiopharmaceutical applications and clinical trials.

During initial syntheses, poor reactivity was observed when the respective ligands were reacted with zirconium oxalate (Zr—OX). Thus, either Zr(IV) acetylacetonate (AcAc) or ZrCl$_4$ was used as starting materials in subsequent synthetic strategies. Accordingly, nonradioactive $^{Nat}$Zr-DOTA and $^{Nat}$Zr-DOTAM complexes were prepared by reacting the analogous ligands (1 equiv. each) with a slight excess of ZrAcAc or ZrCl$_4$ (1.1 equiv. each) in methanol for 3 h, with 94% and 91% yield, respectively. A $^{Nat}$Zr-DOTP complex was prepared by reacting ligand DOTP (1 equiv.) with a slight excess of ZrCl$_4$ (1.1 equiv.) in water under neutral conditions for 2 h, with 92% yield. All $^{Nat}$Zr-complexes were fully characterized by HPLC, NMR spectroscopy, and HR-MS analyses.

$^{Nat}$Zr-DOTA and $^{Nat}$Zr-DOTP eluted as a single peak with a purity ≥99.9% and retention time (RT) of 6.30 and 6.42 minutes, respectively, which was about 1 minute longer than the free ligands. $^1$H- and $^{13}$C-NMR of Zr-DOTA were done in D$_2$O; the resulting spectra agreed well with previous corresponding observations. Ethylenic protons of the aza-macrocyclic ring appeared to split in a doublet of triplets (δ 2.99 and 2.38) and doublet of doublets (δ 2.58 and 2.29), whereas methylene protons of acetate groups were doublets at δ 3.40 and 3.15 with a coupling constant of 17.6 Hz. Zr-DOTAM had a very similar $^1$H, $^{13}$C-NMR pattern, which was expected due to the structural similarity of both the complexes. For Zr-DOTP, the methylene (—CH$_2$) groups located on the phosphate pendant arms appeared as two doublets of triplets (δ 4.10 and 3.72), whereas azamacrocyclic ring protons appeared at δ 3.35 as a doublet of triplets and at δ 2.49 as multiplets. ESI-HR-MS analysis of $^{Nat}$Zr-DOTA, $^{Nat}$Zr-DOTP and $^{Nat}$Zr-DOTAM complexes confirmed the 1:1 binding of Zr$^{4+}$ with the respective ligands. Clear, colorless, needle-shaped crystals of each complex could be obtained by the slow evaporation of saturated aqueous solutions at room temperature. However, only Zr-DOTA crystals were suitable for X-ray structure determination.

Previously, others had attempted to determine the structure of Zr-DOTA using single crystal x-ray diffraction, but limited solubility hindered a definitive structural analysis, and a definitive structure was never reported. In the present invention, single crystal x-ray diffraction revealed 2 crystallographically-independent Zr centers in the asymmetric unit, one of which was disordered and could not be completely resolved. The ordered structure is depicted in FIG. 14(A), and complete crystallographic parameters, data collection and refinement information was gathered.

All four macrocycle nitrogen atoms and acetate pendant arms participate in Zr$^{4+}$ ion coordination to form an octa-coordinate complex with square anti-prismatic geometry. This geometry is not unusual, since Zr-tetraazamacrocycle complexes can accommodate different geometries, which are dictated by the additional ligands that occupy the coordination sites not occupied by the nitrogen atoms of the macrocycle. The Zr$^{4+}$ ion sits above the plane of the macrocycle. The perpendicular distance from the metal center to the plane described by the 4 acetate-containing pendant arms of the macrocycle is 1.004(3) Å, and the perpendicular distance from the metal center to the plane described by the 4 nitrogens of the macrocycle is 1.310(4) Å. The DOTA ligand displays a saddle-like conformation similar to that of metal-dibenzotetramethytetraaza[14]annulene complexes previously described by others. This conformation is most pronounced with metal complexes demonstrating d$^0$ electron configurations. The average Zr-ligand bond lengths and bond angles are comparable to those observed in structurally characterized Zr complexes containing hydroxamate, phenoxyamine, salophen or cyclam ligands. Although the Zr$^{4+}$ ion is not within the macrocyclic cavity, it can still form an octa-coordinate complex. This suggests that the latter criterion may be the key in rationalizing structure and qualities of stability, in contrast to the literature on other radiometal complexes.

After completing synthesis and characterization of the reference complexes, an attempt was made to radiolabel each ligand using $^{89}$Zr—OX and procedures established for preparation of $^{89}$Zr-DFO[18]. Radiochemical yields were poor; even after incubating each reaction for 2 hours at 99° C., the radiochemical yields of $^{89}$Zr-DOTA, $^{89}$Zr-DOTP, and $^{89}$Zr-DOTAM were only 65%, 70%, and 9%, respectively. Thus, a switch was made using $^{89}$ZrCl$_4$ for quantitative radiolabeling, which was produced in high radionuclidic and radiochemical purity (>99.9%) from $^{89}$Zr—OX, using a procedure modified from the literature. Using $^{89}$ZrCl$_4$, all radiochemical synthesis conditions were evaluated including buffer, chelator concentration, temperature and reaction time; optimized conditions and are presented in Table 6.

DOTA, DOTAM and DOTP were quantitatively radiolabeled within 45 min at 90° C. The radiochemical yield and purity of all $^{89}$Zr complexes were confirmed by radio-TLC and radio-HPLC. The specific activity ($A_s$) for each radiometal complex is in good agreement with the $A_s$ of other $^{89}$Zr-complexes reported in the literature.

Since tetraazamacrocycles have been considered poor $^{89}$Zr chelators, the in vitro stability of $^{89}$Zr-DOTA, $^{89}$Zr-DOTAM, and $^{89}$Zr-DOTP was evaluated by challenging them with excess EDTA, high concentrations of biologically relevant metal ions, or human serum proteins. $^{89}$Zr-DOTA did not experience transchelation, with a 100-, 500-, and 1000-fold excess of EDTA at pH 5 or pH 7 over 7 days. In contrast, $^{89}$Zr-DFO completely lost metal ions after 3 h, when the radio metal complex was exposed to a 1000-fold excess of EDTA. Based upon our EDTA challenge studies, the order of $^{89}$Zr complex stability can be described as $^{89}$Zr-DOTA>>$^{89}$Zr-DOTP>$^{89}$Zr-DOTAM>$^{89}$Zr-DFO.

Tetraazamacrocycles can chelate numerous, biologically relevant metal cations, and this property can potentially create a second mechanism for $^{89}$Zr$^{4+}$ dissociation from its chelator in vivo. To assess the ability of the Zr-complexes to resist demetallation by another metal cation, metal competition studies were performed, in which the radiometal complex was mixed with an excess concentration of metal salts. No demetallation of $^{89}$Zr-DOTA was observed over the 7-day experiment. In contrast, $^{89}$Zr-DFO remained only 33.9% and 72.6% intact when challenged with Fe$^{3+}$ or Ga$^{3+}$ during the same study period, respectively. The overall order of $^{89}$Zr-complex stability based upon these studies mirrored the results in the EDTA challenge experiments, further demonstrating the robust stability of Zr-tetraazamacrocycle complexes.

To further characterize the stability of Zr-tetraazamacrocycle complexes and preliminarily assess their suitability for in vivo applications, each radiometal complex was incubated with human serum proteins for 7 days at 37° C. When analyzed by radio-ITLC, $^{89}$Zr-DOTA, $^{89}$Zr-DOTP, $^{89}$Zr-DOTAM, and $^{89}$Zr-DFO showed no noticeable degradation. However, because $^{89}$Zr could be bound to serum proteins that do not migrate in the radio-ITLC system, size exclusion chromatography was performed to further characterize the stability of $^{89}$Zr-complexes. Unchelated $^{89}$Zr (as $^{89}$ZrCl$_4$) was found to be associated with serum proteins. In contrast, when serum samples containing the $^{89}$Zr-complexes were analyzed, less than 5% of radioactivity was associated with serum proteins. The intact $^{89}$Zr complexes eluted after 41-45 minutes, further reinforcing the stability of these complexes and corroborating the results obtained using radio-TLC.

Lipophilicity (log P), which provides insights into the adsorption, distribution, metabolism, and elimination of $^{89}$Zr-complexes in vivo, was determined using a water/octanol partition method. $^{89}$Zr-DOTP and $^{89}$Zr-DOTA showed the most hydrophilic characteristics, most likely due to the charge of $^{89}$Zr-complexes and their numerous hydrogen bonding interactions in solution (note the structures). These characteristics values suggest that renal excretion would be a preferred elimination route for radiometal complexes after in vivo injection.

The in vivo stability of $^{89}$Zr-DOTA, $^{89}$Zr-DOTP, and $^{89}$Zr-DOTAM were then evaluated in acute biodistribution studies using female NIH Swiss mice (6-8 wk old, n=6). The results showed that mice receiving $^{89}$Zr-DOTAM retained elevated levels of radioactivity in liver and spleen tissues, which was not excreted over the 72 hour experimental time course. In vitro, $^{89}$Zr-DOTAM aggregated and precipitated out of solution unless a low concentration of surfactant was included to stabilize the complex. While surfactant was used in the injection formulation for biodistribution studies, it is hypothesized that once in the blood stream, $^{89}$Zr-DOTAM aggregates with serum proteins, which are deposited in these tissues during circulation.

Mice intravenously injected with $^{89}$Zr-DOTA retained significantly less radioactivity in their blood, liver, kidney and bone tissue compared to mice injected with $^{89}$Zr-DOTP. Higher retention of $^{89}$Zr-DOTP was predicted by the in vitro kinetic stability results, and may suggest transchelation to serum proteins or reduced stability in the presence of the lower pH environments that may be observed in Kupffer cell lysosomes or the kidney. Radioactivity retention in bones of mice receiving $^{89}$Zr-DOTP may be caused by a number of factors, e.g. residualization of $^{89}$Zr that was transchelated by hydroxylapatite, or adsorption of the intact complex in the bone matrix due to the influence of the four phosphate-containing pendant arms of the $^{89}$Zr-DOTP complex. The latter phenomenon was observed with other radiometal-DOTP complexes. Reducing the number of phosphate-containing pendant arms may reduce bone retention, and studies of phosphate-containing $^{64}$Cu-tetraazamacrocycles show that this strategy can reduce the amount of radioactivity retained in bone tissue.

The performance of $^{89}$Zr-DOTA and $^{89}$Zr-DFO was then compared. Each had similar blood excretion profiles, but $^{89}$Zr-DOTA had lower radioactivity retention in liver, kidney, and bone tissues. Interestingly, while radioactivity retention in bone tissue of mice injected with $^{89}$Zr-DFO increases over time, that in mice receiving $^{89}$Zr-DOTA remained low with no statistically significant changes at any time point. Without being bound by theory, one possible explanation for these observations may be the tetraazamacrocycle's ability to form an octa-coordinate complex with the $^{89}$Zr$^{4+}$ ion. The saturated coordination sphere plus the four hard oxygen donor groups are believed to produce a complex that remains resistant to chemical, biological and physical factors that may make radiometal complex unstable in vivo. It is suspected that this robust stability will be maintained when $^{89}$Zr-DOTA is incorporated into an antibody conjugate and these studies are currently being performed. $^{89}$Zr-DOTMA also shows a very similar clearance pattern to $^{89}$Zr-DOTA.

Normal mice were injected with $^{89}$Zr-DFO and $^{89}$Zr-DOTA and dynamic PET imaging done from 0-60 minutes, followed by static imaging at 2, 4, and 24 hours after injection. Both radiometal complexes exhibited a similar excretion profile based on the amount of radioactivity in the blood pool and the liver during first 60 minutes. Radioactivity in the kidney and bone was much lower in mice receiving $^{89}$Zr-DOTA compared to $^{89}$Zr-DFO, suggesting a better excretion profile from these tissues. Both $^{89}$Zr-DFO and $^{89}$Zr-DOTA are excreted renally, with elevated levels of radioactivity in the kidneys and bladder at early time points. However, by 4 h, nearly all the radioactivity was excreted from mice that received $^{89}$Zr-DOTA, and after 24 h, radioactivity was barely above background levels. By contrast, more radioactivity accumulated in the kidneys of mice injected with $^{89}$Zr-DFO at 4 h, and was still visible in static images acquired after 24 h. Results of region-of-interest analyses on the data acquired during the static imaging sessions further corroborate these biodistribution studies, which demonstrate the superiority of $^{89}$Zr-DOTA over $^{89}$Zr-DFO.

This data should reinforce efforts focused on the exploration of these radiometal chelates in immuno-PET applications. The use of $^{89}$ZrCl$_4$ allows access to a diverse group of ligands to produce ultra-stable $^{89}$Zr-complexes, previously believed to be inaccessible or unstable. Additionally, the synthetic methodologies described herein can facilitate a systematic study of $^{89}$Zr coordination chemistry using inorganic chemistry, radiochemistry and molecular imaging techniques to elucidate how to create $^{89}$Zr-radiopharmaceuticals with excellent stability in vivo.

Thus, in conclusion, the feasibility of using tetraazamacrocycles as chelating ligands for the PET radioisotope zirconium-89 is shown herein. To the inventor's' knowledge, this is the first description of the structural characterization of Zr-DOTA using single crystal x-ray diffraction. All four ring nitrogen atoms and carboxylic acid pendant arms are coordinated to the Zr$^{4+}$ ion yielding an octa-coordinate complex, which contributes to its unanticipated stability. Studies with the radioactive analogs of these complexes demonstrated that they are highly stable in vitro when challenged by exogenous ligands, metal ions, or serum proteins. Using small animal PET imaging, $^{89}$Zr-DOTA demonstrated superior stability compared to $^{89}$Zr-DFO, which (prior to the present invention) is the "gold standard" among $^{89}$Zr chelating agents and the only ligand used in clinical radiopharmaceutical development involving zirconium-89. These results refute current thinking regarding the use of tetraazamacrocycles as $^{89}$Zr chelators, and may provide a way to enhance development of radiolabeled agents for precision medicine applications.

Expected Results:

The synthesis of AMCs and the evaluation of these ligands as chelators for various radiometals will be performed. Crystallographic analysis (XRD) will reveal the coordination sphere around the Zr$^{4+}$ ion in each complex. However, generating single crystals for XRD of Zr complexes has sometimes proven challenging. Accordingly, the complexes will be fully characterized using $^1$HNMR and $^{13}$CNMR to examine structural relationships between the Zr$^{4+}$ and the ligand in solution. DFT calculations will also be conducted. Because a DFT solution for $^{Nat}$Zr-DFO has been reported, this molecule can be completely characterized with our modeling protocol to validate its precision and accuracy before any calculations are attempted on Zr-AMC complexes.

Based upon current $^{Nat}$Zr-coordination chemistry literature and preliminary data demonstrating the synthesis of $^{Nat}$Zr-NOTA, $^{Nat}$Zr-DOTA, $^{Nat}$Zr-DOTP and $^{89}$Zr-DOTA, $^{89}$Zr-DOTMA and $^{89}$Zr-DOTP, it is expected that all ligands would complex Zr, but in vitro and in vivo stability will not be determined simply from complex formation. Rather, the systematic study of each $^{Nat}$Zr- and $^{89}$Zr-complex prepared with the ligands will be studied. These studies will test the current $^{89}$Zr-coordination chemistry paradigm, which states that $^{89}$Zr-chelate stability is influenced by ligands that contain polyanionic hard donor ligands that are capable of forming octa-coordinate complexes with $^{89}$Zr$^{4+}$. If this hypothesis is true then the relative performance of the ligands would be predicted to fall within the following described three groups. Group 1, which would create the least stable $^{89}$Zr complexes, would contain all of those ligands that neither have hard, polyanionic donor groups nor form octa-coordinate complexes. Group 2, which would create moderately stable $^{89}$Zr complexes, would contain those ligands that have donor groups for coordination, but cannot form octa-coordinate complexes. Group 3, which would form the most stable $^{89}$Zr-complexes, would contain those ligands that contain both polyanionic hard donor atoms and are capable of forming octa-coordinate complexes with $^{89}$Zr$^{4+}$.

High organ extraction efficiencies are needed to obtain complete soluble metabolite removal from tissue homogenates and accurate metabolism study results. If significant activity remains in the pelleted debris after the initial centrifugation step, the extraction process will be repeated, and both supernatants will be combined for further studies. If this does not increase the extraction efficiency, then different combinations of extraction solvents such as acetonitrile, acetone, water, ethanol, buffers such as acetate or HEPES and detergents such as Triton-x will be used to increase extraction. If this does not work, tissues will be digested with trypsin and collagenase after homogenization and sonication before being analyzed as described above. Using this method, the metabolite analysis could be increased dramatically. To ensure accurate molecular weight determinations of the metabolites, all columns will be calibrated with high and low molecular weight standards (GE Life sciences), and standard curves for each column will be generated before metabolite analysis.

It is postulated that the exceptional stability inherent in the $^{89}$Zr-AMC complex will be retained when incorporated into a clinically relevant, peptide based PET radiopharmaceutical. While metal-based radiopharmaceutical development has advanced significantly, limitations exist that prevent their widespread clinical use. For example, $^{68}$Ga-DOTA-TOC has entered clinical trials for the detection of SSTR2$^+$ tumors, but the imaging of patients is limited to large academic medical centers, which have the resources to maintain a $^{68}$Ge/$^{68}$Ga generator and the trained personnel to prepare the radiopharmaceutical. Moreover, $^{68}$Ga's short half-life ($t_{1/2}$=68 min.) makes distributing it over long distances extremely difficult. $^{64}$Cu's 12.7 h half-life allows it to be routinely produced and shipped throughout the USA making it an alternative to $^{68}$Ga. However, it forms an unstable complex with DOTA, which is a widely used chelator in clinical radiopharmaceuticals, and while new cross-bridged (CB) ligands demonstrate enhanced stability in vivo, very few have been evaluated clinically despite being reported more than a decade ago. Furthermore, the concept of $^{89}$Zr-labeled peptides is gaining popularity within the nuclear medicine community since the 3.3 day half-life would allow every clinical center access to clinically relevant PET radiopharmaceuticals, but the issues surrounding $^{89}$Zr-DFO in vivo stability would remain. $^{89}$Zr-DOTA based conjugates would overcome all of these limitations since $^{89}$Zr-DOTA demonstrates superior stability in vivo to $^{89}$Zr-DFO, and the long half-life would allow clinicians greater flexibility in designing imaging protocols that allow for greater data collection and enhanced disease diagnosis, staging and treatment planning. Towards this end, $^{89}$Zr-DOTA-TOC has been prepared in excellent radiochemical purity (see scheme 2) to attempt to ascertain if DOTA can be radiolabeled as part of a peptide conjugate. Preliminary data suggests that DOTA conjugated peptides can be radiolabeled with $^{89}$Zr efficiently for PET imaging applications.

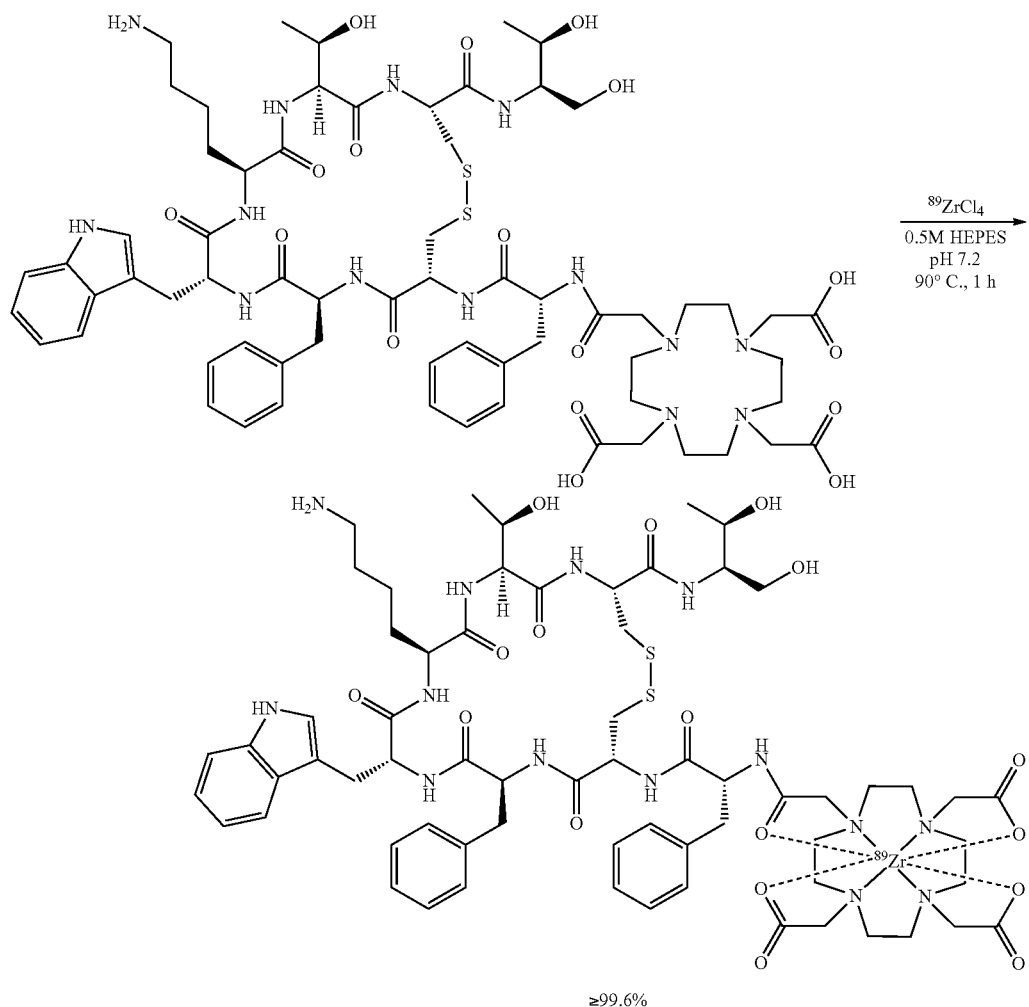

Figure 4:
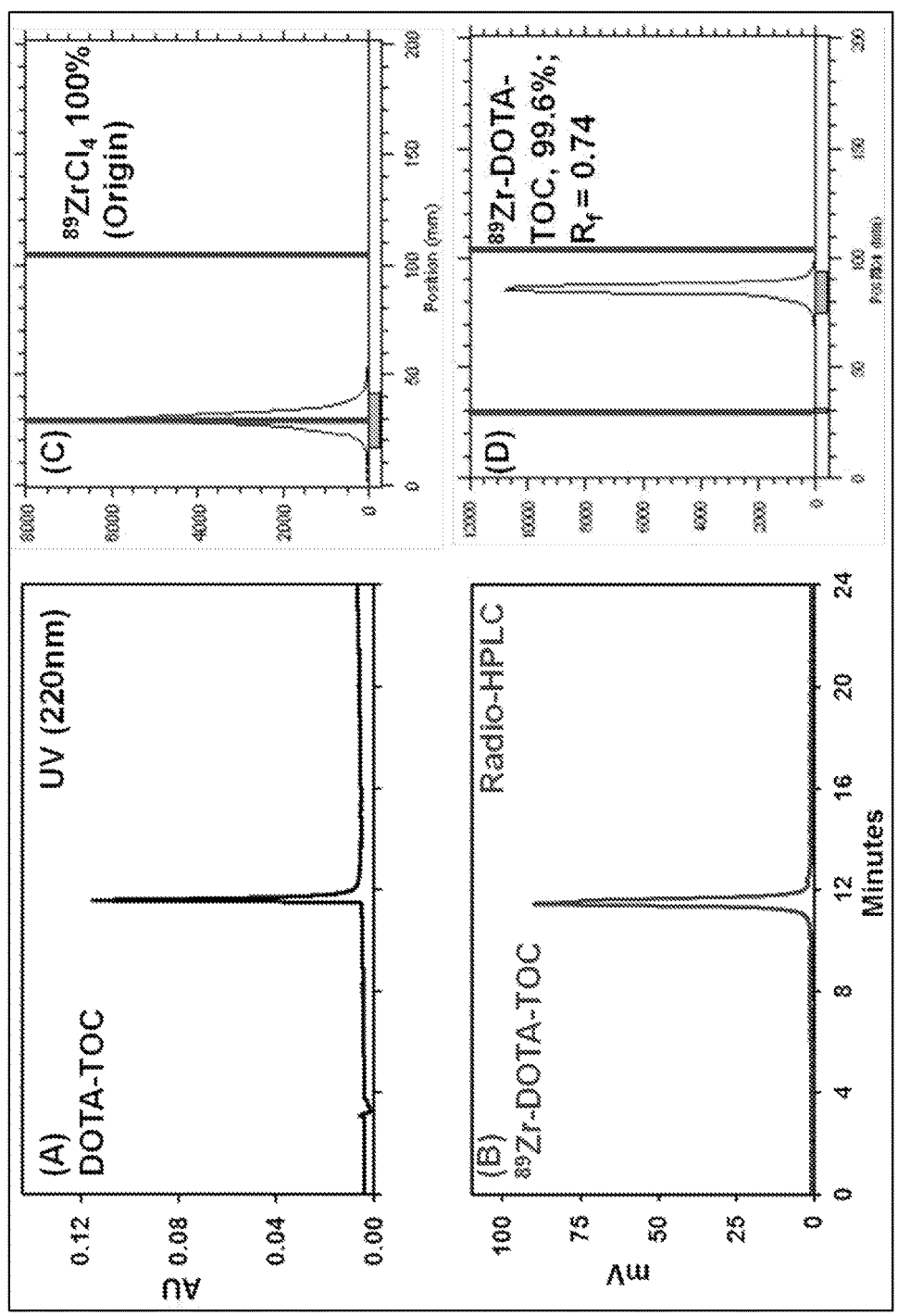
FIGS. 4 A-D show the radiochemical purity of $^{89}$Zr-DOTA-TOC assessed by radio-HPLC and radio-TLC. DOTA-TOC (A) has a retention time similar to that of $^{89}$Zr-DOTA-TOC (B). Unchelated $^{89}$Zr (C) is not observed in the radio-HPLC (B) or at the origin in the radio-TLC profile of the radiolabeled conjugate (D).

FIGS. 4 A-D show the radiochemical purity of $^{89}$Zr-DOTA-TOC assessed by radio-HPLC and radio-TLC. DOTA-TOC (A) has a retention time similar to that of $^{89}$Zr-DOTA-TOC (B). Unchelated $^{89}$Zr (C) is not observed in the radio-HPLC void volume (RT=1-2 min.) (B) or at the origin ($R_f$=0) in the radio-TLC profile of the radiolabeled conjugate (D).

Figure 5:
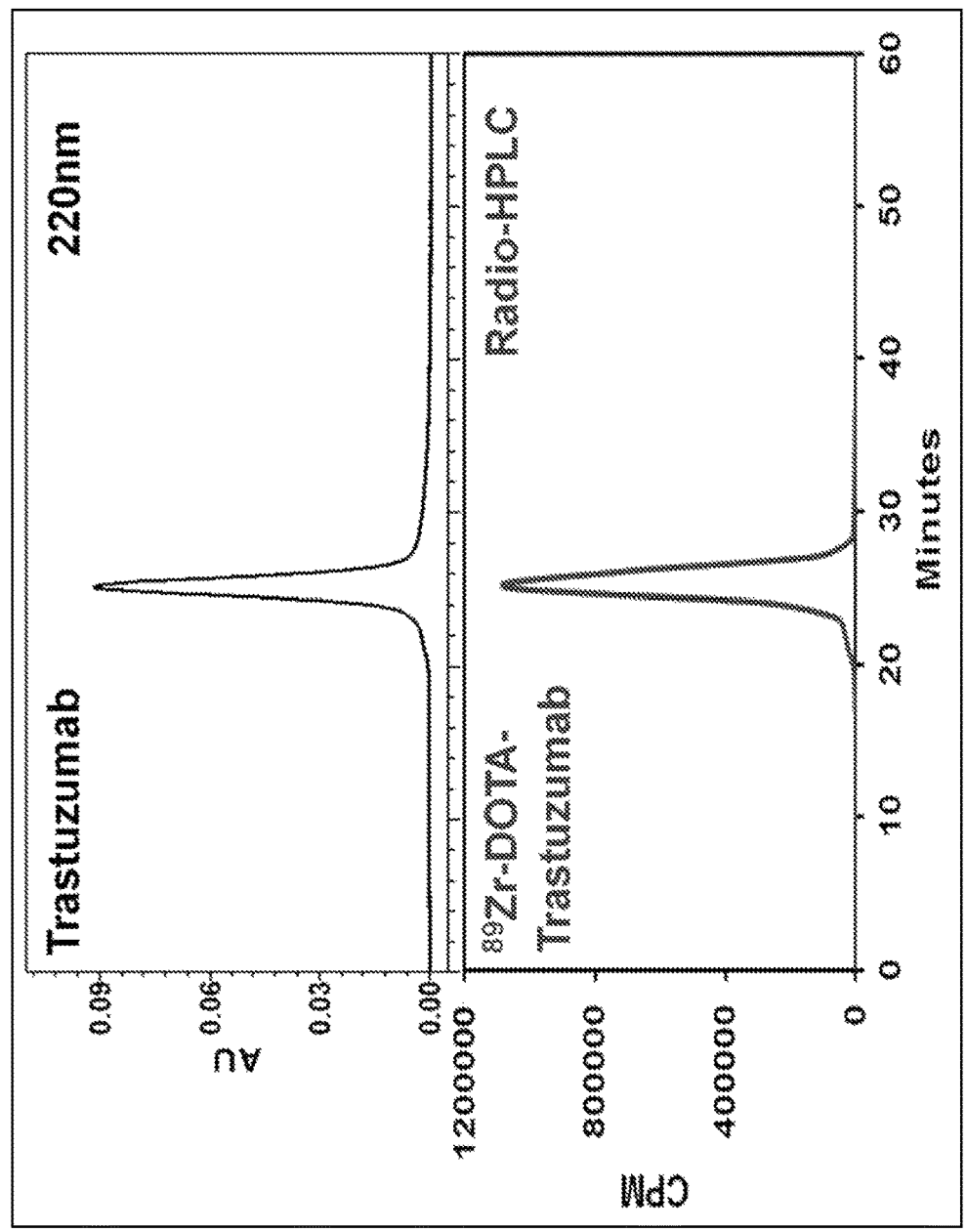
FIG. 5 shows radio-size exclusion chromatography of $^{89}$Zr-DOTA-TmAb. The retention times of TmAb (UV; upper) and $^{89}$Zr-DOTA-TmAb (lower) are in good agreement. Unchelated $^{89}$Zr is not observed demonstrating excellent radiochemical purity.

FIG. 5 shows that antibody can be linked to $^{89}$Zr-DOTA. FIG. 5 shows the results of radio-size exclusion chromatography of $^{89}$Zr-DOTA-Trastuzumab (TmAb). The retention times of TmAb (UV; upper) and $^{89}$Zr-DOTA-TmAb (lower) are in good agreement. Unchelated $^{89}$Zr is not observed demonstrating excellent radiochemical purity.

Figure 6:
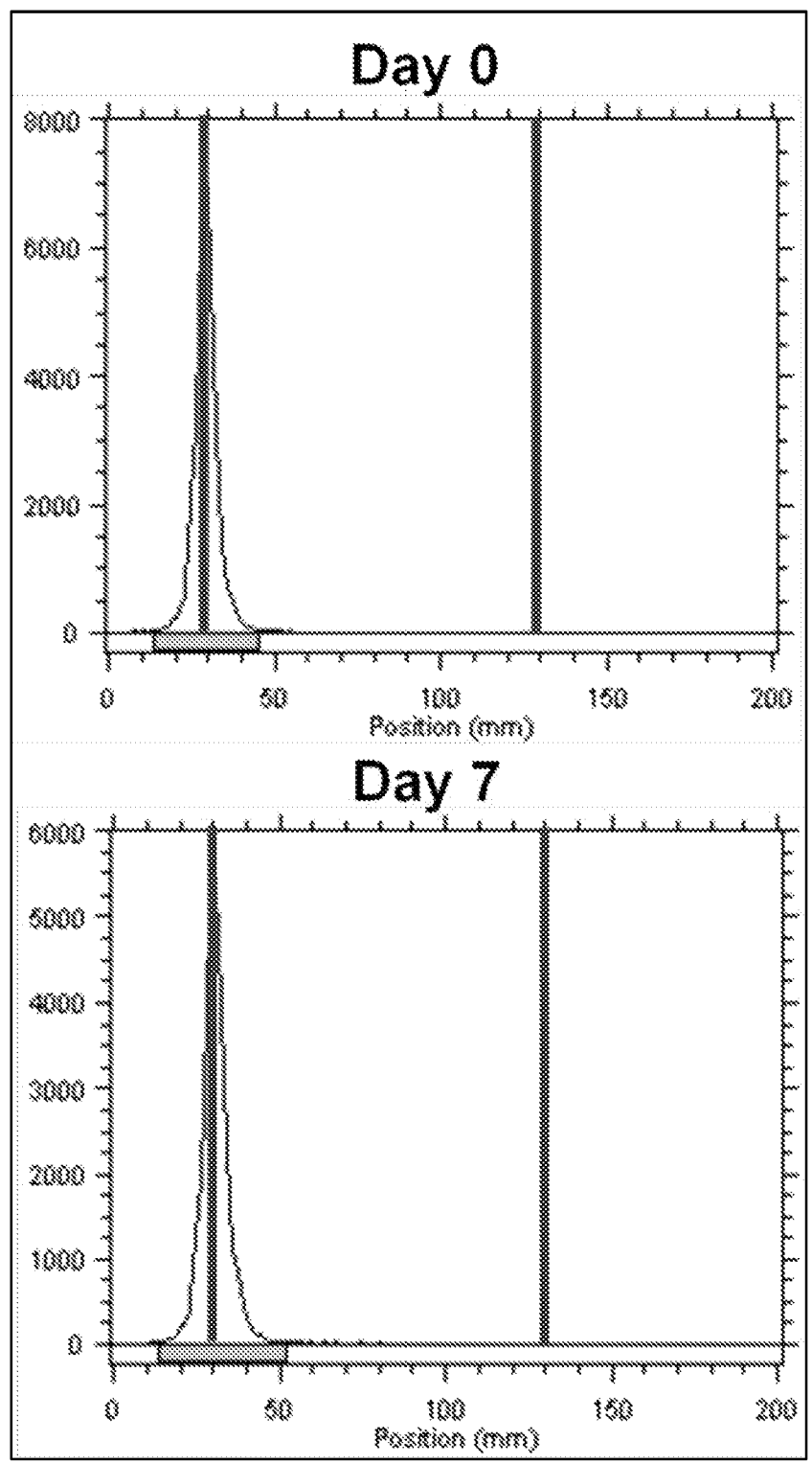
FIG. 6 shows the serum stability results of $^{89}$Zr-DOTA-TmAb. Samples were incubated with human serum for 7 days at 37° C. and analyzed by radio-TLC (ITLC-SG plates and 50 mM EDTA (pH 5) mobile phase). $^{89}$Zr-DOTA-TmAb remains at the origin. If the $^{89}$Zr-DOTA was unstable as part of this bioconjugate, the $^{89}$Zr would be transchelated to serum proteins. Any $^{89}$Zr transchelated to serum proteins is expected to be complexed by EDTA and move to the solvent front in this system. The Y-axis is counts per minute.
Figure 7:
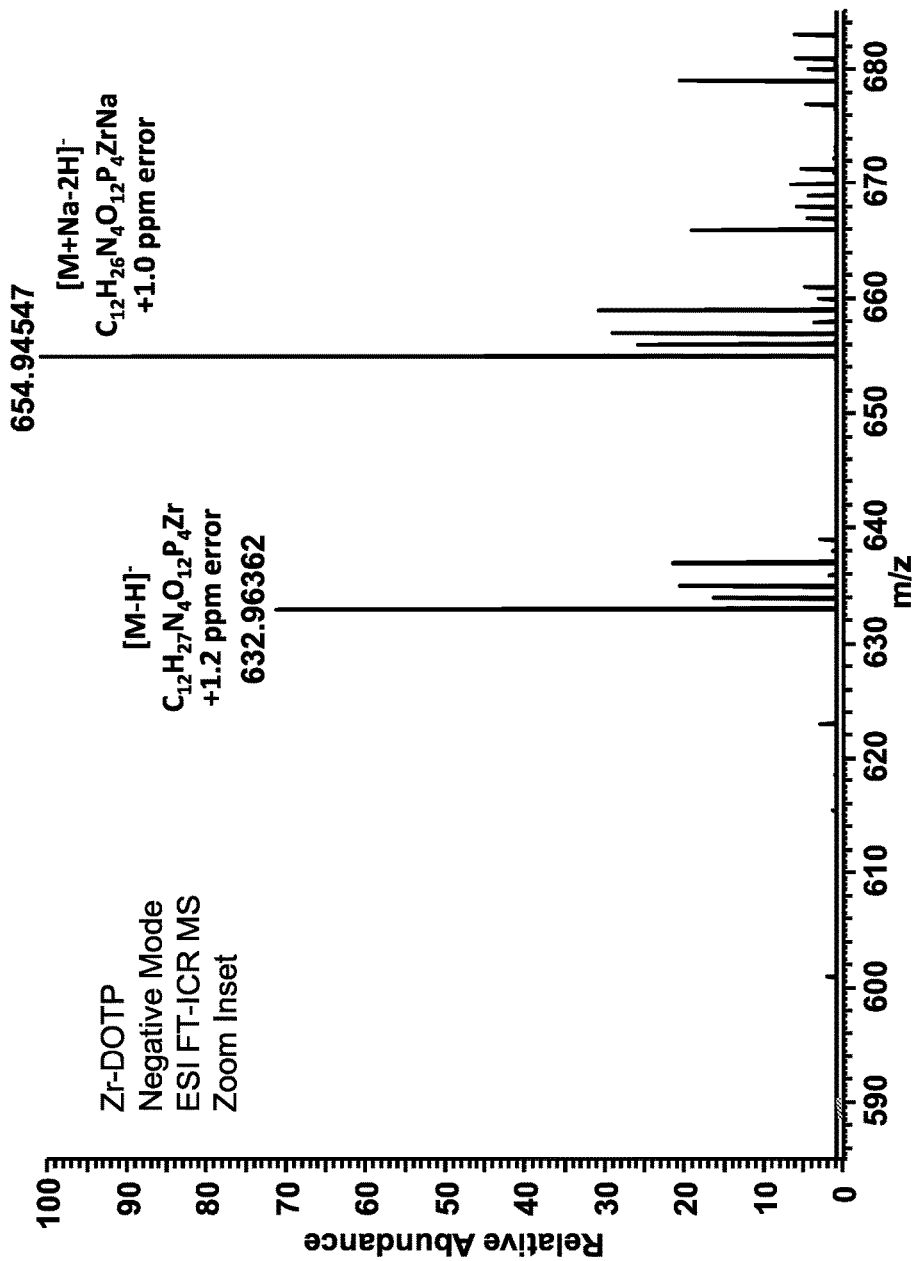
FIG. 7 shows a high resolution mass spectrum of $^{Nat}$Zr-DOTP. High resolution mass spectrometry confirms the formation of $^{Nat}$Zr-DOTP. Only a 1.2 ppm error is observed between theoretical and observed molecular weights.
Figure 8:
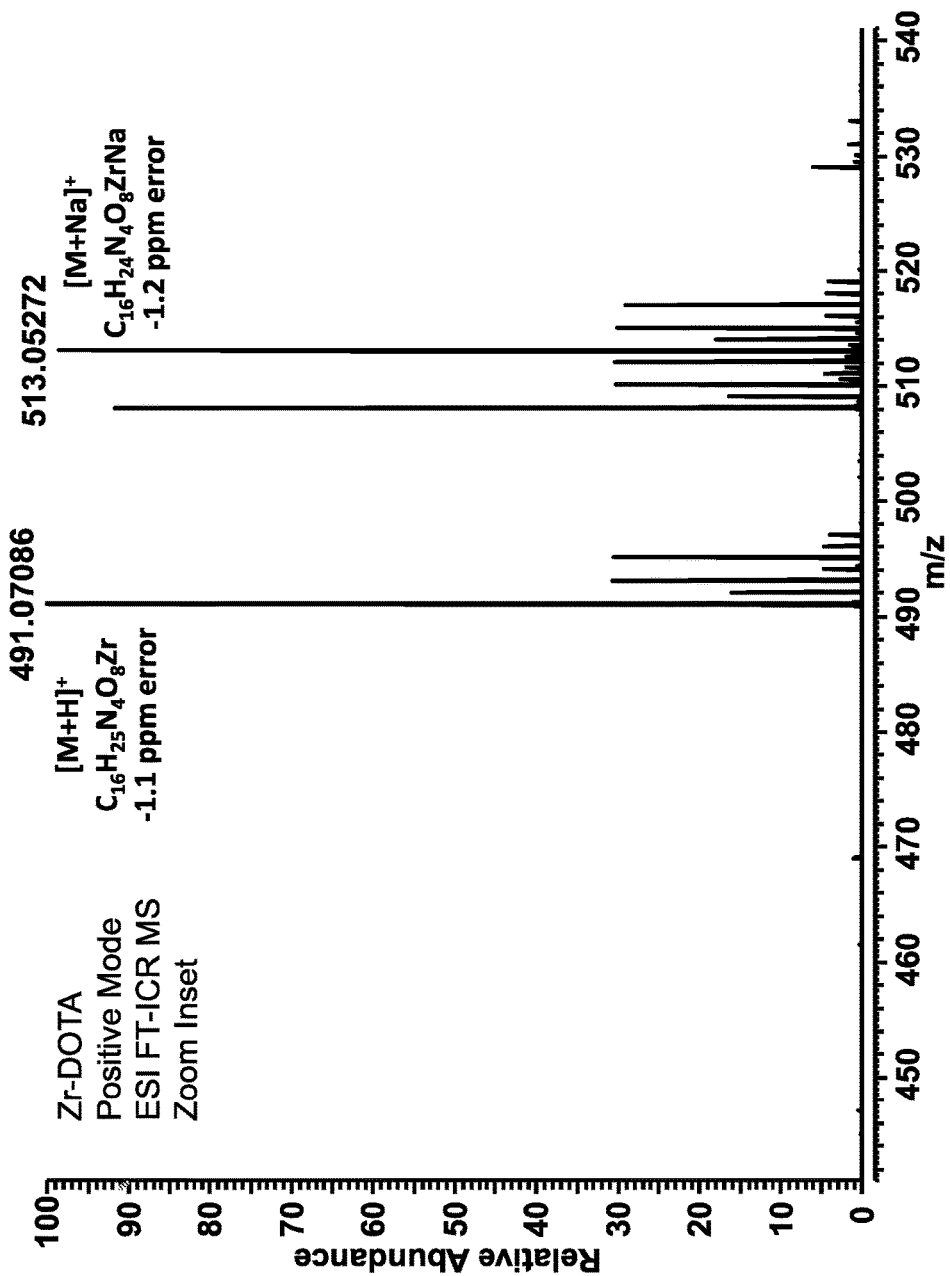
FIG. 8 shows a high resolution mass spectrum of $^{Nat}$Zr-DOTA. High resolution mass spectrometry confirms the formation of $^{Nat}$Zr-DOTA. Only a 1.2 ppm error is observed between theoretical and observed molecular weights.

FIG. 6 shows the serum stability results of $^{89}$Zr-DOTA-TmAb. Samples were incubated with human serum for 7 days at 37° C. and analyzed by radio-TLC (ITLC-SG plates and 50 mM EDTA (pH 5) mobile phase). $^{89}$Zr-DOTA-TmAb remains at the origin ($R_f$=0). If the $^{89}$Zr-DOTA was unstable as part of this bioconjugate, the $^{89}$Zr would be transchelated to serum proteins. Any $^{89}$Zr transchelated to serum proteins is expected to be complexed by EDTA and move to the solvent front in this system.

Research Design and Methods:

In Scheme 2 above, it has been demonstrated that DOTA-TOC can be radiolabeled with $^{89}$Zr using $^{89}$ZrCl$_4$ in order to prove the utility of this strategy for preparing clinically relevant radiopharmaceuticals. It is expected that $^{89}$Zr-DOTA will retain its extraordinary stability when conjugated to TOC, and it is expected that the resulting radiopharmaceutical will perform equally well at detecting SSTR2 receptor expression when compared to $^{89}$Zr-DFO-TOC and $^{68}$Ga-DOTA-TOC, which is currently in clinical trials. By comparing the former radiopharmaceutical with the latter two in vitro and in vivo, the radiometal chelate stability will be evaluated and the imaging properties of $^{89}$Zr-DOTA-TOC with relevant model tracers will be ascertained. The following experiments will also be performed.

Radiochemistry and In vitro Serum Stability:

cGMP compliant $^{68}$Ga-DOTA-TOC will be purchased from IBA Molecular, Inc. (Dulles, Va.), while cGMP compliant DOTA-TOC (ABX), and DFO-TOC (CPC Scientific) will be radiolabeled with $^{89}$Zr using a modified procedure from previous procedures (see Scheme 2). Specific activity ($A_s$) of this radiotracer will be adjusted to be comparable to that of the $A_s$ of $^{68}$Ga-DOTA-TOC. $^{89}$ZrCl$_4$ will be used as a standard control. Radiochemical purity and serum stability will be evaluated using the Waters HPLC system described above. Aliquots will be analysed hourly for the first 8 h. After this period, the $^{89}$Zr-radiotracers will be analysed daily for 7 days. Samples will be centrifuged and the radioactivity in the supernatant and the pellet measured. Samples of supernatant will be evaluated using size exclusion chromatography. Retention times of any peaks in the chromatogram will be compared to those of the radiotracers and $^{89}$ZrCl$_4$ and $^{68}$GaCl$_3$ (standard controls); retention times not matching the standard controls will be considered products of instability.

In vitro Binding Affinity (K$_D$) and Internalization Studies:

Affinity of $^{89}$Zr-DOTA-TOC for SSTR2 will be evaluated using a modified known method and AR42J cells, which maintains many characteristics of normal pancreatic acinar cells and form neuroendocrine (NE), gastroenteropancreatic (GEP) tumors in nude mice. Briefly, AR42J cell membranes in microfuge tubes (1×10$^6$ cells/500 µL) will be incubated with $^{89}$Zr-DOTA-TOC, $^{89}$Zr-DFO-TOC or $^{68}$Ga-DOTA-TOC and increasing concentrations of the analogous non-radioactive conjugate at 4° C. for 1 h. After the incubation, aliquots will be removed and counted by gamma counting. Non-specific binding will be determined by conducting an assay in the presence of excess non-radioactive conjugate. All K$_D$ and B$_{max}$ values will be estimated from non-linear curve fitting of bound conjugate versus the sum concentration of radioactive and non-radioactive analogues using PRISM (GraphPad, San Diego, Calif.) software.

For internalization studies, each radiotracer and AR42J cells (1×10$^6$ cells/500 µL) will be combined to achieve a final concentration of 4 nM, and incubated at 37° C. with rotation. To block specific binding at each time point, a 500 µL cell suspension (1×10$^6$ cells/(500 µL) will be incubated for 5 minutes at room temperature with excess of the non-radioactive analogue. At each time point, surface-bound fractions will be collected by acid extraction of cells. Internalized radioactivity will be collected by lysing the cells in 0.5% SDS. Radioactivity in each fraction will be counted in a gamma counter. The total protein concentration in the cell lysate will be determined using a standard BCA protein assay (Pierce Biotechnology, Rockford, Ill.). Internalized and surface-bound fractions will be expressed as counts/minute/mg protein.

Biodistribution and Small Animal Imaging Studies:

Female nude mice will be implanted with AR42J cells in the hind limb, and tumor growth will be evaluated weekly using manual tumor volume (volume=0.52×[width]$^2$×[length]) measurements. Animals with palpable tumors will be injected with one of the three radiotracers (0.56 MBq (15 µCi)). Animals receiving $^{68}$Ga-DOTA-TOC will be sacrificed at 0.5, 1, 2, 4 and 6 h p.i (post injection). Animals receiving either $^{89}$Zr-DFO-TOC or $^{89}$Zr-DOTA-TOC will be sacrificed at 1, 4, 24, 48 and 72 h p.i. A second murine cohort (n=6) bearing AR42J tumors will receive a co-injection of the cold ligand (500 fold excess) along with the analogous radiotracer to examine competition in vivo. Tumors and organs of interest will be removed, weighed and counted on a gamma counter. Percent injected dose per gram (% ID/g) and percent injected dose per organ (% ID/organ) will be counted and compared to a weighed, counted standard for all groups.

For imaging studies, female nude mice bearing AR42J tumors will be injected with one of the three radiotracers (11 MBq (300 µCi)). Animals receiving $^{68}$Ga-DOTA-TOC will be imaged at 0.5, 1, 2, 4 and 6 h p.i. Animals receiving either $^{89}$Zr-DFO-TOC or $^{89}$Zr-DOTA-TOC will be sacrificed at 1, 4, 24, 48 and 72 h p.i. A second cohort (n=6) of female nude mice bearing AR42J tumors in the hind limb will receive a co-injection of cold ligand (500 fold excess) with the analogous radiotracer to examine in vivo competition through imaging. PET images will be reconstructed and SUVs (and % ID/g) will be determined as described herein.

After imaging concludes, tumors will be harvested from euthanized animals and embedded in optimum cutting temperature (OCT) compound (Miles, Inc. Elkhart, Ind.). Frozen sections (4-6 µm) will be cut, fixed in ice-cold acetone and stained with hematoxylin and eosin (H&E) and for SSTR2 expression using an anti-SSTR2 mAb (EMD Millipore, Billerica, Mass.). Serial sections will also be cut for autoradiography and developed using a Typhoon 9210 Variable Mode Imager (Molecular Devices, Sunnyvale, Calif.). Signal intensities will be quantified according to a set of autoradiography standards (GE Healthcare). Autoradiography and histology will serve to corroborate the data obtained through small animal PET/CT imaging and provide greater proof of SSTR2 antigen binding by the radiotracers.

Statistical Analysis:

To demonstrate that $^{89}$Zr-DOTA retains its extraordinary stability when conjugated to TOC, retention in the tumor (n=6 mice/cohort) will be tested at 4 hours for all three compounds and in the bone, kidney, and liver at 72 hours for $^{89}$Zr-DOTA-TOC and $^{89}$Zr-DFO-TOC. Using a two sided t-test, type 1 error rate of 0.05, and 90% power, a difference will be able to be detected of approximately two standard deviations. Pilot data for 72 hours is not available, but at 24 hours the estimable difference detected for accumulation in the bone, kidney, and liver would translate to a difference of at least 2.6% ID/g in each tissue, assuming a standard deviation of 1.25. Blood retention is expected to be similar, but with an assumed standard deviation of 0.08, a detectable difference of 0.17% ID/g is anticipated. Tumor retention of all compounds is expected to be similar at 4 hours, but if a significant difference does exist it would be identified if the difference is greater than 2 standard deviations. Exploratory analysis will also be conducted estimating retention at every time point, and a repeated measures generalized linear model will be used to evaluate differences throughout the entire data collection period.

Expected Results.

Few difficulties are expected with the tests with SSTR2 animal models and $^{68}$Ga and $^{89}$Zr chemistry experiments. It is expected that $^{68}$Ga-DOTA-TOC will be procured from IBA Molecular, Inc. Additionally and or alternatively, a $^{68}$Ge/$^{68}$Ga generator will be used to produce $^{68}$Ga-DOTA-TOC.

It is expected that the above experiments will allow a comparison between $^{89}$Zr-DOTA-TOC, $^{89}$Zr-DFO-TOC and $^{68}$Ga-DOTA-TOC to assess affinity, stability, biodistribution and tumor targeting. It is assumed that $^{89}$Zr-DOTA will be the most stable $^{89}$Zr-AMC to be identified here. If a different complex emerges that is more stable than $^{89}$Zr-DOTA, its conjugate will be prepared and it will be compared to $^{89}$Zr-DFO-TOC and its $^{68}$Ga-analogue provided that this $^{68}$Ga-analogue can be prepared with similar radiochemical purity and specific activity.

Because the use of $^{89}$Zr-AMCs in radiopharmaceuticals has never been attempted before, tests will be conducted to ascertain how $^{89}$Zr-DOTA will affect the in vitro and in vivo performance of $^{89}$Zr-DOTA-TOC compared to $^{68}$Ga-DOTA-TOC. Previously, it has been shown that varying the radiometal chelate alters the affinity of somatostatin based radiopharmaceuticals for SSTR2, and it is possible that this effect will be observed. However, based upon experiments with $^{Nat}$Y-DOTA-TOC, these changes would still place the affinity of $^{89}$Zr-DOTA-TOC in the low nanomolar range, which is still useful for in vivo imaging. Although contrast for all radiotracers would be reduced at early time points, all radiotracers are expected to image SSTR2 tumors equally well. Additionally, the long half-life of $^{89}$Zr should allow for improved contrast and tumor visualization at time points beyond the utility of $^{68}$Ga based PET imaging. It is expected that all three radiotracers will be excreted through the kidneys, which represent the major excretion path for TOC based radiopharmaceuticals. A comparison of $^{89}$Zr-DOTA-TOC and $^{89}$Zr-DFO-TOC should demonstrate that the extraordinary stability of $^{89}$Zr-DOTA is retained when part of a peptide conjugate (or alternatively when part of a monoclonal antibody). The former should demonstrate less retention in the kidney and liver. Although peptides typically undergo expedited clearance, elevated bone retention has been observed in mice injected with $^{89}$Zr-DFO conjugated peptides, and it is expected that animals injected with $^{89}$Zr-DOTA-TOC will accumulate less radioactivity in their bones when compared to $^{89}$Zr-DFO-TOC.

In an embodiment, the peptide linked complexes Zr-DOTA-c(RGDyK) and Zr-NOTA-c(RGDyK) have been made. Thus, in one embodiment, the present invention relates to methods of not just treating cancer but also other disease states wherein RGD containing compounds serve as ligands for $\alpha_v\beta_3$ receptor. Accordingly, in an embodiment, the present invention relates to methods of treating inflammation/infection, rheumatoid arthritis and osteoarthritis as well as cardiovascular diseases where $\alpha_v\beta_3$ receptor is expressed as a consequence of disease. $\alpha_v\beta_3$ receptor has also been implicated in the growth and metastasis of a cancer cell, and inflammatory diseases, e.g., rheumatoid arthritis, osteoarthritis, hepatitis, endometriosis, bronchial asthma, fibrosis, diabetes, arteriosclerosis, multiple sclerosis, granuloma, an inflammatory bowel disease (ulcerative colitis and Crohn's disease), and various autoimmune diseases. Accordingly, in one embodiment, the method relates to the treatment of these various diseases/disease states.

Although not likely, there is a remote chance that $^{89}$Zr-DOTA-TOC will be less stable in vitro and in vivo than $^{89}$Zr-DFO-TOC. This may be attributed to the lack of an octa-coordination environment around the $^{89}$Zr$^{4+}$ given that one of the pendant arms has been used

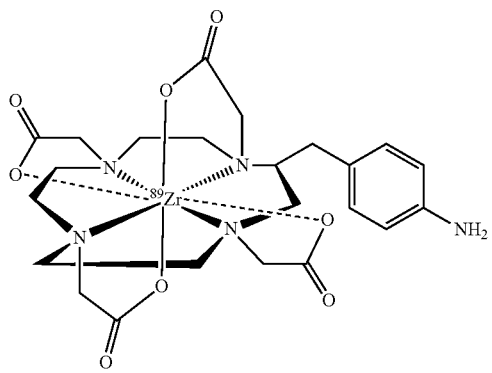

Theoretical: 596.1 [(M + H)$^+$]
Found: 596.3 [(M + H)$^+$]

Theoretical: 618.1 [(M + Na)$^+$]
Found: 618.3 [(M + Na)$^+$]

for conjugation to TOC. To circumvent this, efforts will be redirected to prepare DOTA-Bn-TOC using DOTA-Bn-NH$_2$ as the chelate. $^{Nat}$Zr-DOTA-Bn-NH$_2$ has been made and characterized using mass spectrometry (see the below structure), and since DOTA will be linked to TOC through the p-bezylamino functional group, all four carboxylic acid pendant arms will be available for $^{89}$Zr coordination. Once prepared, this new conjugate will be radiolabeled with $^{89}$Zr and the experiments outlined above will be executed.

Ascertaining $^{89}$Zr-AMCs In Vivo Stability after being Conjugated to Trastuzumab (TmAb)

Figure 16:
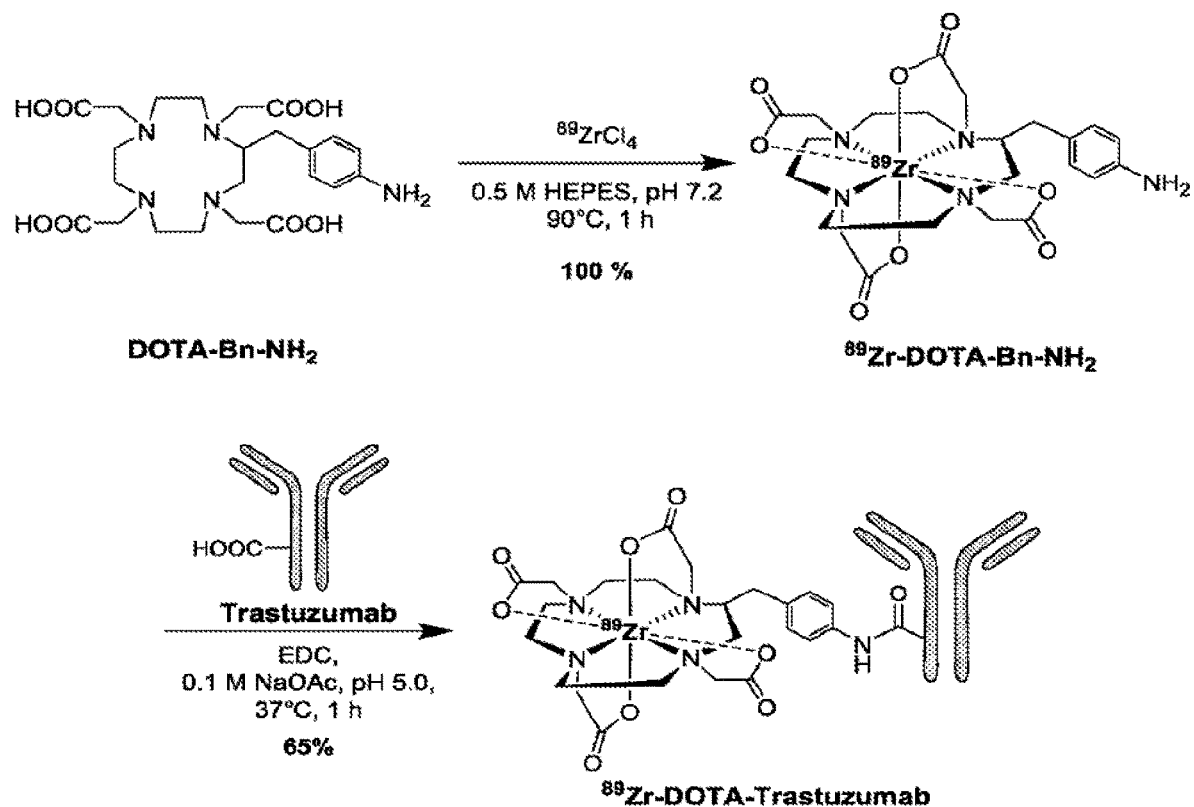

FIG. 16 depicts the radiochemical synthesis of Zr-DOTA-Trastuzumab and shows that antibody can be linked to $^{89}$Zr-DOTA.

Figure 17:
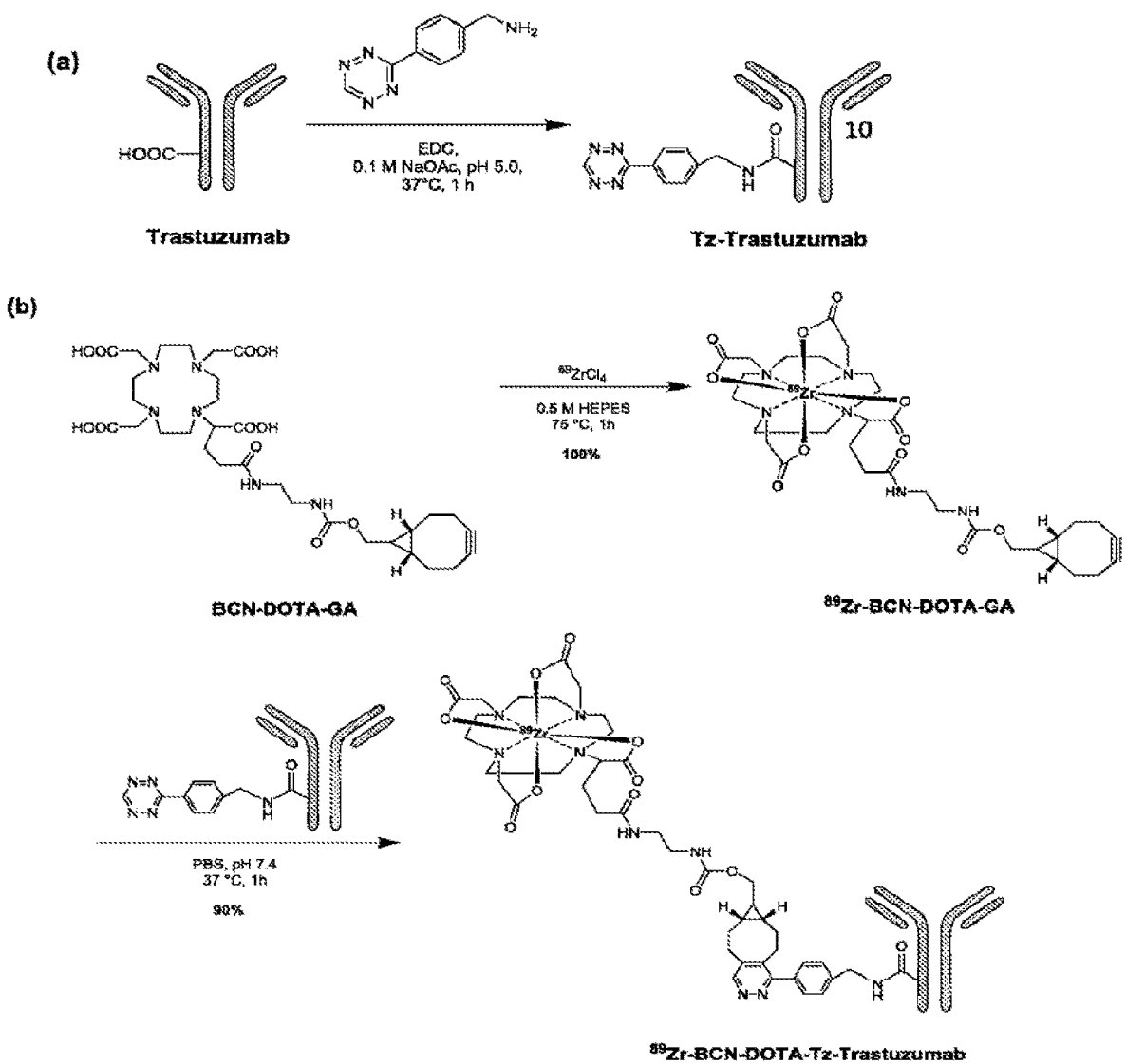

FIG. 17 shows $^{89}$Zr-DOTA-trastuzumab using the reactions ((a) and (b)). Reaction (a) shows modification of the carboxylic group of trastuzumab. Reaction (b) shows chelation of BCN-DOTA-GA to $^{89}$Zr.

Figure 13:
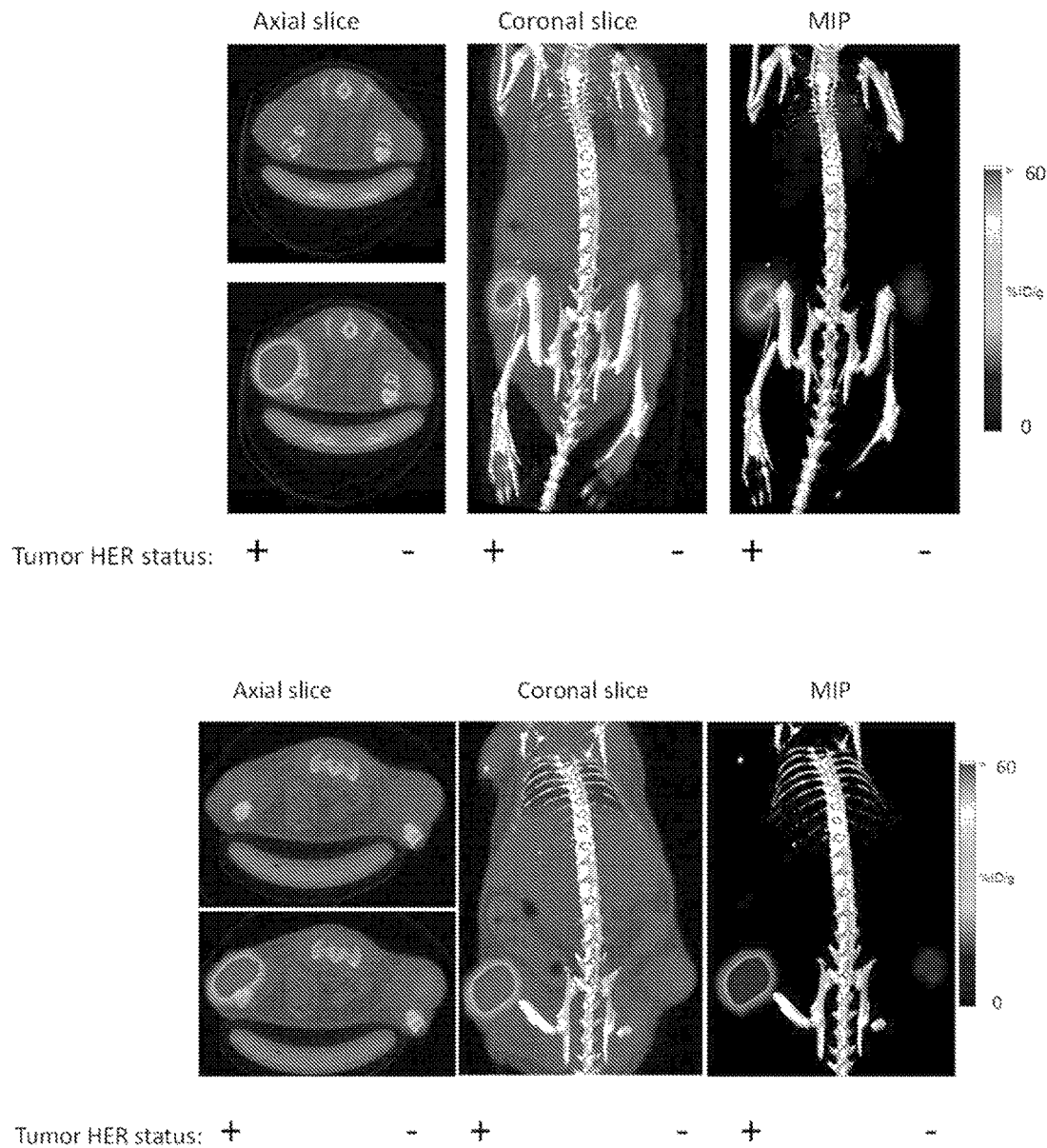
FIG. 13 shows exemplary imaging results of nude mice with HER2$^+$2170 tumors and HER2$^-$ 827 tumors implanted in contralateral flanks wherein $^{89}$Zr-DOTA-trastuzumab was injected into the mice and PET imaging performed.

Efficient coupling of $^{89}$Zr-DOTA to trastuzumab was shown. Using the nude mice with HER2$^+$ 2170 tumors and HER2$^-$ tumors implanted in contralateral flanks as the mouse model, $^{89}$Zr-DOTA-trastuzumab was injected into mice and PET imaging was performed. The results of these studies can be found in FIG. 13 and the 144 h post-pet biodistribution data is found in Table 6. $^{89}$Zr-DOTA-trastuzumab was able to target the HER2$^+$ tumors efficiently. More importantly, the 144 h post-PET biodistribution revealed a 4 fold reduction in radioactivity that was retained in the bone tissue of mice receiving $^{89}$Zr-DOTA-trastuzumab when compared to the bone tissue of mice injected with $^{89}$Zr-DFO-trastuzumab.

TABLE 6

144 h post-PET biodistribution results comparing tissue retention of $^{89}$Zr-DOTA-Trastuzumab and $^{89}$Zr-DFO-Trastuzumab.

| | % ID/g | |
|---|---|---|
| Tissue/Organ | $^{89}$Zr-DOTA-Trastuzumab | $^{89}$Zr-DFO-Trastuzumab |
| Blood | 8.72 ± 1.48 | 6.56 ± 1.35 |
| Heart | 2.56 ± 0.46 | 1.48 ± 0.23 |
| Lung | 7.18 ± 1.51 | 4.31 ± 0.57 |
| Liver | 3.75 ± 0.29 | 4.44 ± 0.33 |
| SMI + contents | 1.15 ± 0.36 | 0.80 ± 0.12 |
| LGI + contents | 0.94 ± 0.16 | 1.15 ± 0.08 |
| Kidney | 3.95 ± 0.32 | 4.59 ± 0.29 |
| Spleen | 7.20 ± 1.80 | 8.25 ± 0.83 |
| Pancreas | 0.93 ± 0.21 | 0.78 ± 0.10 |
| Stomach | 0.62 ± 0.18 | 0.55 ± 0.27 |
| Muscle | 0.74 ± 0.14 | 0.46 ± 0.11 |
| Fat | 0.79 ± 0.22 | 0.65 ± 0.18 |
| Bone | 2.05 ± 0.21 | 8.28 ± 0.48 |
| Tumor (+) | 47.43 ± 11.69 | 35.80 ± 4.70 |
| Tumor (−) | 14.12 ± 1.87 | 17.41 ± 6.50 |
| Tail | 1.55 ± 0.32 | 1.65 ± 0.18 |
| Std | 0.98 ± 0.01 | 1.00 ± 0.02 |

FIG. 5 shows the results of radio-size exclusion chromatography of $^{89}$Zr-DOTA-Trastuzumab (TmAb). The retention times of TmAb (UV; upper) and $^{89}$Zr-DOTA-TmAb (lower) are in good agreement. Unchelated $^{89}$Zr is not observed demonstrating excellent radiochemical purity.

FIG. 6 shows the serum stability results of $^{89}$Zr-DOTA-TmAb. Samples were incubated with human serum for 7 days at 37° C. and analyzed by radio-TLC (ITLC-SG plates and 50 mM EDTA (pH 5) mobile phase). $^{89}$Zr-DOTA-TmAb remains at the origin (R$_f$=0). If the $^{89}$Zr-DOTA was unstable as part of this bioconjugate, the $^{89}$Zr would be transchelated to serum proteins. Any $^{89}$Zr transchelated to serum proteins is expected to be complexed by EDTA and move to the solvent front in this system.

The need for ligands that form ultra-stable $^{89}$Zr complexes has led to the creation of several new $^{89}$Zr chelators. Others have made chelators that are not superior to DFO either alone or as part of an antibody conjugate. However, in one embodiment of the present invention, it is shown that $^{89}$Zr-DOTA is superior to $^{89}$Zr-DFO. More excitingly, preliminary data reveals that $^{89}$Zr-DOTA-TmAb can be prepared using $^{89}$ZrCl$_4$ and is stable to serum challenge for 7 days at 37° C.

In this regard, preliminary data suggests that DOTA forms ultra-stable $^{89}$Zr complexes even when incorporated into a mAb based radiopharmaceutical and challenged by serum proteins in vitro. Going forward, it will be demonstrated that $^{89}$Zr-AMCs retain their robust stability in vivo when conjugated to TmAb and demonstrate that in vivo biodistribution and imaging characteristics are superior to $^{89}$Zr-DFO-TmAb. To show this, the following experiments will be performed.

cGMP TmAb will be purchased from Myoderm, Inc. (Norristown, Pa.), conjugated with isothiocyanate-desferrioxamine (NCS-DFO, Macrocyclics, Inc.), and then reacted with $^{89}$ZrCl$_4$ at 37 C° to yield $^{89}$Zr-DFO-TmAb with a specific activity of at least 37 MBq/mg. Since elevated temperatures are needed to quantitatively radiolabel DOTA with $^{89}$Zr, a two-step synthesis strategy will be used to prepare $^{89}$Zr-DOTA-TmAb. The first step will be to prepare $^{89}$Zr-DOTA-Bn-NH$_2$. The second step will involve the use of 1-ethyl-3-(3-dimethylaminopropyl) carbodiimide (EDC) coupling between $^{89}$Zr-DOTA-Bn-NH$_2$ and activated carboxylic acid groups on the mAb surface that are available for conjugation. This two-step process has been used successfully to synthesize the $^{89}$Zr-DOTA-TmAb, in order to generate preliminary data. $^{89}$ZrCl$_4$ will be used as a standard control, and purity will be evaluated using a Waters size exclusion HPLC system that was described above. The number of accessible DFO or DOTA chelates conjugated to the mAbs will be measured by isotopic dilution. Finally, a serum stability comparison of both radiopharmaceuticals will be evaluated as enumerated above using $^{89}$ZrCl$_4$ as a standard control.

In Vitro Assays: Immunoreactivity (IR) and Affinity (K$_a$) Determination.

Immunoreactivity of each $^{89}$Zr-TmAb will be determined by the Lindmo method with 2170 (HER$^+$) and 827 (HER$^-$) cell lines. Briefly, $^{89}$Zr-TmAb will be incubated for 60 min at 4° C. (continuous mixing) with a range of cell concentrations. Cells will be washed thrice, pelleted using centrifugation, and the activity within the pellet will be measured by gamma counting. Three samples of $^{89}$Zr-TmAb (at the same concentration as those initially added to the cells) will be measured at the same time as cell pellets. A background correction will be applied by adding 100-fold unlabeled TmAb to three tubes containing cells before addition of $^{89}$Zr-TmAb. The percentage of $^{89}$Zr-TmAb binding to each cell line will be calculated ((cpm cell pellet/mean cpm $^{89}$Zr-TmAb standards)×100), and the percent binding will be plotted as a function of cell concentration using GraphPad Prism 5.0 software (San Diego, Calif.). IR (immunoreactivity) will be calculated from the Y-intercept of the inverse plot of both values.

The association constant (K$_a$) and the number of antibody molecules bound per cell (B$_{max}$) will be determined using Scatchard analysis. Varying concentrations (0.01-8 µM) of TmAb will be added to 2×10$^6$ 2170 (HER$^+$) or 827 (HER$^-$) cells and mixed before adding $^{89}$Zr-TmAb. After 60 min at 4° C., the cells will be washed thrice and counted as described above. The free, reactive antibody will be calculated [(100% bound)/100× total antibody x IR fraction]. Specific binding ((nM): [total antibody x % bound]) will be graphed against specific binding/reactive free antibody, and the K$_a$ will be determined from the negative slope of the line. The B$_{max}$ will also be derived ([X-intercept of Scatchard plot (nM)/1000×6.02×10$^{23}$)/2×10$^6$ cells]).

Biodistribution and Small Animal Imaging Studies:

All studies will be conducted as described above with the following modifications. Female nude mice will be implanted with 2170 (HER$^+$) and 827 (HER$^-$) cells in contralateral flanks. Animals will be injected with either $^{89}$Zr-DFO-TmAb or $^{89}$Zr-DOTA-TmAb (0.56 MBq (15 µCi)) and then sacrificed (biodistribution studies) or imaged (PET/CT studies) at 4, 24, 48 and 72 h p.i. PET images will be reconstructed and SUVs (and % ID/g) will be determined as described above.

After imaging concludes tumors will be harvested from euthanized animals as described above with the following modifications. Sections will be stained with H&E and for Her2/neu expression using an anti-HER2 mAb (EMD Millipore, Billerica, Mass.). Autoradiography and histology will serve to corroborate the data obtained through small animal PET/CT imaging and provide greater proof of Her2/neu antigen binding by the radiotracers.

Statistical Analysis:

To demonstrate that $^{89}$Zr-AMCs retain their robust stability and tumor targeting properties in vivo when conjugated to TmAb, the retention in the tumor, bone, kidney, and liver will be tested at 72 hours for $^{89}$Zr-DOTA-TmAb and $^{89}$Zr-DFO-TmAb. Using a two sided t-test, type 1 error rate of 0.05, and 90% power (n=6 mice/cohort), a difference of approximately two standard deviations will be detectable. The estimable difference detectable for bone accumulation is at least 2.5% ID/g, assuming a standard deviation of at least 1.2. Retention in the tumor, kidney, and liver are expected to be similar in both compounds, but with assumed standard deviations of at least 1.3, the detected differences (if they exist) would be at least 2.7% ID/g. Exploratory analysis estimating retention at the other time points where data is collected will be conducted using a repeated measures generalized linear model to evaluate differences throughout the full period of data collection.

Expected Results:

Due to the elevated temperature needed for $^{89}$Zr-DOTA formation lower radiochemical purities and specific activities associated with $^{89}$Zr-DOTA-TmAb may be encountered. Accordingly, in an alternate embodiment, DOTA will be conjugated to TmAb and then the radiolabelling with $^{89}$Zr will occur. In an alternate embodiment, a modular inverse electron demand Diels-Alder labeling strategy will be employed. Briefly, TmAb will be modified with norbornene-NHS while DOTA will be modified with 3-(4-benzylamino)-1,2,4,5-tetrazine (Tz), and labeled with $^{89}$Zr. The modified mAb and the radiometal chelate will then be reacted to generate the radiolabeled mAb, with an achievable A$_s$ of at least 37 MBq/mg.

It is expected that $^{89}$Zr-DOTA-TmAb will demonstrate similar affinity and immunoreactivity (IR) to $^{89}$Zr-DFO-TmAb, and once in vivo, it is expected that the TmAb will dictate the biodistribution of both radiopharmaceuticals. Furthermore, it is expected that elevated retention of radioactivity will occur in the HER2$^+$ tumors and low retention in the HER2$^-$ tumors. However, less residual activity should localize to the bones of mice injected with $^{89}$Zr-DOTA-TmAb when compared to those animals receiving $^{89}$Zr-DFO-TmAb. This should be evident from biodistribution studies and small animal PET/CT image analysis. Finally, if the intact radiometal chelate is released from TmAb it is expected a biodistribution profile similar to that of $^{89}$Zr-DOTA will be exhibited.

It has been demonstrated that $^{89}$Zr-DOTA is clearly superior to $^{89}$Zr-DFO in terms of in vivo stability, but it may only represent a "local champion" among all AMCs being studied. Additional ligands may emerge that can generate $^{89}$Zr complexes, which have stability comparable to $^{89}$Zr-DOTA, but can form under milder conditions. If more than one ligand forms $^{89}$Zr-complexes that exhibit a superior biodistribution profile to $^{89}$Zr-DFO, then attempts will be made to conjugate these ligands to TmAb and also evaluate their performance.

In an embodiment, the present invention relates to the preparation of $^{89}$Zr-radiopharmaceuticals/complexes and allows the medical imaging community to implement a strategy to provide enhanced clinical imaging services to patients at rural hospitals and clinics without the need for costly radiochemistry infrastructure in order to improve their diagnosis, treatment and quality of care.

Figure 9:
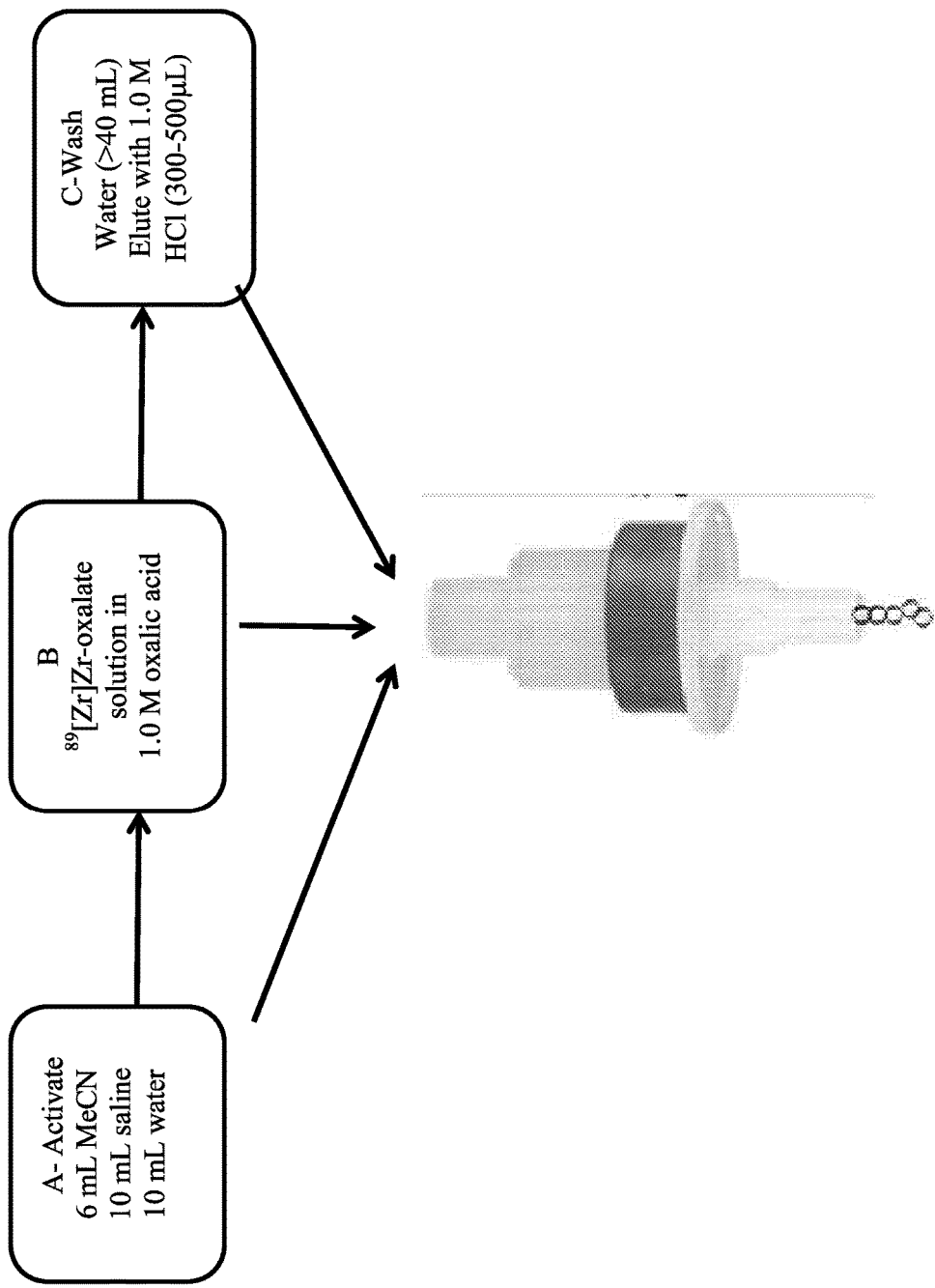
FIG. 9 shows a cartridge that can be used for the preparation of $^{89}$ZrCl$_4$ in steps A-C. After the solid phase extraction cartridge is activated (A), [$^{89}$Zr]Zr-oxalate is added (B). Washing the cartridge with water followed by elution with acid (C) removes the oxalate, and elutes the $^{89}$ZrCl$_4$, which is ready to use in radiochemical synthesis. The total time to complete steps A-C is 15 minutes, which is 75% less time than the next most efficient method for $^{89}$ZrCl$_4$ production.

In an embodiment, the present invention also relates to the formation of $^{89}$ZrCl$_4$ by use of a cartridge (as shown in FIG. 9). The process includes procuring a solid phase extraction cartridge, and then activating the cartridge as shown in step (A). The cartridge is activated by 6 mL acetonitrile, saline and water. Thereafter, [$^{89}$Zr]Zr-oxalate is added as shown in step (B). Washing the cartridge with water followed by elution with acid (C) removes the oxalate, and elutes the $^{89}$ZrCl$_4$, which is ready to use in radiochemical synthesis. The total time to complete steps A-C is 15 minutes, which is 75% less time than the next most efficient method for $^{89}$ZrCl$_4$ production. This facilitates the formation of $^{89}$Zr-radiophamaceuticals, which previously required much longer times as well as much harsher conditions.

It is contemplated and therefore within the scope of the present invention that any of the features described above can be combined with any of the other features described above even if they are not mentioned together. For example it is contemplated that any of the linkers disclosed above can be combined with any of the above disclosed compounds, which in turn may optionally be combined with an antibody. Moreover, it is contemplated that any compound that is disclosed above and in the below can be used in any composition, method, or kit. Minor modifications can be made to the invention without departing from the spirit and scope of the invention. When a range is disclosed it is contemplated and therefore within the scope of the invention that any number that fits within that range is contemplated as an endpoint for a subrange within that disclosed range.

We claim:
1. A composition that comprises a chelator of formula I

Formula I

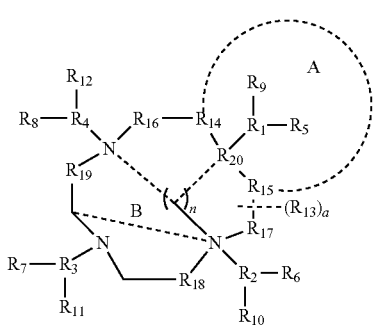

wherein $R_1$, $R_2$, $R_3$, and $R_4$ are independently H or CH;

and wherein when $R_1$ is H, $R_5$ and $R_9$ are not present;

when $R_2$ is H, $R_6$ and $R_{10}$ are not present;

when $R_3$ is H, $R_7$ and $R_{11}$ are not present;

and when $R_4$ is H, $R_8$ and $R_{12}$ are not present;

$R_5$, $R_6$, $R_7$, and $R_8$ are independently H or CH$_3$;

$R_9$, $R_{10}$, $R_{11}$, and $R_{12}$ are independently

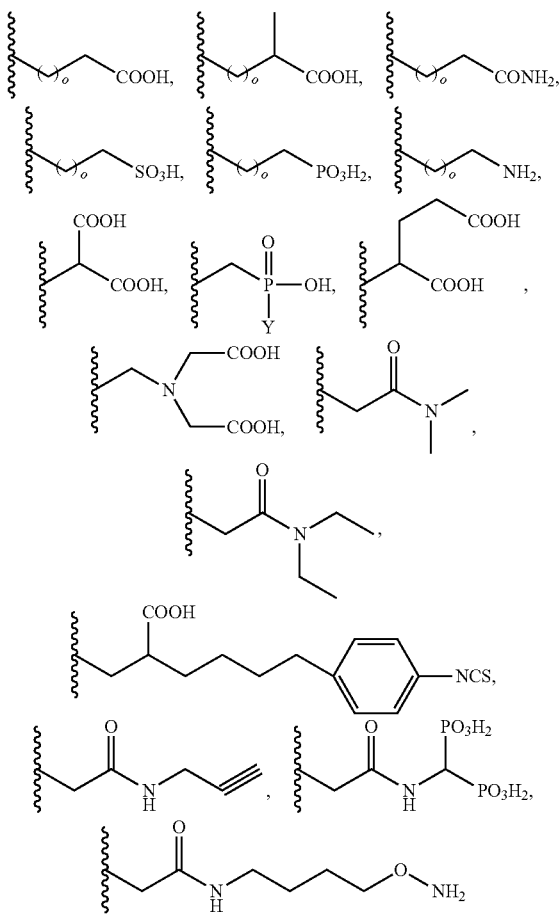

or alternatively, the combination of any one or more of a) $R_1$, $R_5$ and $R_9$, or b) $R_2$, $R_6$, and $R_{10}$, or c) $R_3$, $R_7$, and $R_{11}$, or d) $R_4$, $R_8$ and $R_{12}$ are independently -continued

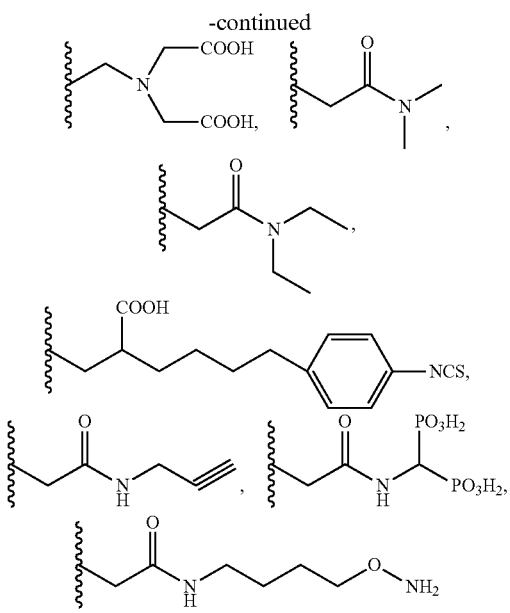

wherein Y is Ph, Bn, Me, Et or n-Bu; and each o is independently an integer 0 or 1;

$R_{13}$ is

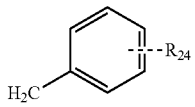

wherein $R_{24}$ is independently H, —OH, —NH2, —C(O)NH$_2$, —NO$_2$, —(CH$_2$)$_{1-3}$O(CH$_2$)$_{1-3}$CH$_3$, —C(O)O(CH$_2$)$_{1-3}$CH$_3$, —OC(O)(CH$_2$)$_{0-3}$CH$_3$, halogen, —(CH$_2$)$_{1-3}$C(O)(CH$_2$)$_{0-3}$CH$_3$, cyano, C$_{2-5}$carboxyl, thiol, —C(O)(CH$_2$)$_{0-3}$CH$_3$, substituted or unsubstituted C$_{1-15}$alkyl, substituted or unsubstituted C$_{1-15}$alkenyl, substituted or unsubstituted C$_{1-15}$alkynyl, substituted or unsubstituted C$_{4-15}$alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)(CH$_2$)$_{0-3}$CH$_3$, C$_{2-5}$carboxyl, —(CH$_2$)$_{1-3}$C(O)(CH$_2$)$_{0-3}$CH$_3$, nitro, amino, thiol, succinimide, maleimide, aminooxyl, acetylene, N$_3$, acetamino, azide, —C(O)O(CH$_2$)$_{1-3}$CH$_3$, —OC(O)(CH$_2$)$_{0-3}$CH$_3$, halogen, C$_{1-5}$alkynyl, and NCS;

a is 0-3;

$R_{14}$ and $R_{15}$ are independently CH or CH$_2$ functionalities; wherein $R_{14}$ and $R_{15}$ are independently CH if and when at least one $R_{13}$ is present;

$R_{16}$, $R_{17}$, $R_{18}$, and $R_{19}$ are —(CH$_2$)$_x$— wherein x is 1, 2, or 3;

$R_{18}$ may optionally be substituted with at least one substituent wherein said substituent is a benzyl amino functionality;

$R_{20}$ is N or O; wherein $R_{20}$ is N if $R_1$, $R_5$ and $R_9$ are present;

and wherein the dotted circle A that comprises the atoms/variables $R_{14}$ and $R_{15}$ and $R_{20}$ to which they are attached may optionally comprise a pyridine group; and when the dotted circle A that contains the atoms/variables $R_{14}$ and $R_{15}$ and the nitrogen to which they are attached comprise a pyridine group, $R_1$, $R_5$, and $R_9$ are not present;

and wherein the chelator optionally has a direct bond represented by the dotted line B;

wherein when the chelator has a direct bond represented by the dotted line B, the intervening linker represented by the group —N—(R$_3$(R$_7$)(R$_{11}$))—CH$_2$—CH$_2$— is not present;

wherein n is 0-4; and when n is 1-4, the chelator comprises either a cis C$_{1-4}$ alkylene group linkage from the nitrogen directly attached to variable R$_2$ to the nitrogen directly attached to R$_1$ or alternatively, a trans linkage from the nitrogen directly attached to variable R$_2$ to the nitrogen directly attached to R$_4$;

wherein the composition further comprises $^{89}$Zr and one or more of chloride, oxalic acid or salts thereof.

2. The composition of claim 1, wherein the composition comprises both $^{89}$Zr and oxalic acid or salts thereof.

3. A kit comprising a) a chelator of formula I

Formula I

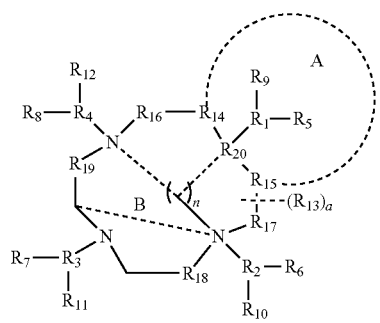

wherein $R_1$, $R_2$, $R_3$, and $R_4$ are independently H or CH;

and wherein when $R_1$ is H, $R_5$ and $R_9$ are not present;

when $R_2$ is H, $R_6$ and $R_{10}$ are not present;

when $R_3$ is H, $R_7$ and $R_{11}$ are not present;

and when $R_4$ is H, $R_8$ and $R_{12}$ are not present;

$R_5$, $R_6$, $R_7$, and $R_8$ are independently H or CH$_3$;

$R_9$, $R_{10}$, $R_{11}$, and $R_{12}$ are independently COOH, CONH$_2$, P(O)—(OH)$_2$;

$R_{13}$ is

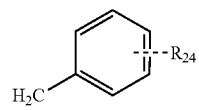

wherein $R_{24}$ is independently H, —OH, —NH2, —C(O)NH$_2$, —NO$_2$, —(CH$_2$)$_{1-3}$O(CH$_2$)$_{1-3}$CH$_3$, —C(O)O(CH$_2$)$_{1-3}$CH$_3$, —OC(O)(CH$_2$)$_{0-3}$ CH$_3$, halogen, —(CH$_2$)$_{1-3}$C(O)(CH$_2$)$_{0-3}$CH$_3$, cyano, C$_{2-5}$carboxyl, thiol, —C(O)(CH$_2$)$_{0-3}$CH$_3$, substituted or unsubstituted C$_{1-15}$alkyl, substituted or unsubstituted C$_{1-15}$alkenyl, substituted or unsubstituted C$_{1-15}$alkynyl, substituted or unsubstituted C$_{4-15}$alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)(CH$_2$)$_{0-3}$CH$_3$, $C_{2-5}$carboxyl, —$(CH_2)_{1-3}C(O)(CH_2)_{0-3}CH_3$, nitro, amino, thiol, succinimide, maleimide, aminooxyl, acetylene, $N_3$, acetamino, azide, —$C(O)O(CH_2)_{1-3}CH_3$, —$OC(O)(CH_2)_{0-3}CH_3$, halogen, $C_{1-5}$alkynyl, and NCS;

a is 0-3;

$R_{14}$ and $R_{15}$ are independently CH or $CH_2$ functionalities; wherein $R_{14}$ and $R_{15}$ are independently CH if and when at least one $R_{13}$ is present;

and wherein the dotted circle A that comprises the atoms/variables $R_{14}$ and $R_{15}$ and the nitrogen to which they are attached may optionally comprise a pyridine group; and when the dotted circle A that contains the atoms/variables $R_{14}$ and $R_{15}$ and the nitrogen to which they are attached comprise a pyridine group, $R_1$, $R_5$, and $R_9$ are not present;

and wherein the chelator optionally has a direct bond represented by the dotted line B;

wherein when the chelator has a direct bond represented by the dotted line B, the intervening linker represented by the group —N—$(R_3(R_7)(R_{11}))$—$CH_2$—$CH_2$— is not present;

wherein n is 0-4; and when n is 1-4, the chelator comprises either a cis $C_{1-4}$ alkylene group linkage from the nitrogen directly attached to variable $R_2$ to the nitrogen directly attached to $R_1$ or alternatively, a trans linkage from the nitrogen directly attached to variable $R_2$ to the nitrogen directly attached to $R_4$;

b) $^{89}ZrCl_4$ and DFO c) oxalic acid or salts thereof.

4. The composition of claim 1, wherein the compound of formula I and $^{89}Zr$ form a complex.

5. The composition of claim 4, wherein the complex is further linked to one or more of a monoclonal antibody, a peptide, a protein, or a nanoparticle.

6. The composition of claim 5, wherein the compound is one or more compounds selected from Formulas III-IX

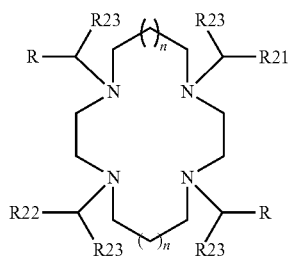

Formula III

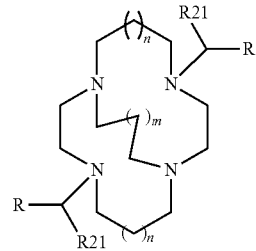

Formula IV

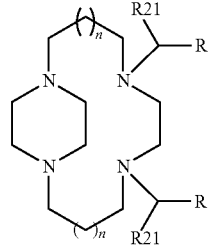

Formula V

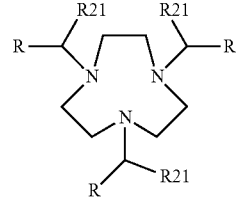

Formula VI

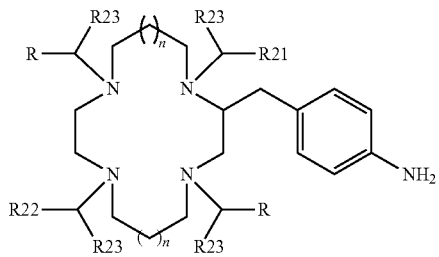

Formula VII

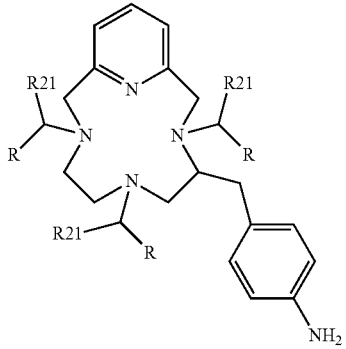

Formula VIII

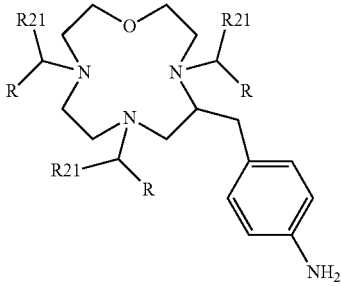

Formula IX wherein in the compounds/chelators represented by Formulae III-IX, n is 0, 1 or 2; m is 0, 1, or 2; R, $R_{21}$, $R_{22}$ and $R_{23}$ are independently selected from the group consisting of

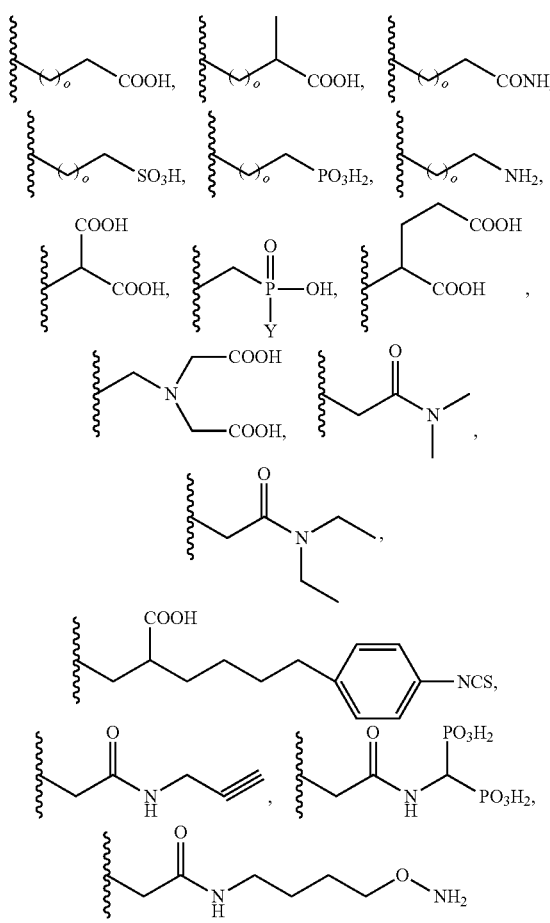

or alternatively, the combination of R, $R_{21}$, $R_{22}$ and $R_{23}$ and the methine group to which they are attached are each independently selected from the group consisting of

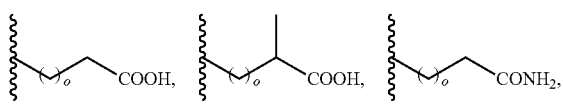

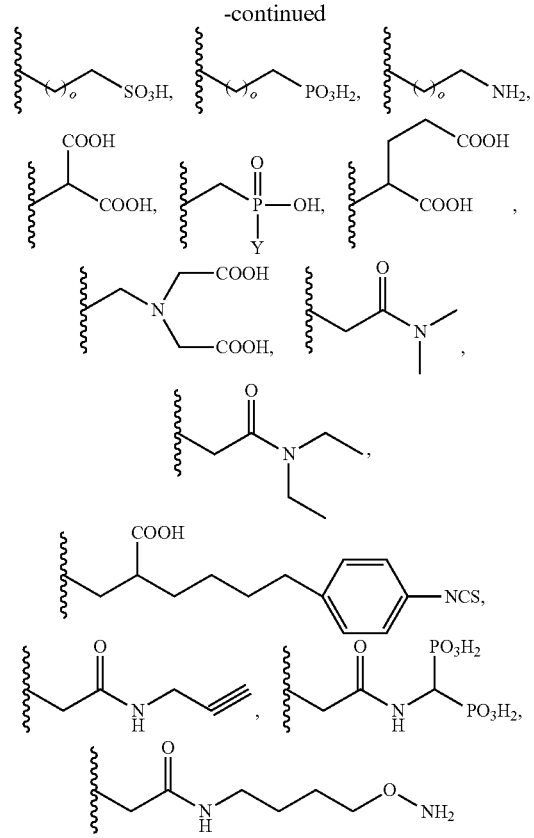

wherein Y is Ph, Bn, Me, Et or n-Bu; and each o is independently an integer 0 or 1.

7. The composition of claim 4, wherein the complex is formed by reacting the compound of formula I with $^{89}ZrCl_4$.

8. The composition of claim 1, further comprising a buffer.

9. The composition of claim 8, wherein the buffer is HEPES buffer.

10. The composition of claim 7, wherein the composition further comprises HEPES buffer.

11. A kit comprising the compound of Formula I in claim 1, and optionally, HEPES buffer and monoclonal antibodies.

12. A method of treating or diagnosing cancer comprising administering to an individual a composition of claim 1.

* * * * *